United States Patent [19]

Tsubotani et al.

[11] Patent Number: 5,556,853
[45] Date of Patent: Sep. 17, 1996

[54] EPOXYSUCCINIC ACID DERIVATIVES

[75] Inventors: Shigetoshi Tsubotani, Kawanishi; Takizawa Masayuki, Kobe; Shirasaki Mikio, Nishinomiya; Yukio Fujisawa, Kobe, all of Japan

[73] Assignee: Takeda Chemical Industries, Ltd., Osaka, Japan

[21] Appl. No.: 330,833

[22] Filed: Oct. 27, 1994

[30] Foreign Application Priority Data

Oct. 29, 1993 [JP] Japan .................... 5-272806
Oct. 29, 1993 [JP] Japan .................... 5-272835
Aug. 8, 1994 [JP] Japan .................... 6-186165

[51] Int. Cl.$^6$ ............. A61K 31/535; C07D 413/12
[52] U.S. Cl. ............. 514/231.5; 514/227.8; 514/252; 514/475; 544/584; 544/146; 544/147; 544/374; 549/548; 549/549
[58] Field of Search .................... 544/147, 374; 549/548, 549; 514/231.5

[56] References Cited

U.S. PATENT DOCUMENTS

| 4,333,879 | 6/1982 | Tamai et al. . | |
|---|---|---|---|
| 4,418,075 | 11/1983 | Tamai et al. . | |
| 4,507,297 | 3/1985 | Masaki et al. | 514/252 |
| 4,596,803 | 6/1986 | Masaki et al. | 514/252 |

FOREIGN PATENT DOCUMENTS

| 0269311 | 6/1988 | European Pat. Off. . |
| 2503709 | 10/1982 | France . |
| 57-72913 | 5/1982 | Japan . |
| 58-55478 | 4/1983 | Japan . |
| 58-126879 | 7/1983 | Japan . |
| 60-8223 | 1/1985 | Japan . |
| 2-218610 | 8/1990 | Japan . |
| 2-304074 | 12/1990 | Japan . |

OTHER PUBLICATIONS

Fukushima et al., "Metabolic Fate of Loxistatin in Rat" Xenobiotica, 1990, vol. 20, No. 10, 1043–1051.

Primary Examiner—Robert W. Ramsuer
Attorney, Agent, or Firm—Wenderoth, Lind & Ponack

[57] ABSTRACT

A compound of the general formula:

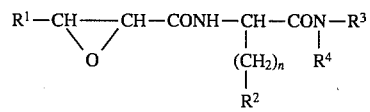

wherein $R^1$ represents a carboxyl group which may optionally be esterified or amidated; $R^2$ represents a cyclic group which may optionally be substituted or a polar group; n is an integer of 0 to 6; $R^3$ represents hydrogen or a hydrocarbon residue which may optionally be substituted; $R^4$ represents (1) a hydrocarbon residue which is substituted by an optionally protected amino group or (2) an alkenyl group; or $R^3$ and $R^4$ may be combined with the adjacent nitrogen atom to form a heterocyclic group containing at least two hetero atoms, or a salt thereof.

The compound or a salt thereof of the present invention inhibits thiol proteases such as cathepsin L and B and serves well as a prophylactic/therapeutic agent for bone diseases such as osteoporosis.

22 Claims, 16 Drawing Sheets

EPOXYSUCCINIC ACID DERIVATIVES

BACKGROUND OF THE INVENTION

1. Field of the Invention

The present invention relates to a new epoxysuccinic acid derivative that inhibits thiol proteases such as cathepsin L and B and serves well as a prophylactic/therapeutic agent for bone diseases such as osteoporosis.

2. Description of Related Art

In bone tissue, bone resorption and formation occur constantly with a good balance to ensure bone homeostasis; bone diseases such as osteoporosis are caused when the balance shifts to the bone resorption side.

In recent years, various epoxy compounds possessing prophylactic/therapeutic activity against bone diseases have been reported (e.g., Japanese Patent Unexamined Publication No. 76–1987, European Patent Publication No. 269311).

Abbreviations for amino acids, peptides and others used in the present specification are based on abbreviations specified by the IUPAC-IUB Commission on Biochemical Nomenclature or abbreviations in common use in relevant fields. When an optical isomer may be present in amino acid, it is of the L-configuration, unless otherwise stated.

Currently, bone resorption suppressors such as estrogens and calcitonin are used to prevent and treat osteoporosis. However, these drugs do not inhibit the thiol protease secreted by the lysosome of osteoclasts. Also, administration of these therapeutic drugs does not always offer satisfactory effect because they are subject to limitation as to subject, and because their efficacy is uncertain in some cases.

With the above situation in mind, the present inventors took note of thiol proteases, especially cathepsin L [H. Kakegawa et al., FEBS Letters, Vol. 321, p. 247 (1993)], which has recently been shown to play a major role in bone resorption, and investigated microbial metabolites with the belief that a drug that selectively inhibits such cathepsin L will serve as a prophylactic/therapeutic agent for bone diseases such as osteoporosis.

Through intensive search, the present inventors found TAN-1756A, B, C and D, represented by the following structural formulas, in microorganisms belonging to the genus *Chaetomium*, and TAN-1854A and B, represented by the following structural formulas, in microorganisms belonging to the genus *Tolypocladium*, TAN-1803, represented by the following structural formula, in a microorganism belonging to the genus *Trichoderma*, and TAN-1868, represented by the following structural formula, in a microorganism belonging to the genus *Aspergillus*. The inventors also developed methods of synthesizing these compounds. The inventors made further investigations of epoxysuccinic acid derivatives based on these findings, and developed the present invention

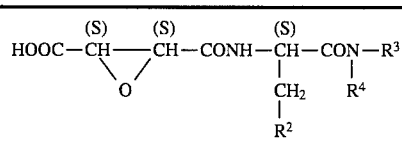

| Compound | $R^2$ | $R^3$ | $R^4$ |
|---|---|---|---|
| TAN-1756A | 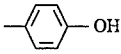 | H | $(CH_2)_4-NH_2$ |
| TAN-1756B | 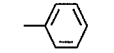—OH | H | $(CH_2)_4-NH_2$ |
| TAN-1854A | 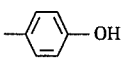 | $(CH_2)_3NH_2$ | $(CH_2)_4-NH_2$ |
| TAN-1854B | 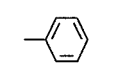—OH | $(CH_2)_3NH_2$ | $(CH_2)_4-NH_2$ |
| TAN-1756C |  | H | $(CH_2)_4NH(CH_2)_3NH_2$ |
| TAN-1756D | 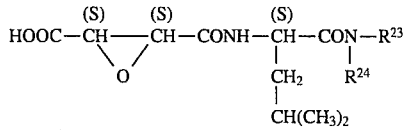 | H | $(CH_2)_3NH(CH_2)_4NH_2$ |

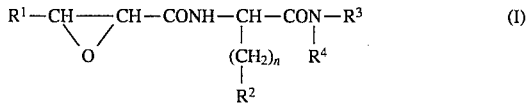

| Compound | $R^{23}$ | $R^{24}$ |
|---|---|---|
| TAN-1803 | $-(CH_2)_4NH_2$ | $-(CH_2)_3NH_2$ |
| TAN-1868 | $-(CH_2)_5NHCOCH_3$ | H |

[(S) indicates that the carbon atom marked therewith is in the S-configuration.]

SUMMARY OF THE INVENTION

The present invention to provide:
(1) a compound of the formula:

$$R^1-CH\underset{O}{\overset{}{\diagdown\!\!\diagup}}CH-CONH-CH-CON-R^3 \quad (I)$$
$$\underset{R^2}{\overset{|}{(CH_2)_n}} \quad R^4$$

wherein $R^1$ represents a carboxyl group which may optionally be esterified or amidated; $R^2$ represents a cyclic group which may optionally be substituted or a polar group; n is an integer of 0 to 6; $R^3$ represents hydrogen or a hydrocarbon residue which may optionally be substituted; $R^4$ represents (1) a hydrocarbon residue which is substituted by an optionally protected amino group or (2) an alkenyl group; or $R^3$ and $R^4$ may be combined with the adjacent nitrogen atom to form a heterocyclic group containing at least two hetero atoms, or a salt thereof;

(2) the compound according to rerun (1) above, wherein $R^1$ is a carboxyl group which may optionally be esterified;

(3) the compound according to term (1) above, wherein $R^1$ is a carboxyl group;

(4) the compound according to term (1) above, wherein $R^2$ is a cyclic group which may optionally be substituted;

(5) the compound according to term (4) above, wherein the cyclic group is an aryl group;

(6) the compound according to term (5) above, wherein the aryl group is $C_{6-14}$ aryl group;

(7) the compound according to term (1) above, wherein the hydrocarbon residue represented by $R^3$ is an alkyl group;

(8) the compound according to term (1) above, wherein $R^4$ is an aminoalkyl group;

(9) the compound according to term (1) above, wherein $R^3$ and $R^4$ are combined with the adjacent nitrogen atom to form a heterocyclic group containing at least two hetero atoms;

(10) the compound according to term (9) above, wherein the heterocyclic group is a 6-membered heterocyclic group;

(11) the compound according to term (1) above, wherein the compound is N-[N-(2S,3S)-3-trans-carboxyoxirane-2-carbonyl]-L-phenylalanyl]-1,4-diaminobutane;

(12) the compound according to term (1) above, wherein the compound is N-[N-(2S,3S)-3-trans-ethoxycarbonyloxirane-2-carbonyl]-L-phenylalanyl]-1,4-diaminobutane;

(13) the compound according to term (1) above, wherein the compound is N-[N-(2S,3S)-3-trans-ethoxycarbonyloxirane-2-carbonyl]-L-phenylalanyl]morpholine;

(14) the compound according to term (1) above, wherein the compound is N-[N-(2S,3S)-3-trans-carboxyoxirane-2-carbonyl]-L-phenylalanyl]morpholine;

(15) the compound according to term (1) above, wherein the compound is N-[N-(2S,3S)-3-trans-ethoxycarbonyloxirane-2-carbonyl]-L-tyrosyl]morpholine;

(16) the compound according to term (1) above, wherein the compound is N-[N-(2S,3S)-3-trans-carbonyloxirane-2-carbonyl]-L-tyrosyl]morpholine;

(17) the compound according to term (1) above, wherein the compound is N-[N-(2S,3S)-3-trans-ethoxycarbonyloxirane-2-carbonyl]-3-(2-naphthyl)-L-alanyl]morpholine;

(18) the compound according to term (1) above, wherein the compound is N-[N-(2S,3S)-3-trans-carboxyoxirane-2-carbonyl]-3-(2-naphthyl)-L-alanyl]morpholine;

(19) a compound of the formula:

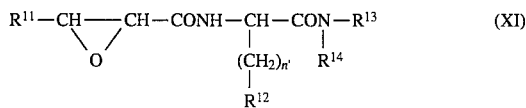

wherein $R^{11}$ represents a carboxyl group which may optionally be esterified or amidated; $R^{12}$ represents an aromatic polycyclic group which may optionally be substituted; n' is an integer of 0 to 6; $R^{13}$ and $R^{14}$, the same or different, represent hydrogen or an alkyl group, or a salt thereof;

(20) the compound according to term (19) above, wherein $R^{11}$ is a carboxyl group which may optionally be esterified;

(21) the compound according to term (19) above, wherein the aromatic polycyclic group is a $C_{8-12}$ dicyclic aromatic group; (22) the compound according to term (19) above, wherein the compound is N-[N-[(2S,3S)-3-trans-ethoxycarbonyloxirane-2-carbonyl]-3-(2-naphthyl)-L-alanyl]-1-amino-3-methylbutane;

(23) the compound according to term (19) above, wherein the compound is N-[N-[(2S,3S)-3-trans-carboxyoxirane-2-carbonyl]-3-(2-naphthyl)-L-amino-3-methylbutane;

(24) a compound of the formula:

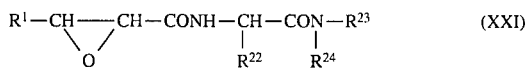

wherein $R^{21}$ represents a carboxyl group which may optionally be esterified or amidated; $R^{22}$ represents an alkyl group; $R^{23}$ and $R^{24}$, the same or different, represent an alkyl group which is substituted by an optionally protected amino group, or a salt thereof;

(25) the compound according to term (24) above, wherein $R^{21}$ is a carboxyl group;

(26) the compound according to term (24) above, wherein $R^{22}$ is $C_{3-5}$ alkyl group;

(27) the compound according to term (24) above, wherein $R^{23}$ and $R^{24}$ are both aminoalkyl groups;

(28) a composition for inhibition of a thiol protease, which comprises a compound or a salt thereof as defined in term (1), (19) or (24) above;

(29) a composition for preventing or treating a bone disease, which comprises a compound or a salt thereof as defined in term (1), (19) or (24) above; and (30) the composition according to term (29) above, wherein the bone disease is osteoporosis.

DETAILED DESCRIPTION OF THE INVENTION

Figure 1:
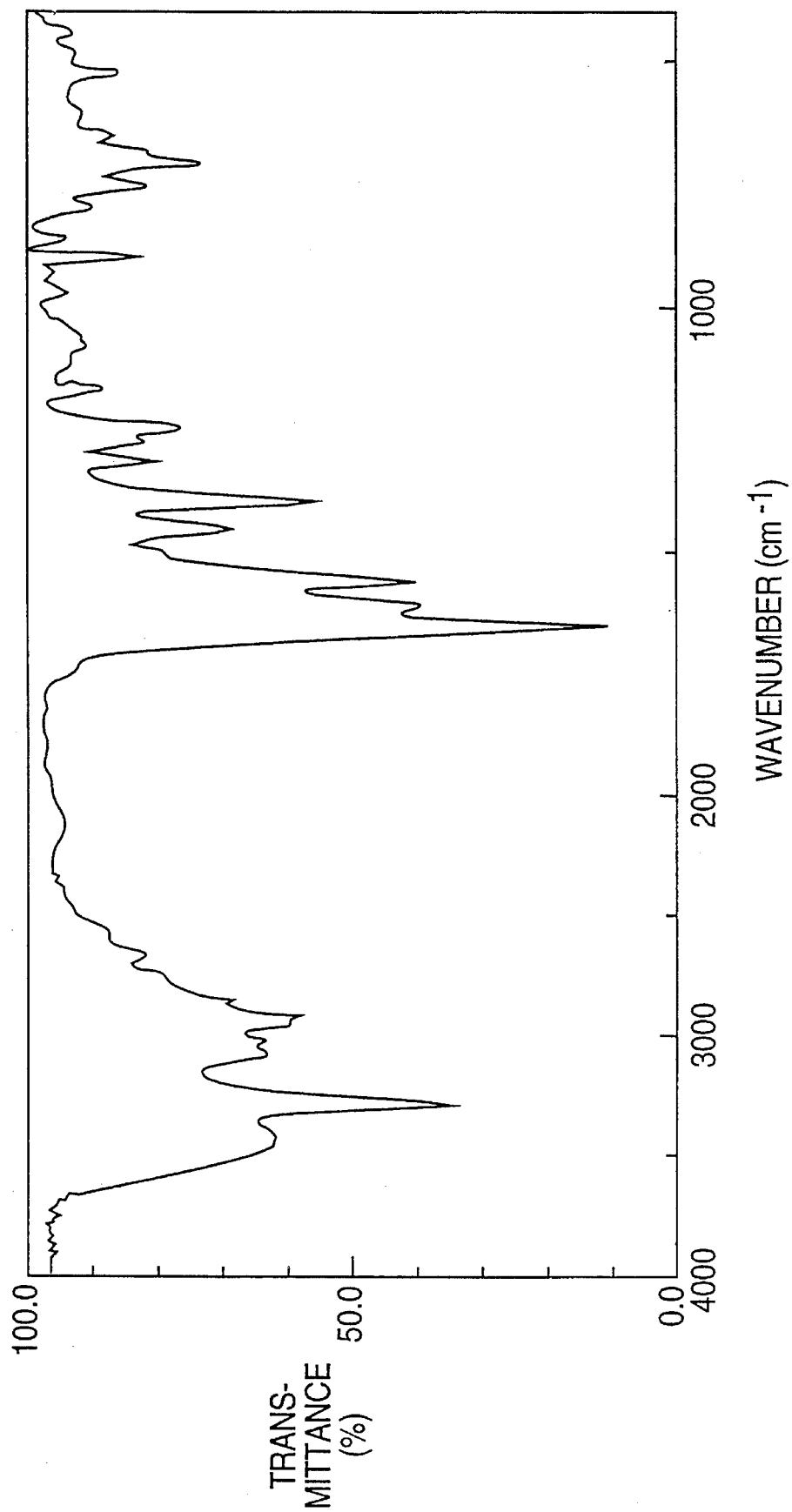
FIG. 1 is the IR spectrum of TAN-1756A.

With respect to general formula (I) above, the carboxyl group for $R^1$ which may optionally be esterified is exemplified by pharmacologically acceptable ones or those which become pharmacologically acceptable in the body. Preferable esterified carboxyl groups are represented by, the formula —$COOR^5$, wherein $R^5$ stands for, for example, (1) $C_{1-6}$ alkyl groups (e.g. methyl, ethyl, propyl, isopropyl, butyl, isobutyl, sec-butyl, tert-butyl, pentyl, isopentyl, sec-pentyl, neopentyl, tert-pentyl, hexyl, etc.) optionally having 1 to 3 substituents selected from (a) nitro group, (b) halogen (e.g. bromine, chlorine, fluorine, etc.) and (c) $C_{2-6}$ alkanoyloxy group (e.g. acetyloxy, propionyloxy, isopropionyloxy, butyryloxy, isobutyryloxy, valeryloxy, isovaleryloxy, pivaloyloxy, hexanoyloxy, etc.), (2) $C_{6-14}$ aryl group (e.g. phenyl, naphthyl, etc.) optionally having 1 to 3 substituents selected from (a) nitro group, (b) halogen (bromine, chlorine, fluorine, etc.) and (c) $C_{1-4}$ alkoxy groups (e.g. methoxy, ethoxy, propoxy, isopropoxy, butoxy, sec-butoxy, tert-butoxy, etc.) and (3) $C_{7-12}$ aralkyl groups (e.g. benzyl, phenethyl, etc.) optionally having 1 to 3 substituents selected from (a) nitro group, (b) halogen (e.g. bromine, chlorine, fluorine, etc.) and (c) $C_{1-4}$ alkoxy groups (e.g. methoxy, ethoxy, propoxy, isopropoxy, butoxy, isobutoxy, sec-butoxy, tert-butoxy, etc.).

Preferable examples of $R^5$ include $C_{1-6}$ alkyl groups (e.g. methyl, ethyl, propyl, isopropyl, butyl, isobutyl, sec-butyl, tert-butyl, pentyl, isopentyl, secpentyl, neopentyl, tert-pentyl, hexyl, etc.) optionally having 1 to 3 substituents selected from (a) nitro group, (b) halogen (e.g. bromine, chlorine, fluorine, etc.) and (c) $C_{2-6}$ alkanoyloxy groups (e.g. acetyloxy, propionyloxy, isopropionyloxy, butyryloxy, isobutyryloxy, valeryloxy, isovaleryloxy, pivaloyloxy, hexanoyloxy, etc.).

More preferable examples of $R^5$ include $C_{1-6}$ alkyl groups (e.g. methyl, ethyl, propyl, isopropyl, butyl, isobutyl, sec-butyl, tert-butyl, pentyl, isopentyl, sec-pentyl, neopentyl, tert-pentyl, hexyl, etc.).

With respect to general formula (I), the carboxyl group for $R^1$ which may optionally be amidated is exemplified by pharmacologically acceptable ones or those which become pharmacologically acceptable in the body. Preferable amidated carboxyl groups are represented by the formula, —CONHR$^6$, wherein R$^6$ stands for, for example, (1) hydrogen, (2) C$_{1-6}$ alkyl groups (e.g. methyl, ethyl, propyl, isopropyl, butyl, isobutyl, sec-butyl, tert-butyl, pentyl, isopentyl, sec-pentyl, neopentyl, tert-pentyl, hexyl, etc.) optionally having 1 to 3 substituents selected from (a) nitro group, (b) halogen (e.g. bromine, chlorine, fluorine, etc.), (3) C$_{6-14}$ aryl groups (e.g. phenyl, naphthyl, etc.) optionally having 1 to 3 substituents selected from (a) nitro group, (b) halogen (e.g. bromine, chlorine, fluorine, etc.) and (c) C$_{1-4}$ alkoxy group (e.g. methoxy, ethoxy, propoxy, isopropoxy, butoxy, isobutoxy, sec-butoxy, tert-butoxy), and (4) C$_{7-12}$ aralkyl groups (e.g. benzyl, phenethyl, etc.) optionally having 1 to 3 substituents selected from (a) nitro group, (b) halogen (e.g. bromine, chlorine, fluorine, etc.) and (c) C$_{1-4}$ alkoxy groups (methoxy, ethoxy, propoxy, isopropoxy, butoxy, isobutoxy, sec-butoxy, tert-butoxy, etc.)

Preferable examples of R$^6$ include C$_{1-6}$ alkyl groups (e.g. methyl, ethyl, propyl, isopropyl, butyl, isobutyl, sec-butyl, tert-butyl, pentyl, isopentyl, sec-pentyl, neopentyl, tert-pentyl, hexyl, etc.) optionally having 1 to 3 substituents selected from (a) nitro group and (b) halogen (e.g. bromine, chlorine, fluorine, etc.).

More preferable examples of R$^6$ include C$_{1-6}$ alkyl groups (e.g. methyl, ethyl, propyl, isopropyl, butyl, isobutyl, sec-butyl, tert-butyl, pentyl, isopentyl, sec-pentyl, neopentyl, tert-pentyl, hexyl, etc.).

With respect to general formula (I), R$^1$ is preferably a carboxyl group which may optionally be esterified. More preferably, R$^1$ is a carboxyl group which may optionally be esterified by C$_{1-6}$ alkyl groups (e.g. methyl, ethyl, propyl, isopropyl, butyl, isobutyl, sec-butyl, tert-butyl, pentyl, isopentyl, secpentyl, neopentyl, tert-pentyl, hexyl, etc.).

With respect to general formula (I) above, the cyclic group for R$^2$ which may optionally be substituted is exemplified by (1) C$_{3-8}$ cycloalkyl groups (e.g., cyclopropyl, cyclobutyl, cyclopentyl, cyclohexyl), (2) C$_{3-8}$ cycloalkenyl groups (e.g., cyclopropenyl, 1-cyclopentenyl, 2-cyclopentenyl, 3-cyclopentenyl, 1-cyclohexenyl, 2-cyclohexenyl, 3-cyclohexenyl), (3) C$_{6-14}$ aryl groups (e.g., phenyl, 1- or 2-naphthyl, 1-, 2- or 9-anthryl, 1-, 2-, 3-, 4- or 9-phenanthryl, 1-, 2-, 4-, 5- or 6-azulenyl), and (4) 5- or 6-membered heterocyclic groups containing 1 to 4 hetero atoms selected from oxygen, sulfur, nitrogen etc., in addition to carbon atoms, or condensed heterocyclic groups thereof (e.g., 2- or 3-thienyl, 2- or 3-furyl, 2- or 3-pyrrolyl, 3-, 4- or 5-pyrazolyl, 2-, 4- or 5-thiazolyl, 3-, 4- or 5-isothiazolyl, 2-, 4- or 5-oxazolyl, 3-, 4- or 5-isoxazolyl, 2-, 4- or 5-imidazolyl, 1,2,3- or 1,2,4-triazolyl, 1H- or 2H-tetrazolyl, 2-, 3- or 4-pyridyl, 2-, 4- or 5-pyrimidyl, 3- or 4- pyridazinyl, quinolyl, isoquinolyl, indolyl).

Of these groups, C$_{6-14}$ aryl (e.g., phenyl, 1- or 2-naphthyl, 1-, 2- or 9-anthryl, 1-, 2-, 3-, 4- or 9-phenanthryl, 1-, 2-, 4-, 5- or 6-azulenyl), and 5- or 6-membered heterocyclic rings containing 1 to 4 hetero atoms selected from oxygen, sulfur, nitrogen etc., in addition to carbon atoms, or condensed heterocyclic groups thereof (e.g., 2- or 3-thienyl, 2- or 3-furyl, 2- or 3-pyrrolyl, 2- or 3-indolyl, 2-, 4- or 5-imidazolyl) are preferred. The cyclic group is more preferably C$_{6-14}$ aryl groups (e.g., phenyl, 1- or 2-naphthyl, 1-, 2- or 9-anthryl, 1-, 2-, 3-, 4- or 9-phenanthryl, 1-, 2-, 4-, 5- or 6-azulenyl), with greater preference given to C$_{6-10}$ aryl groups (e.g., phenyl, 1- or 2-naphthyl).

The above-described cyclic group may optionally have, at any possible positions, 1 to 5 substituents selected from, for example, (1) C$_{1-15}$ alkyl groups (e.g. methyl, ethyl, propyl, isopropyl, butyl, isobutyl, sec-butyl, tert-butyl, pentyl, isopentyl, sec-pentyl, neopentyl, tert-pentyl, hexyl, heptyl, octyl, nonyl, decyl, undecyl, dodecyl, tridecyl, tetradecyl, pentadecyl, etc.) having optionally 1 to 3 substituents selected from (a) nitro group, (b) halogen (e.g. bromine, chlorine, fluorine, etc.), (2) C$_{3-10}$ cycloalkyl groups (e.g. cyclopropyl, cyclobutyl, cyclopentyl, cyclohexyl, etc.), (3) C$_{2-10}$ alkenyl groups (e.g. vinyl, allyl, 2-methylallyl, 2-butenyl, 3-butenyl, 3-octenyl, etc.) optionally having 1 to 3 substituents selected from (a) nitro group, (b) halogen (e.g. bromine, chlorine, fluorine, etc.), (4) C$_{2-10}$ alkynyl groups (e.g. ethynyl, 2-propinyl, 3-hexynyl, etc.), (5) C$_{3-10}$ cycloalkenyl groups (e.g. cyclopropenyl, cyclopentenyl, cyclohexenyl, etc.), (6) C$_{6-10}$ aryl groups (e.g. phenyl, naphthyl, etc.), (7) C$_{7-12}$ aralkyl groups (e.g. benzyl, phenethyl, etc.), (8) nitro group, (9) hydroxyl group, (10) mercapto group, (11) oxo group, (12) thioxo group, (13) cyano group, (14) carbamoyl group, (15) carboxyl group, (16) C$_{2-5}$ alkoxycarbonyl groups (e.g. methoxycarbonyl, ethoxycarbonyl, etc.), (17) C$_{7-11}$ aryloxycarbonyl groups (e.g. phenoxycarbonyl, etc.), (18) C$_{8-13}$ aralkyloxycarbonyl groups (e.g. benzyloxycarbonyl, phenethyloxycarbonyl, etc.), (19) sulfo group, (20) halogen (e.g. fluorine, chlorine, bromine or iodine), (21) C$_{1-4}$ alkoxy groups (e.g. methoxy, ethoxy, propoxy, isopropoxy, butoxy, isobutoxy, sec-butoxy, tert-butoxy, etc.), (22) C$_{6-10}$ aryloxy groups (e.g. phenoxy, etc.), (23) C$_{7-12}$ aralkyloxy groups (e.g. benzyloxy, phenethyloxy, etc.), (24) C$_{1-6}$ alkanoyloxy groups (e.g. formyloxy, acetyloxy, propionyloxy, isopropionyloxy, butyryloxy, isobutyryloxy, valeryloxy, isovaleryloxy, pivaloyloxy, hexanoyloxy, etc.), (25) C$_{7-11}$ arylcarbonyloxy groups (e.g. benzoyloxy, p-toluoyloxy, 1-naphthoyloxy, 2-naphthoyloxy, etc.), (26) C$_{1-4}$ alkylthio groups (e.g. methylthio, ethylthio, n-propylthio, isopropylthio, n-butylthio, tert-butylthio, etc.), (27) C$_{6-10}$ arylthio groups (e.g. phenylthio, naphthylthio, etc.), (28) C$_{1-6}$ alkylsulfinyl groups (e.g. methylsulfinyl, ethylsulfinyl, propylsulfinyl, etc.), (29) C$_{6-10}$ arylsulfinyl groups (e.g. phenylsulfinyl, etc.), (30) C$_{1-6}$ alkylsulfonyl groups (e.g. methylsulfonyl, ethylsulfonyl, propylsulfonyl, etc.), (31) C$_{6-10}$ arylsulfonyl groups (e.g. phenylsulfonyl, tosyl, etc.), (32) amino group, (33) C$_{1-6}$ alkanoylamino groups (e.g. acetylamino, propionylamino, etc.), (34) mono- or di-C$_{1-4}$ alkylamino groups (e.g. methylamino, ethylamino, n-propylamino, isopropylamino, n-butylamino, dimethylamino, diethylamino, etc.), (35) C$_{3-8}$ cycloalkylamino groups (e.g. cyclopropylamino, cyclobutylamino, cyclopentylamino, cyclohexylamino, etc.), (36) C$_{6-10}$ arylamino groups (e.g. anilino, etc.), (37) C$_{7-11}$ arylcarbonylamino groups (e.g. benzoylamino, p-toluoylamino, 1-naphthoylamino, 2-naphthoylamino, etc.), (38) C$_{2-5}$ alkoxycarbonylamino groups (e.g. methoxycarbonylamino, ethoxycarbonylamino, tert-butoxycarbonylamino, etc.), (39) C$_{8-13}$ aralkyloxycarbonylamino groups (e.g. benzyloxycarbonylamino, phenethyloxycarbonylamino, etc.), (40) C$_{1-6}$ alkylsulfonylamino groups (e.g. methylsulfonylamino, ethylsulfonylamino, propylsulfonylamino, etc.), (41) C$_{6-10}$ arylsulfonylamino groups (e.g. phenylsulfonylamino, tosylamino, etc.), (42) mono-or di-C$_{1-4}$ alkylcarbamoyl groups (e.g. methylcarbamoyl, ethylcarbamoyl, n-propylcarbamoyl, isopropylcarbamoyl, n-butylcarbamoyl, dimethylcarbamoyl, diethylcarbamoyl, etc.), (43) C$_{1-6}$ alkanoyl groups (e.g. formyl, acetyl, propionyl, isopropionyl, butyryl, isobutyryl, valeryl, isovaleryl, pivaloyl, hexanoyl, etc.), (44) C$_{7-11}$ arylcarbonyl groups (e.g. benzoyl, p-toluoyl, 1-naphthoyl, 2-naphthoyl, etc.), (45) C$_{8-13}$ aralkylcarbonyl groups (e.g. benzylcarbonyl, phenethylcarbonyl, etc.) and (46) 5- to 6-membered heterocyclic groups containing 1 to 4 heteroatoms selected from oxygen, sulfur, nitrogen, etc., in addition to carbon atoms, or condensed heterocyclic groups thereof (e.g. 2- or 3-thienyl, 2- or 3-furyl, 2- or 3-pyrrolyl, 3-, 4- or 5-pyrazolyl 2-, 4- or 5-thiazolyl, 3-, 4- or 5-isothiazolyl, 2-, 4- or 5-oxazoyl, 3-, 4- or 5-isoxazolyl, 2-, 4- or 5-imidazolyl, 1,2,3- or 1,2,4-triazolyl, 1H- or 2H-tetrazolyl, 2-, 3- or 4-pyridyl, 2-, 4- or 5-pyrimidyl, 3- or 4-pyridazinyl, quinolyl, isoquinolyl, indolyl, etc.).

With respect to general formula (I), the polar group for $R^2$ is exemplified by (1) nitro group, (2) hydroxyl group, (3) oxo group, (4) thioxo group, (5) cyano group, (6) carbamoyl group, (7) carboxyl group, (8) $C_{2-5}$ alkoxycarbonyl groups (e.g. methoxycarbonyl, ethoxycarbonyl etc.), (9) $C_{8-13}$ aralkyloxycarbonyl groups (e.g. benzyloxycarbonyl, phenethyloxycarbonyl, etc.), (10) $C_{7-11}$ aryloxycarbonyl groups (e.g. phenoxycarbonyl, etc.), (11) sulfo group, (12) mercapto group, (13) $C_{1-4}$ alkoxy groups (e.g. methoxy, ethoxy, propoxy, isopropoxy, butoxy, isobutoxy, sec-butoxy, tert-butoxy, etc.), (14) $C_{6-10}$ 10 aryloxy groups (e.g. phenoxy group, etc.), (15) $C_{7-12}$ aralkyloxy groups (e.g. benzyloxy, phenethyloxy, etc.), (16) $C_{1-6}$ alkanoyloxy groups (e.g. formyloxy, acetyloxy, propionyloxy, isopropionyloxy, butyryloxy, isobutyryloxy, valeryloxy, isovaleryloxy, pivaloyloxy, hexanoyloxy, etc.), (17) $C_{7-11}$ arylcarbonyloxy groups (e.g. benzoyloxy, p-toluoyloxy, 1-naphthoyloxy, 2-naphthoyloxy, etc.), (18) $C_{1-4}$ alkylthio groups (e.g. methylthio, ethylthio, n-propylthio, isopropylthio, n-butylthio, tert-butylthio, etc.), (19) $C_{6-10}$ arylthio groups (e.g. phenylthio, naphthylthio, etc.), (20) $C_{7-19}$ aralkylthio groups (e.g. benzylthio, tritylthio, etc.), (21) $C_{1-6}$ alkylsulfinyl groups (e.g. methylsulfinyl, ethylsulfinyl, propylsulfinyl, etc.), (22) $C_{6-10}$ arylsulfinyl groups (e.g. phenylsulfinyl, etc.), (23) $C_{1-6}$ alkylsulfonyl groups (e.g. methylsulfonyl, ethylsulfonyl, propylsulfonyl, etc.) optionally substituted with 1 to 3 halogen atoms (e.g. fluorine, chlorine, iodine, etc.), (24) $C_{6-10}$ arylsulfonyl groups (e.g. phenylsulfonyl, tosyl, etc.), (25) amino group, (26) $C_{1-8}$ alkanoylamino groups (e.g. acetylamino, propionylamino, etc.), (27) mono- or di-$C_{1-4}$ alkylamino groups (e.g. methylamino, ethylamino, n-propylamino, isopropylamino, n-butylamino, dimethylamino, diethylamino, etc.), (28) $C_{7-11}$ arylcarbonylamino groups (e.g. benzoylamino, p-toluoylamino, 1-naphthoylamino, 2-naphthoylamino, etc.), (29) $C_{2-5}$ alkoxycarbonylamino groups (e.g. methoxycarbonylamino, ethoxycarbonylamino, tert-butoxycarbonylamino, etc.), (30) $C_{8-13}$ aralkyloxycarbonylamino groups (e.g. benzyloxycarbonylamino, phenethyloxycarbonylamino, etc.), (31) $C_{1-6}$ alkylsulfonylamino groups (e.g. methylsulfonylamino, ethylsulfonylamino, etc.), (32) $C_{6-10}$ arylsulfonylamino groups (e.g. phenylsulfonylamino, tosylamino, etc.), (33) $C_{1-6}$ alkanoyl groups (e.g. formyl, acetyl, propionyl, isopropionyl, butyryl, isobutyryl, valeryl, isovaleryl, pivaloyl, hexanoyl, etc.), (34) $C_{8-13}$ aralkylcarbonyl groups (e.g. benzylcarbonyl, phenethylcarbonyl, etc.), (35) $C_{7-11}$ arylcarbonyl groups (e.g. benzoyl, p-toluoyl, 1-naphthoyl, 2-naphthoyl etc.), (36) mono- or di-$C_{1-4}$ alkylcarbamoyl groups (e.g. methylcarbamoyl, ethylcarbamoyl, n-propylcarbamoyl, isopropylcarbamoyl, n-butylcarbamoyl, dimethylcarbamoyl, diethylcarbamoyl, etc.), (37) phosphono group, (38) mono- or di-$C_{1-4}$ alkylphosphono groups (e.g. methylphosphono, ethylphosphono, n-propylphosphono, isopropylphosphono, n-butylphosphono, dimethylphosphono, diethylphosphono, etc.), (39) guanidyl groups optionally substituted with nitro group, (40) amidino group, (41) mono- or di-$C_{1-4}$ alkylsulfamoyl groups (e.g. methylsulfamoyl, ethylsulfamoyl, n-propylsulfamoyl, isopropylsufamoyl, n-butylsulfamoyl, dimethylsulfarnoyl, diethylsulfamoyl, etc.), etc.

Among these groups, (1) hydroxyl group, (2) carbamoyl group, (3) carboxyl group, (4) $C_{2-15}$ alkoxycarbonyl groups (e.g. methoxycarbonyl, ethoxycarbonyl, etc.), (5) $C_{8-13}$ aralkyloxycarbonyl groups (e.g. benzyloxycarbonyl, phenethyloxycarbonyl, etc.), (6) $C_{7-11}$ aryloxycarbonyl groups (e.g. phenoxycarbonyl etc.), (7) $C_{1-4}$ alkoxy groups (e.g. methoxy, ethoxy, propoxy, isopropoxy, butoxy, isobutoxy, sec-butoxy, tert-butoxy, etc.), (8) $C_{6-10}$ aryloxy groups (e.g. phenoxy, etc.), (9) $C_{7-12}$ aralkyloxy groups (e.g. benzyloxy, phenethyloxy, etc.), (10) $C_{1-6}$ alkanoyloxy groups (e.g. formyloxy, acetyloxy, propionyloxy, isopropionyloxy, butyryloxy, isobutyryloxy, valeryloxy, isovaleryloxy, pivaloyloxy, hexanoyloxy, etc.), (11) $C_{7-11}$ arylcarbonyloxy groups (e.g. benzoyloxy, p-toluoyloxy, 1-naphthoyloxy, 2-naphthoyloxy, etc.), (12) amino group, (13) $C_{1-6}$ alkanoylamino groups (e.g. acetylamino, propionylamino, etc.), (14) mono- or di-$C_{1-4}$ alkylamino groups (e.g. methylamino, ethylamino, n-propylamino, isopropylamino, n-butylamino, dimethylamino, diethylamino, etc.), (15) $C_{7-11}$ arylcarbonylamino groups (e.g. benzoylamino, p-toluoylamino, 1-naphthoylamino, 2-naphthoylamino, etc.), (16) $C_{2-5}$ alkoxycarbonylamino groups (e.g methoxycarbonylamino, ethoxycarbonylamino, tert-butoxycarbonylamino, etc.), (17) $C_{8-13}$ aralkyloxycarbonylamino groups (e.g. benzyloxycarbonylamino, phenethyloxycarbonylamino, etc.), (18) $C_{1-6}$ alkylsulfonylamino groups (e.g. methylsulfonylamino, ethylsulfonylamino, etc.), (9) $C_{6-10}$ arylsulfonylamino groups (e.g. phenylsulfonylamino, tosylamino, etc.), etc. are preferable.

With respect to general formula (I), $R^2$ is preferably a cyclic group which may optionally be substituted. More preferably, $R^2$ is $C_{6-10}$ aryl group (e.g. phenyl, 1- or 2-naphthyl, etc.) which may optionally be substituted.

With respect to general formula (I) above, the hydrocarbon residue for $R^3$ which may optionally be substituted is exemplified by $C_{1-15}$ alkyl groups (e.g., methyl, ethyl, propyl, isopropyl, butyl, isobutyl, sec-butyl, tert-butyl, pentyl, hexyl, heptyl, octyl, nonyl, decyl, undecyl, dodecyl, tridecyl, tetradecyl, pentadecyl), $C_{3-8}$ cycloalkyl groups (e.g., cyclopropyl, cyclobutyl, cyclopentyl, cyclohexyl), $C_{2-10}$ alkenyl groups (e.g., vinyl, allyl, 2-methylallyl, 2-butenyl, 3-butenyl, 3-octenyl), $C_{2-10}$ alkynyl groups (e.g., ethynyl, 2-propynyl, 3-hexynyl), $C_{3-10}$ cycloalkenyl groups (e.g., cyclopropenyl, cyclopentenyl, cyclohexenyl), $C_{6-14}$ aryl groups (e.g., phenyl, naphthyl), and $C_{7-16}$ aralkyl groups (e.g., benzyl, phenylethyl).

Of these groups, $C_{1-15}$ alkyl groups (e.g., methyl, ethyl, propyl, isopropyl, butyl, isobutyl, sec-butyl, tert-butyl, pentyl, hexyl, heptyl, octyl, nonyl, decyl, undecyl, dodecyl, tridecyl, tetradecyl, pentadecyl) are preferred.

Such hydrocarbon groups may have, at any possible positions, 1 to 5 substituents selected from, for example, (1) nitro group, (2) hydroxyl group, (3) oxo group, (4) thioxo group, (5) cyano group, (6) carbamoyl group, (7) carboxyl group, (8) $C_{2-5}$ alkoxycarbonyl groups (e.g. methoxycarbonyl, ethoxycarbonyl, etc.), (9) $C_{8-13}$ aralkyloxycarbonyl groups (e.g. benzyloxycarbonyl, phenethyloxycarbonyl, etc.), (10) $C_{7-11}$ aryloxycarbonyl groups (e.g. phenoxycarbonyl, etc.), (11) sulfo group, (12) halogen (e.g. fluorine, chlorine, bromine, iodine, etc.), (13) $C_{1-4}$ alkoxy groups (e.g. methoxy, ethoxy, propoxy, isopropoxy, butoxy, isobutoxy, sec-butoxy, tert-butoxy, etc.), (14) $C_{6-10}$ aryloxy groups (e.g. phenoxy, etc.), (15) halogenophenoxy (e.g. o-, m- or p-chlorophenoxy, o-, m- or p-bromophenoxy, etc.), (16) $C_{7-12}$ aralkyloxy groups (e.g. benzyloxy, phenethyloxy, etc.), (17) $C_{1-6}$ alkanoyloxy groups (e.g. formyloxy, acetyloxy, propionyloxy, isopropionyloxy, butyryloxy, isobutyryloxy, valeryloxy, isovaleryloxy, pivaloyloxy, hexanoyloxy, etc.), (18) $C_{7-11}$ arylcarbonyloxy groups (e.g. benzoyloxy, p-toluoyloxy, 1-naphthoyloxy, 2-naphthoyloxy, etc.), (19) $C_{1-4}$ alkylthio groups (e.g. methylthio, ethylthio, n-propylthio, isopropylthio, n-butylthio, tert-butylthio, etc.), (20) $C_{6-10}$ arylthio groups (e.g. phenylthio, naphthylthio, etc.), (21) $C_{1-6}$ alkylsulfinyl groups (e.g. methylsulfinyl, ethylsulfinyl, propylsulfinyl, etc.), (22) $C_{6-10}$ arylsulfinyl groups (e.g. phenylsulfinyl, etc.), (23) $C_{1-6}$ alkylsulfonyl groups (e.g. methylsulfonyl, ethylsulfonyl, propylsulfonyl, etc.), (24) $C_{6-10}$ arylsulfonyl groups (e.g. phenylsulfonyl, tosyl, etc.), (25) amino, (26) $C_{1-6}$ alkanoylamino groups (e.g. acetylamino, propionylamino, etc.), (27) mono- or di-$C_{1-4}$ alkylamino groups (e.g. methylamino, ethylamino, n-propylamino, isopropylamino, n-butylamino, dimethylamino, diethylamino, etc.), (28) $C_{7-11}$ arylcarbonylamino groups (e.g. benzoylamino, p-toluoylamino, 1-naphthoylamino, 2-naphthoylamino, etc.), (29) $C_{1-5}$ alkoxycarbonylamino groups (methoxycarbonylamino, ethoxycarbonylamino, tert-butoxycarbonylamino, etc.), (30) $C_{8-13}$ aralkyloxycarbonylamino groups (e.g. benzyloxycarbonylamino, phenethyloxycarbonylamino, etc.), (31) $C_{1-6}$ alkylsulfonylamino groups (e.g. methylsulfonylamino, ethylsulfonylamino, etc.), (32) $C_{6-10}$ arylsulfonylamino groups (e.g. phenylsulfonylamino, tosylamino, etc.), (33) $C_{1-6}$ alkanoyl groups (e.g. formyl, acetyl, propionyl, isopropionyl, butyryl, isobutyryl, valeryl, isovaleryl, pivaloyl, hexanoyl, etc.), (34) $C_{8-13}$ aralkylcarbonyl groups (e.g. benzylcarbonyl, phenethylcarbonyl, etc.), (35) $C_{7-11}$ arylcarbonyl groups (e.g. benzoyl, p-toluoyl, 1-naphthoyl, 2-naphthoyl, etc.), (36) mono- or di-$C_{1-4}$ alkylcarbamoyl groups (e.g. methylcarbamoyl, ethylcarbamoyl, n-propylcarbamoyl, isopropylcarbamoyl, n-butylcarbamoyl, dimethylcarbamoyl, diethylcarbamoyl, etc.), (37) phosphono groups, (38) mono- or di-$C_{1-4}$ alkylphosphono groups (e.g. methylphosphono, ethylphosphono, n-propylphosphono, isopropylphosphono, n-butylphosphono, dimethylphosphono, diethylphosphono, etc.), (39) guanidyl groups optionally substituted with nitro group, (40) amidino group, (41) 5- or 6-membered heterocyclic groups containing 1 to 4 hetero-atoms selected from oxygen, sulfur, nitrogen, etc., in addition to carbon atoms, or condensed heterocyclic groups thereof (e.g. 2- or 3-thienyl, 2- or 3-furyl, 2- or 3-pyrrolyl, 3-, 4- or 5-pyrazolyl, 2-, 4- or 5-thiazolyl, 3-, 4- or 5-isothiazolyl, 2-, 4- or 5-oxazolyl, 3-, 4- or 5-isoxazolyl, 2-, 4- or 5-imidazolyl, 1,2,3- or 1,2,4-triazolyl, 1H or 2H-tetrazolyl, 2-, 3- or 4-pyridyl, 2-, 4- or 5-pyrimidyl, 3- or 4-pyridazinyl quinolyl, isoquinolyl, indolyl, etc.), which may optionally have 1 to 4 substituents selected from (a) halogen (e.g. bromine, chlorine, fluorine, etc.), (b) $C_{1-4}$ alkyl groups (e.g. methyl, ethyl, propyl, isopropyl, etc.) and (c) halogenophenoxy (e.g. o-, m- or p-chlorophenoxy, o-, m- or p-bromophenoxy, etc.), and (42) $C_{1-10}$ haloalkyl groups (e.g. difluoromethyl, trifluoromethyl, trifluoroethyl, trichloroethyl, etc.), and, in the case where the hydrocarbon group is cycloalkyl, cycloalkenyl, aryl or aralkyl group, 1 to 4 $C_{1-4}$ alkyl groups (e.g. methyl, ethyl, propyl, isopropyl, butyl, etc.) may optionally be further substituted.

With respect to general formula (I), $R^3$ is preferably hydrogen.

With respect to general formula (I), the hydrocarbon residue in the hydrocarbon residue for $R^4$ which is substituted by an optionally protected amino group, is substantially the same as the hydrocarbon residue for $R^3$ which may optionally be substituted. Preferable examples of the hydrocarbon residue include $C_{1-15}$ alkyl groups (e.g. methyl, ethyl, propyl, isopropyl, butyl, isobutyl, sec-butyl, tert-butyl, pentyl, isopentyl, neopentyl, hexyl, heptyl, octyl, nonyl, decyl, undecyl, dodecyl, tridecyl, tetradecyl, pentadecyl, etc.).

With respect to general formula (I), the amino-protecting group in the hydrocarbon residue for $R^4$ which is substituted with an optionally protected amino group is exemplified by (1) formyl, (2) $C_{2-7}$ alkanoyl group (e.g. acetyl, propionyl, isopropionyl, butyryl, valeryl, isovaleryl, pivaloyl, hexanoyl, etc.) optionally having 1 to 3 substituents selected from (a) halogen atoms (e.g. chlorine, bromine, fluorine, etc.), (b) $C_{2-7}$ alkanoyl groups (e.g. acetyl, propionyl, isopropionyl, butyryl, isobutyryl, valeryl, isovaleryl, pivaloyl, hexanoyl, etc.) and (c) nitro group, (3) $C_{7-11}$ arylcarbonyl groups (e.g. benzoyl, p-toluoyl, 1-naphthoyl, 2-naphthoyl, etc.) optionally having 1 to 3 substituents selected from (a) halogen atoms (e.g. chlorine, bromine, fluorine, etc.), (b) $C_{2-7}$ alkanoyl groups (e.g. acetyl, propionyl, isopropionyl, butyryl, isobutyryl, valery, isovalery, pivaloyl, hexanoyl, etc.) and (c) nitro group, (4) $C_{2-7}$ alkoxycarbonyl groups (e.g. methoxycarbonyl, ethoxycarbonyl, propoxycarbonyl, isopropoxycarbony, tert-butoxycarbonyl, etc.) optionally having 1 to 3 substituents selected from (a) halogen atoms (e.g. chlorine, bromine, fluorine, etc.), (b) $C_{2-7}$ alkanoyl groups (e.g. acetyl, propionyl, isopropionyl, butyryl, isobutyryl, valeryl, isovalery, pivaloyl, hexanoyl, etc.) and (c) nitro group, (5) $C_{7-11}$ aryloxycarbonyl groups (e.g. phenoxycarbonyl, etc.) optionally having 1 to 3 substituents selected from (a) halogen atoms (e.g. chlorine, bromine, fluorine, etc.), (b) $C_{2-7}$ alkanoyl groups (e.g. acetyl, propionyl, isopropionyl, butyryl, isobutyryl, valery, isovalery, pivaloyl, hexanoyl, etc.) and (c) nitro group, (6) $C_{8-13}$ aralkylcarbonyl groups (e.g. benzylcarbonyl, phenethylcarbonyl, etc.) optionally having 1 to 3 substituents selected from (a) halogen atoms (e.g. chlorine, bromine, fluorine, etc.), (b) $C_{2-7}$ alkanoyl groups (e.g. acetyl, propionyl, isopropionyl, butyryl, isobutyryl, valeryl, isovaleryl, pivaloyl, hexanoyl, etc.) and (c) nitro group, (7) $C_{8-13}$ aralkyloxycarbonyl groups (e.g. benzyloxycarbonyl, phenethyloxycarbonyl, etc.) optionally having 1 to 3 substituents selected from (a) halogen atoms (e.g. chlorine, bromine, fluorine), (b) $C_{2-7}$ alkanoyl groups (e.g. acetyl, propionyl, isopropionyl, butyryl, isobutyryl, valeryl, pivaloyl, hexanoyl) and (c) nitro group, (8) trityl group optionally having 1 to 3 substituents selected from (a) halogen atoms (e.g. chlorine, bromine, fluorine), (b) $C_{2-7}$ alkanoyl groups (e.g. acetyl, propionyl, isopropionyl, butyryl, valeryl, isovaleryl, pivaloyl, hexanoyl) and (c) nitro group, (9) phthaloyl group optionally having 1 to 3 substituents selected from (a) halogen atoms (e.g. chlorine, bromine, fluorine), (b) $C_{2-7}$ alkanoyl groups (e.g. acetyl, propionyl, isopropionyl, butyryl, isobutyryl, valeryl, isovaleryl, pivaloyl, hexanoyl) and (c) nitro group, (10) $C_{6-10}$ arylsulfonyl groups (e.g. phenylsulfonyl, tosyl) optionally having 1 to 3 substituents selected from (a) halogen atoms (e.g. chlorine, bromine, fluorine), (b) $C_{2-7}$ alkanoyl groups (e.g. acetyl, propionyl, isopropionyl, butyryl, isobutyryl, valeryl, isovalery, pivaloyl, hexanoyl) and (c) nitro group, (11) $C_{1-6}$ alkylsulfonyl groups (e.g. methylsulfonyl, ethylsulfonyl, propylsulfonyl) optionally having 1 to 3 substituents selected from (a) halogen atoms (e.g. chlorine, bromine, fluorine), (b) $C_{2-7}$ alkanoyl groups (e.g. acetyl, propionyl, isopropionyl, butyryl, isobutyryl, valeryl, isovaleryl, pivaloyl, hexanoyl) and (c) nitro group, (12) $C_{1-6}$ alkyl groups (e.g. methyl, ethyl, propyl, isopropyl, butyl, isobutyl, sec-butyl, tert-butyl, pentyl, hexyl) optionally having 1 to 3 substituents selected from (a) halogen atoms (e.g. chlorine, bromine, fluorine), (b) $C_{2-7}$ alkanoyl groups (e.g. acetyl, propionyl, isopropionyl, butyryl, isobutyryl, valeryl, isovaleryl, pivaloyl, hexanoyl) and (c) nitro group, (13) $C_{1-6}$ aminoalkyl groups (e.g. aminomethyl, aminoethyl, 3-aminopropyl, 4-aminobutyl, 5-aminopentyl, 6-aminohexyl) optionally having 1 to 3 substituents selected from (a) halogen atoms (e.g. chlorine, bromine, fluorine), (b) $C_{2-7}$ alkanoyl groups (e.g. acetyl, propionyl, isopropionyl, butyryl, isobutyryl, valeryl, isovaleryl, pivaloyl, hexanoyl) and (c) nitro group, and (14) $C_{7-12}$ aralkyl groups (e.g. benzyl, phenethyl) optionally having 1 to 3 substituents selected from (a) halogen atoms (e.g. chlorine, bromine, fluorine), (b) $C_{2-7}$ alkanoyl groups (e.g. acetyl, propionyl, isopropionyl, butyryl, isobutyryl, valeryl, isovaleryl, pivaloyl, hexanoyl) and (c) nitro group.

With respect to general formula (I), the alkenyl group for $R^4$, is exemplified by $C_{2-10}$ alkenyl groups (e.g. vinyl, allyl, 1-propenyl, 1-, 2- or 3-butenyl, 2-methylallyl, 1-, 2-, 3- or 4-pentenyl, 2- or 3-methyl-2-butenyl, 1-, 2-, 3-, 4- or 5-hexenyl, 1-, 2-, 3-, 4-, 5- or 6-heptenyl, 1-, 2-, 3-, 4-, 5-, 6- or 7-octenyl, 1-, 2-, 3-, 4-, 5-, 6-, 7- or 8-nonenyl, and 1-, 2-, 3-, 4-, 5-, 6-, 7-, 8- or 9-decenyl).

With respect to general formula (I), $R^4$ is preferably a hydrocarbon residue which is substituted by an optionally protected amino group. More preferably, $R^4$ is $CH_{1-15}$ alkyl group (e.g., methyl, ethyl, propyl, isopropyl, butyl, isobutyl, sec-butyl, tert-butyl, pentyl, isopentyl, neopentyl, hexyl, heptyl, octyl, nonyl, decyl, undecyl, dodecyl, tridecyl, tetradecyl, pentadecyl) which is substituted by an optionally protected amino group.

With respect to general formula (I), the heterocyclic group formed by $R^3$ and $R^4$ in combination with the adjacent nitrogen atom, which contains at least 2 hetero atoms, is exemplified by 5- to 8-membered heterocyclic groups containing 1 to 4 hetero atoms selected from oxygen, sulfur, nitrogen etc., in addition to nitrogen atom, or condensed heterocyclic groups thereof. Specifically, such heterocyclic groups include 5-membered heterocyclic groups containing 1 or 3 hetero atoms selected from oxygen, sulfur, nitrogen etc., in addition to nitrogen atom, such as 1,3-diazacyclopentan-1-yl, 1-aza-3-oxacyclopentan-1-yl, 1-aza-3-thiacyclopentan-1-yl, pyrazolyl, pyrazolidinyl, 3-pyrazolin-2-yl, 2-imidazolin-1-yl, 1H- or 2H- 1,2,3-triazolyl, 1H- or 4H-1,2,4-triazolyl and 1H- or 2H-tetrazolyl, 6-membered heterocyclic groups containing 1 or 2 hetero atoms selected from oxygen, sulfur, nitrogen etc., in addition to nitrogen atom, such as thiomorpholino, morpholino piperazinyl, 4H-1,4-oxazinyl and 4H-1,4-thiazinyl and dicyclic or tricyclic condensed heterocyclic groups containing 1 or 2 hetero atoms selected from oxygen, sulfur, nitrogen etc., in addition to nitrogen atom, such as 1H-indazol-1-yl, purin-1-yl, phenothiazin-10-yl and phenoxazin-10-yl.

Of these groups, 5-membered heterocyclic groups containing 1 or 2 hetero atoms selected from oxygen, sulfur, nitrogen etc., in addition to nitrogen atom, such as 1,3-diazacyclopentan-1-yl, 1-aza-3-oxacyclopentan-1-yl, 1-aza-3-thiacyclopentan-1-yl, pyrazolyl, pyrazolidinyl, 3-pyrazolin-2-yl, 2-imidazolin-1-yl, 1H- or 2H- 1,2,3-triazolyl, 1H- or 2H- 1,2,4-triazolyl and 1H- or 2H-tetrazolyl, and 6-membered heterocyclic groups containing 1 or 2 hereto atoms selected from oxygen, sulfur, nitrogen etc., in addition to nitrogen atom, such as thiomorpholino, morpholino piperazinyl, 4H-1,4-oxazinyl and 4H-1,4-thiazinyl are preferred.

More preferably, the heterocyclic group is 6-membered heterocyclic group containing 1 or 2 hetero atoms selected from oxygen, sulfur, nitrogen etc., in addition to nitrogen atom, such as thiomorpholino, morpholino, piperazinyl, 4H-1,4-oxazinyl and 4H-1,4-thiazinyl.

Such heterocyclic groups may have 1 to 5 substituents, at any possible positions, selected from, for example (1) $C_{1-6}$ alkyl groups (e.g. methyl, ethyl, propyl, isopropyl, butyl, isobutyl, sec-butyl, tert-butyl, pentyl, isopentyl, secpentyl, neopentyl, tert-pentyl, hexyl), (2) $C_{2-10}$ alkenyl groups (e.g. vinyl, 1-methylvinyl, 1-propenyl, allyl, 2-methylallyl, 2-butenyl, 3-butenyl, 3-octenyl), (3) $C_{2-10}$ alkynyl groups (e.g. ethynyl, 1-propinyl, propargyl, 3-hexynyl), (4) $C_{3-8}$ cycloalkyl groups (e.g. cyclopropyl, cyclobutyl, cyclopentyl, cyclohexyl), (5) $C_{3-10}$ cycloalkenyl groups (e.g. cyclopropenyl, cyclopentenyl, cyclohexenyl), (6) $C_{7-12}$ aralkyl groups (e.g. benzyl, α-methylbenzyl, phenethyl), (7) $C_{6-10}$ aryl groups (e.g. phenyl, naphthyl), (8) $C_{1-6}$ alkoxy groups (e.g. methoxy, ethoxy, propoxy, isopropoxy, n-butoxy, isobutoxy, sec-butoxy, tert-butoxy), (9) $C_{6-10}$ aryloxy groups (e.g. phenoxy), (10) $C_{7-12}$ aralkyloxy groups (e.g. benzyloxy, a-methylbenzyloxy, phenethyloxy), (11) $C_{1-6}$ alkanoyl groups (e.g. formyl, acetyl, propionyl, isopropionyl, butyryl, isobutyryl, valeryl, isovaleryl, pivaloyl, hexanoyl), (12) $C_{7-11}$ arylcarbonyl groups (e.g. benzoyl, p-toluoyl, 1-naphthoyl, 2-napthoyl), (13) $C_{8-13}$ aralkylcarbonyl groups (e.g. benzylcarbonyl, a-methylbenzylcarbonyl, phenethylcarbonyl), (14) $C_{1-6}$ alkanoyloxy groups (e.g. formyloxy, acetyloxy, propionyloxy, isopropionyloxy, butyryloxy, isobutyryloxy, valeryloxy, isovaleryloxy, pivaloyloxy, hexanoyloxy), (15) $C_{7-11}$ arylcarbonyloxy groups (e.g. benzoyloxy, p-toluoyloxy, 1-naphthoyloxy, 2-naphthoyloxy), (16) carboxyl group, (17) $C_{2-7}$ alkoxycarbonyl groups (e.g. methoxycarbonyl, ethoxycarbonyl, n-propoxycarbonyl, isopropoxycarbonyl, n-butoxycarbonyl, isobutoxycarbonyl, tert-butoxycarbonyl), (18) $C_{8-13}$ aralkyloxycarbonyl groups (e.g. benzyloxycarbonyl, phenethyloxycarbonyl), (19) $C_{7-11}$ aryloxycarbonyl groups (e.g. phenoxycarbonyl), (20) carbamoyl group, (21) N-mono-$C_{1-4}$ alkylcarbamoyl groups (e.g. N-methylcarbamoyl, N-ethylcarbamoyl, N-propylcarbamoyl, N-isopropylcarbamoyl, N-butylcarbamoyl), (22) N,N-di-$C_{1-4}$ alkylcarbamoyl groups (e.g. N,N-dimethylcarbamoyl, N,N-diethylcarbamoyl, N,N-dipropylcarbamoyl, N,N-dibutylcarbamoyl), (23) cyclic aminocarbonyl groups (e.g. 1-aziridinylcarbonyl, 1-azetidinylcarbonyl, 1-pyrrolidinylcarbonyl, 1-piperidinylcarbonyl, N-methylpiperazinylcarbonyl, morpholinocarbonyl), (24) halogen atoms (e.g. fluorine, chlorine, bromine, iodine), (25) mono-, di- or tri-halogeno-$C_{1-4}$ alkyl groups (e.g. chloromethyl, dichloromethyl, trifluoromethyl, trifluoroethyl), (26) oxo group, (27) thioxo group, (28) amidino group, (29) imino group, (30) amino group, (31) mono-$C_{1-4}$ alkylamino groups (e.g. methylamino, ethylamino, propylamino, isopropylamino, butylamino), (32) di-$C_{1-4}$ alkylamino groups (e.g. dimethylamino, diethylamino, dipropylamino, diisopropylamino, dibutylamino), (33) 3- to 6-roeinhered cyclic amino groups optionally containing 1 to 3 hetero-atoms selected from e.g. oxygen atom, sulfur atom and nitrogen atom, in addition to carbon atoms and one nitrogen atom (e.g. aziridinyl, azetidinyl, pyrrolidinyl, pyrrolinyl, pyrrolyl, imidazolyl, pyrazolyl, imidazolidinyl, piperidino, morpholino, dihydropyridyl, pyridyl, N-methylpiperazinyl, N-ethylpiperazinyl), (34) $C_{1-6}$ alkanoylamino groups (e.g. formylamino, acetylamino, trifluoroacetylamino, propionylamino, butyrylamino, isobutyrylamino), (35) $C_{7-11}$ arylcarbonylamino groups (e.g. benzoylamino, p-toluoylamino, 1-naphthoylamino, 2-naphthoylamino), (36) $C_{2-7}$ alkoxycarbonylamino groups (e.g. methoxycarbonylamino, ethoxycarbonylamino, tert-butoxycarbonylamino), (37) $C_{8-13}$ aralkyloxycarbonylamino groups (e.g. benzyloxycarbonylamino, phenethyloxycarbonylamino), (38) $C_{1-6}$ alkylsulfonylamino groups (e.g. methylsulfonylamino, ethylsulfonylamino, propylsulfonylamino), (39) $C_{6-12}$ arylsulfonylamino groups (e.g. phenylsulfonylamino, tosylamino), (40) carbamoylamino group, (41) N-$C_{1-4}$ alkylcarbamoylamino groups (e.g. N-methylcarbamoylamino, N-ethylcarbamoylamino, N-propylcarbamoylamino, N-isopropylcarbamoylamino, N-butylcarbamoylamino), (42) N,N-di-$C_{1-4}$ alkylcarbamoylamino groups (e.g. N,N-dimethylcarbamoylamino, N,N-diethylcarbamoylamino, N,N-dipropylcarbamoylamino, N,N-dibutylcarbamoylamino), (43) $C_{1-3}$ alkylenedioxy groups (e.g. methylenedioxy, ethylenedioxy), (44)-B(OH)$_2$, (45) hydroxy group, (46) epoxy (—O—), (47) nitro group, (48) cyano group, (49) mercapto group, (50) sulfo group, (51) sulfino group, (52) phosphono group, (53) sulfamoyl group, (54) $C_{1-6}$ monoalkylsulfamoyl groups (e.g. N-methylsulfamoyl, N-ethylsulfamoyl, N-propylsulfamoyl, N-isopropylsulfamoyl, N-butylsulfamoyl), (55) di-$C_{1-4}$ alkylsulfamoyl groups (e.g. N,N-dimethylsulfamoyl, N,N-diethylsulfamoyl, N,N-dipropylsulfamoyl, N,N-dibutylsulfamoyl), (56) $C_{1-6}$ alkylthio groups (e.g. methylthio, ethylthio, propylthio, isopropylthio, n-butylthio, sec-butylthio, tert-butylthio), (57) $C_{6-10}$ arylthio groups (e.g. phenylthio, naphthylthio), (58) $C_{1-6}$ alkylsulfinyl groups (e.g. methylsulfinyl, ethylsulfinyl, propylsulfinyl, butylsulfinyl), (59) $C_{6-10}$ arylsulfinyl groups (e.g. phenylsulfinyl), (60) $C_{1-6}$ alkylsulfonyl groups (e.g. methylsulfonyl, ethylsulfonyl, propylsulfonyl, butylsulfonyl) and (61) $C_{6-10}$ arylsulfonyl groups (e.g. phenylsulfonyl, tosyl).

With respect to general formula (I), $R^3$ and $R^4$ are preferably combined with the adjacent nitrogen atom to form a heterocyclic group containing at least two hetero atoms. The heterocyclic group is preferably 6-membered heterocyclic group containing 1 or 2 hetero atoms selected from oxygen, sulfur, nitrogen etc., in addition to nitrogen atom, such as thiomorpholino, morpholino, piperazinyl, 4H-1,4-oxazinyl and 4H-1,4-thiazinyl.

The preferred examples of compound (I) or a salts thereof include
N-[N-[(2S,3S)-3-trans-carboxyoxirane-2-carbonyl]-L-phenylalanyl]-1,4-diaminobutane,
N-[N-[(2S,3S)-3-trans-ethoxycarbonyloxirane-2-carbonyl]-L-phenylalanyl]-1,4-diaminobutane,
N-[N-[(2S,3S)-3-trans-ethoxycarbonyloxirane- 2-carbonyl]-L-phenylalanyl]morpholine,
N-[N-[(2S,3S)-3-trans-carboxyoxirane-2-carbonyl]-L-phenylalanyl]morpholine,
N-[N-[(2S,3S)-3-trans-ethoxycarbonyloxirane-2-carbonyl]-L-tyrosyl]morpholine,
N-[N-[(2S,3S)-3-trans-carboxyoxirane-2-carbonyl]-L-tyrosyl]morpholine,
N-[N-[(2S,3S)-3-trans-ethoxycarbonyloxirane-2-carbonyl]-3-(2-naphtyl)-L-alanyl]morpholine,
N-[N-[(2S,3S)-3-trans-carboxyoxirane-2-carbonyl]-3-(2-naphtyl)-L-alanyl]morpholine, or salts thereof.

In the general formula (XI), the carboxyl group for $R^{11}$ which may optionally be esterified or amidated, is substantially the same as that represented by $R^1$ in the general formula (I) described above.

In the general formula (XI), the aromatic polycyclic group represented by $R^{12}$ is preferably $C_{8-18}$ aromatic polycyclic groups. More specifically, these groups are exemplified by $C_{8-12}$ dicyclic aromatic groups such as 1-, 2- or 3-pentalenyl, 1- or 2-naphthyl, 1-, 2-, 4-, 5- or 6-azulenyl, quinolyl, isoquinolyl and indolyl, and $C_{12-18}$ tricyclic aromatic groups such as 1-, 2- or 9-anthryl, 1-, 2-, 3-, 4- or 9-phenanthryl. More preferable aromatic polyclic groups are exemplified by $C_{8-12}$ dicyclic aromatic groups such as 1-, 2- or 3-pentalenyl, 1- or 2-naphthyl, 1-, 2-, 4-, 5- or 6-azulenyl, quinolyl, isoquinolyl and indolyl.

These aromatic polycyclic groups may optionally have, at any possible positions, 1 to 5 substituents. The substituents are substantially the same as that defined in the cyclic groups represented by $R^2$ in the general formula (I).

With respect to the general formula (XI), examples of alkyl groups represented by $R^{13}$ and $R^{14}$ include $C_{1-15}$ alkyl groups (e.g. methyl, ethyl, propyl, isopropyl, butyl, isobutyl, sec-butyl, tert-butyl, pentyl, isopentyl, hexyl, heptyl, octyl, nonyl, decyl, undecyl, dodecyl, tridecyl, tetradecyl and pentadecyl).

The preferred examples of compound (XI) or a salts thereof include
N-[N-[(2S,3S)-3-trans-ethoxyearbonyloxirane-2-carbonyl]-3-(2-naphthyl)-L-alanyl]-1-amino-3-methylbutane,
N-[N-[(2S,3S)-3-trans-carboxyoxirane-2-carbonyl]-3-(2-naphtyl)-L-alanyl]-1-amino-3-methylbutane, or salts thereof.

In the general formula (XXI), the carboxyl group for $R^{21}$ which may optionally be esterified or amidated, is substantially the same as that represented by $R^1$ in the general formula (I) described above.

In the general formula (XXI), the alkyl group for $R^{22}$, is exemplified by $C_{1-15}$ alkyl groups such as methyl, ethyl, propyl, isopropyl, butyl, isobutyl, see-butyl, tert-butyl, pentyl, isopentyl, neo-pentyl, hexyl, heptyl, octyl, nonyl, decyl, undecyl, dodecyl, tridecyl, tetradecyl and pentadecyl. Of these alkyl groups, $C_{2-10}$ alkyl groups are preferred, with greater preference given to $C_{3-5}$ alkyl groups.

In the general formula (XXI), the amino protecting group in the alkyl group for $R^{23}$ and $R^{24}$ which is substituted by an optionally protected amino group is, exemplified by (1) formyl, (2) $C_{2-7}$ alkanoyl groups such as acetyl, propionyl, butyryl and valeryl, which may have 1 to 3 substituents selected from (a) halogen atoms (e.g., chlorine, bromine, fluorine), (b) $C_{2-7}$ alkanoyl groups (e.g., acetyl, propionyl, butyryl, valeryl) and (e) nitro group, (3) $C_{7-11}$ arylcarbonyl groups such as phenylcarbonyl, which may have 1 to 3 substituents selected from (a) halogen atoms (e.g., chlorine, bromine, fluorine), (b) $C_{2-7}$ alkanoyl groups (e.g., acetyl, propionyl, butyryl, valeryl) and (c) nitro group, (4) $C_{1-6}$ alkoxycarbonyl groups such as methoxycarbonyl and ethoxycarbonyl, which may have 1 to 3 substituents selected from (a) halogen atoms (e.g., chlorine, bromine, fluorine), (b) $C_{2-7}$ alkanoyl groups (e.g., acetyl, propionyl, butyryl, valeryl) and (c) nitro group, (5) $C_{7-11}$ aryloxycarbonyl groups such as phenoxycarbonyl, which may have 1 to 3 substituents selected from (a) halogen atoms (e.g., chlorine, bromine, fluorine), (b) $C_{2-7}$ alkanoyl groups (e.g., acetyl, propionyl, butyryl, valeryl) and (c) nitro group, (6) $C_{8-13}$ aralkylcarbonyl groups such as benzylcarbonyl and phenylethylcarbonyl, which may have 1 to 3 substituents selected from (a) halogen atoms (e.g., chlorine, bromine, fluorine), (b) $C_{2-7}$ alkanoyl groups (e.g., acetyl, propionyl, butyryl, valeryl) and (c) nitro group, (7) $C_{7-11}$ arylcarbonyl groups such as phenylcarbonyl, which may have 1 to 3 substituents selected from (a) halogen atoms (e.g., chlorine, bromine, fluorine), (b) $C_{2-7}$ alkanoyl groups (e.g., acetyl, propionyl, butyryl, valeryl) and (c) nitro group, (8) $C_{7-12}$ aralkyloxycarbonyl groups such as benzyloxycarbonyl and phenylethyloxycarbonyl, which may have 1 to 3 substituents selected from (a) halogen atoms (e.g., chlorine, bromine, fluorine), (b) $C_{2-7}$ alkanoyl groups (e.g., acetyl, propionyl, butyryl, valeryl) and (c) nitro group, (9) trityl groups which may have 1 to 3 substituents selected from (a) halogen atoms (e.g., chlorine, bromine, fluorine), (b) $C_{2-7}$ alkanoyl groups (e.g., acetyl, propionyl, butyryl, valeryl) and (c) nitro group, (10) phthaloyl groups which may have 1 to 3 substituents selected from (a) halogen atoms (e.g., chlorine, bromine, fluorine), (b) $C_{2-7}$ alkanoyl groups (e.g., acetyl, propionyl, butyryl, valeryl) and (c) nitro group, and (11) $C_{6-10}$ arylsulfonyl groups such as phenylsulfonyl, which may have 1 to 3 substituents selected from (a) halogen atoms (e.g., chlorine, bromine, fluorine), (b) $C_{2-7}$ alkanoyl groups (e.g., acetyl, propionyl, butyryl, valeryl) and (c) nitro group.

Preferably, $R^{23}$ and $R^{24}$ are alkyl groups substituted by an amino group which may optionally be protected by $C_{8-13}$ aralkyloxycarbonyl group such as benzyloxycarbonyl or phenethyloxycarbonyl, which may have 1 to 3 substituents selected from halogen atoms (e.g., chlorine, bromine, fluorine), $C_{2-7}$ alkanoyl groups (e.g., acetyl, propionyl, butyryl, valeryl) and nitro group, with greater preference given to aminoalkyl groups.

Such alkyl groups include $C_{1-15}$ alkyl groups such as methyl, ethyl, propyl, isopropyl, butyl, isobutyl, sec-butyl, tert-butyl, pentyl, isopentyl, neopentyl, hexyl, heptyl, octyl, nonyl, decyl, undecyl, dodecyl, tridecyl, tetradecyl and pentadecyl. Of these alkyl groups, $C_{1-10}$ alkyl groups are preferred, with greater preference given to $C_{1-6}$ alkyl groups.

Any microorganism can be used to produce TAN-1756A, B, C and/or D, a compound of the present invention, as long as it belongs to the genus *Chaetomium* and is capable of producing TAN-1756A, B, C and/or D. Such microorganisms include FL-41927, a mold strain newly isolated from soil of Osaka Prefecture, Japan. This strain is characterized as follows:

a) Morphology

The strain FL-41927 grows well, forming a perithelium, in malt extract agar medium, potato-glucose agar medium, oat meal agar medium etc. The perithelium, superficial, dark olive-brown and semi-spherical to ovate, has a top pore and a size of 65–75 μm×95–105 μm. The petithelium has a large number of dense olive-brown top hairs in a strangled mass. The top hair has a septal wall and a width of 2.5–3.0 μm, with a wavy curve from the base or with a gentle coil, lacking branching. The light olive-brown side hairs are straight or slightly wavy, unifying with the top hairs at the top of the perithelium. The ascus is clayate, having 8 spores. The ascospores (7–9 μm×10–12 μm) are olive-brown and lemon-shaped, with slightly pinnate ends.

b) Properties on Agar Medium (1) Malt extract agar medium: Growth at 24° C. is good; colony diameter reaches 78–83 mm 2 weeks later. Surface comprises thin wool-like mycelia; a mass of blackish grey spots appears in the central portion; radial thin expansion is seen from the intermediate portion to the periphery. Outer margin is regular. Development of aerial mycelia is good; black ascocarps are formed around the 10th day, forming a central mass 2 weeks later. Blackish grey to grayish white from the center to the intermediate portion, the periphery having a cream color. The center to periphery of the back face is light blackish grey to light grey, the periphery being ivory. No soluble pigments are formed.

(2) Potato-glucose agar medium: Growth at 24° C. is good; colony diameter reaches 55–60 mm 2 weeks later. Surface comprises slightly risen wool-like mycelia, with a central hollow and radially thinly expands from the intermediate portion to the periphery. Outer margin is regular. Aerial mycelial development is very good; black ascocarps are formed around the 10th day, expanding all over the colony 2 weeks later. The central portion is dark blackish grey, the intermediate portion light blackish grey, and the periphery is light grey. From the center to the intermediate portion of the back face, light blackish grey to light grey, and the periphery is ivory. No soluble pigments are formed.

(3) Czapek agar medium: Growth at 24° C. is slow and poor; colony diameter reaches 40–50 mm 2 weeks later. Surface is flat, comprising thin wool-like mycelia, with irregular sinnate outer margin. Development of aerial mycelia is poor; no ascarps are formed. Generally white to yellowish white. Back face is light yellow-brown to yellow-brown. No soluble pigments are formed.

c) Physiological Properties

Growth conditions for this strain were examined using potato-glucose agar medium. The growth temperature range is 10°–36° C., the optimum temperature being 18°–28° C. Good growth was seen over the pH range 4–12.

On the basis of these findings, mainly the morphological characters, and with reference to "Separation, Cultivation and Identification of Fungi" (by D. Malloch, translated into Japanese by S. Udagawa, 1983, Ishiyaku Publishers), Kinrui Zukan (Jyo) (by S. Udagawa, K. Tsubaki et al., 1978, Kodansha Scientific) and "The Ascomycete Genus Chaetomium" (by J. A. von Arx, J. Gunfro and M. J. Figueras, 1986, J. Cramer Publisher), this strain was identified as *Chaetomium globosum* FL-41927 strain.

This strain has been deposited under accession number IFO 32580 at the Institute for Fermentation, Osaka (IFO) since Aug. 17, 1993, and under accession number FERM BP-4443 at the National Institute of Bioscience and Human-Technology (NIBH), Agency of Industrial Science and Technology, Ministry of International Trade and Industry, since Oct. 18, 1993.

Any microorganism can be used to produce TAN-1854A and/or B, a compound of the present invention, as long as it belongs to the genus *Tolypocladium* and is capable of producing TAN-1854A and/or B. Such microorganisms include FL-43974, a mold strain newly isolated from soil of Nara Prefecture, Japan.

This strain is characterized as follows:

a) Morphology

The strain FL-43974 grows well, forming many conidia, in malt extract agar medium, potato-glucose agar medium, oat meal agar medium etc. The mycelium has a septal wall, with irregularly branched conidiophores from aerial mycelia. Bottle-shaped phialides (0.3–1.6 μm×5.0–8.0 μm) with a tapered top end are mononematous or verticillate (2 to 3 phialides). Conidia are not linked together, cylindrical, 2.1–2.3 μm×2.6–2.8 μm in size, with a smooth surface, forming a conidial mass at top end of phialide.

b) Properties on Agar Medium (1) Malt extract agar medium: Growth at 24° C. is moderate, with slow limited colony expansion; colony diameter reaches 35 mm 2 weeks later. Central surface comprises risen wool-like mycelia, with a regular outer margin. Center to periphery are white to cream. Intermediate portion and outer periphery are white. Back face is light yellow. No soluble pigments are formed.

(2) Potato-glucose agar medium: Growth at 24° C. is moderate, with limited colony expansion; colony diameter reaches 35–37 mm 2 weeks later. Surface comprises slightly risen wool-like mycelia, with a regular outer margin. Center to periphery are light grayish white to light grayish yellow. Back face is light yellow-brown. No soluble pigments are formed.

(3) Czapek agar medium: Growth at 24° C. is poor; colony diameter reaches 25 mm 2 weeks later. Surface is flat, comprising thin wool-like mycelia from center to periphery. Outer margin is somewhat irregular. Surface center to periphery are light grayish white. Center to periphery on back face are ivory to cream in color. No soluble pigments are formed.

c) Physiological Properties

Growth conditions for this strain were examined using potato-glucose agar medium. The growth temperature range is 6°–33° C., the optimum temperature being 18°–24° C. Good growth was obtained over the pH range 3–12.

On the basis of these findings and with reference to "The Genera of Fungi Sporulating in Pure Culture" by J. A. Von Arx, 1981, J. Cramer Company and "Canadian Journal of Botany," Vol. 61, p. 1331 (1983), J. Bissett, and Notes on Tolypocladium and Related Genera, this strain was identified as *Tolypocladium cylindrosporum* FL-43974 strain.

This strain has been deposited under accession number IFO 32582 at the Institute for Fermentation, Osaka (IFO) since Aug. 17, 1993, and under accession number FERM BP-4445 at the National Institute of Bioscience and Human-Technology (NIBH), Agency of Industrial Science and Technology, Ministry of International Trade and Industry, since Oct. 18, 1993.

Like other molds, the TAN-1756A, B, C and/or D producer fungi belonging to the genus *Chaetomium* and the TAN-1854A and/or B producer fungi belonging to the genus *Tolypocladium* can be mutated by various means of mutation such as irradiation with ultraviolet rays, radioactive rays etc., single cell separation and various chemical mutagens. Any artificial mutant as such or, even naturally-occurring mutant, can be used in the method of the present invention, as long as it is substantially identical with one of the above-described strains as compared on the basis of the above taxonomic characters, and as long as it is capable of producing the relevant compound.

The medium used to culture a TAN-1756A, B, C and/or D producer fungus or a TAN-1854A and/or B producer fungus may be liquid or solid, as long as it contains the nutrient sources available thereby. In the case of large-scale cultivation, it is preferable to use a liquid medium. The medium is supplemented with carbon sources, nitrogen sources, inorganic substances and trace nutrients assimilable by the producer fungus as appropriate. Carbon sources include glucose, lactose, sucrose, maltose, dextrin, starch, glycerol, mannitol, sorbitol, oils and fats (e.g., soybean oil, lard oil, chicken oil) and n-paraffin. Nitrogen sources include meat extract, yeast extract, dry yeast, soybean flour, corn steep liquor, peptone, cottonseed flour, blackstrap molasses, urea and ammonium salts (e.g., ammonium sulfate, ammonium chloride, ammonium nitrate, ammonium acetate). Salts of metals such as sodium, potassium, calcium, magnesium, iron, manganese, zinc, cobalt and nickel, salts of inorganic acids such as phosphoric acid and boric acid, and salts of organic acids such as acetic acid and propionic acid, are used as appropriate. The medium may also incorporate amino acids (e.g., glutamic acid, aspartic acid, alanine, lysine, methionine, proline), peptides (e.g., dipeptides, tripeptides), vitamins (e.g., $B_1$, $B_2$, nicotinic acid, $B_{12}$, C) and nucleic acids (e.g., purine, pyridine, derivatives thereof). It is also possible to add inorganic acids, organic acids, alkalis, buffers and other additives may be added to regulate the pH of the medium. Appropriate amounts of oils and fats, surfactants and other additives may be added for the purpose of defoaming. In liquid culture, nearly neutral pH levels are preferred, with particular preference given to the pH range 5.5–8.

Culturing temperature is preferably about 24°–30° C. Culturing time is preferably 48 to 168 hours.

To collect the desired compound TAN-1756A, B, C and/or D or TAN-1854A and/or B from the culture, there may be used as appropriate a means in common use to collect microbial metabolites from a culture of the microorganism. For example, TAN-1756A, B, C and D and TAN-1854A and B, both water-soluble amphoteric substances, are contained mainly in the culture flitrate; it is advantageous to first filter the culture broth in the presence of a filter aid, or centrifuge, to remove cells, then bring the resulting culture flitrate into contact with an appropriate carrier to adsorb the active ingredient in the flitrate to the carrier, desorb the active ingredient with an appropriate solvent and separately collect it. Useful chromatographic carriers include carriers based on compound adsorptivity differences, such as activated charcoal, silica gel, microcrystalline cellulose and adsorptive resin, those based on functional group differences, such as ion exchange resin, ion exchange cellulose and ion exchange Sephadex, and those based on molecular weight differences, such as molecular sieve carriers. To elute the desired compound from these carriers, there may be used mixed solvents in an appropriate ratio, e.g., water-miscible organic solvents (e.g., methanol, ethanol, acetone, acetonitrile), water, aqueous dilute alkalis (e.g., sodium hydroxide, potassium hydroxide, sodium hydrogen carbonate), aqueous dilute acids (e.g., hydrochloric acid, acetic acid, formic acid, phosphoric acid), and buffers (e.g., acetate buffers, phosphate buffers), the combination depending on kind and nature of the carrier.

More specifically, when using a cation exchange resin such as Amberlite IR-120, IRC-50 (produced by Rohm & Haas, USA), Dowex 50W (produced by Dow Chemical, USA) or Diaion SK1A (produced by Mitsubishi Chemical Industries) or an anion exchange resin such as Amberlite IRA-402, IRA-68 (produced by Rohm & Haas, USA), Dowex 1 (produced by Dow Chemical, USA) or Diaion SA10B, PA-404 or WA-30 (produced by Mitsubishi Chemical Industries), the desired compound is adsorbed from the flitrate and eluted with an aqueous solution or buffer containing a salt, alkali or acid. The desired compound can also be adsorbed to an ion exchange molecular sieve resin carrier such as QAE or CM-Sephadex (produced by Pharmacia, Sweden) and eluted with an aqueous solution or buffer containing a salt, alkali or acid. To remove the salts, coloring substances etc. from these eluates, there may be advantageously used activated carbon for chromatography (produced by Takeda Chemical Industries), an adsorptive resin such as Diaion HP-20 or SP-207 (produced by Mitsubishi Chemical Industries), Amberlite XAD-1 or II (produced by Rohm & Haas, USA), a molecular sieve resin such as Sephadex LH-20 (produced by Pharmacia, Sweden), or a microcrystalline cellulose such as Avicel (produced by Asahi Chemical) or Funacel (produced by Funakoshi Pharmaceutical).

In the final purification process for the desired compound, preparative high performance liquid chromatography (HPLC) is advantageously used. When this method is used, octadecylsilane (ODS) carriers, aminopropylsilane carriers, polyamine carriers and silica gel carriers are advantageously used. In the case of ODS, YMC gel (produced by Yamamura Kagaku Kenkyujo) or TSK gel (produced by Toyo Soda Manufacturing) or the like is used, with a mixed solution of methanol or acetonitrile and water or a salt-containing aqueous solution used advantageously as a mobile phase.

Since TAN-1756A, B, C and D and TAN-1854A and B are both amphoteric substances, they can be obtained as alkali metal salts such as sodium salt and potassium salt, alkaline earth metal salts such as calcium salt and magnesium salt, or acid-addition salts, particularly pharmacologically acceptable acid-addition salts, by a per se known methods. Such salts include salts formed with inorganic acids (e.g., hydrochloric acid, sulfuric acid, phosphoric acid) or organic acids (e.g., acetic acid, propionic acid, citric acid, tartaric acid, malic acid, oxalic acid, methanesulfonic acid, octanesulfonic acid).

Any microorganism can be used to produce TAN-1803, a compound of the present invention, as long as it belongs to the genus *Trichoderma* and is capable of producing TAN-1803. Such microorganisms include FL-42547, a mold strain newly isolated from soil of India.

This strain is characterized as follows:

a) Morphology

The strain FL-42547 grows well, forming many conidia, in malt extract agar medium, potato-glucose agar medium, oat meal agar medium etc. The mycelium has a septal wall; long conidiophores, mononematous or verticillate, extend vertically or irregularly from aerial mycelia, lacking abortive mycelia. There are 3 to 5 verticillate bottle-shaped phialides (2.5–3.0 μm×5.0–6.0 μm). Conidia are not linked together, obovate, with a cut end, 2.1–2.3 μm×2.6–2.8 μm in size, with a smooth surface.

b) Properties on Agar Medium (1) Malt extract agar medium: Growth at 24° C. is good; colony diameter reaches over 90 mm 2 weeks later. Surface is flat, with thin wool-like aerial mycelia. Outer margin is regular. Conidia form well, expanding verticillately to form a ring pattern; color turns from dark green to dark blue-green with the formation of conidia. Back face center to periphery is light yellow-green to light yellowish grey. No soluble pigments are formed.

(2) Potato-glucose agar medium: Growth at 24° C. is good; colony diameter reaches over 90 mm 2 weeks later. Surface is flat, with thin wool-like aerial mycelia. Outer margin is regular. Conidia form well, expanding verticillately to form a ring pattern; color turns from light green to dark green with the formation of conidia. Back face center to periphery is light yellow-green to light yellowish grey. No soluble pigments are formed.

(3) Czapek agar medium: Growth at 24° C. is good; colony diameter reaches over 90 mm 2 weeks later. Outer margin is regular. Thin aerobic mycelia expand radially. Formation of conidia is moderate. Center to periphery is grayish-white to gray. Back face is light gray to ivory. No soluble pigments are formed.

c) Physiological Properties

Growth conditions for this strain were examined using potato-glucose agar medium. The growth temperature range is 12°–36° C., the optimum temperature being 19°–23° C. Although the strain grows over the pH range 3–12, its growth was poor at pH 9 and higher.

On the basis of these findings and with reference to *Separation, Cultivation and Identification of Fungi* (by D. Malloch, translated into Japanese by S. Udagawa, 1983, Ishiyaku Publishers) and *A Revision of the Genus Trichoderma* (M. A. Rifai, 1986, Commonwealth Mycological Institute, Kew, Surrey, England), this strain was identified as *Trichoderma aureoviride* FL-42547 strain.

This strain has been deposited under accession number IFO 32581 at the Institute for Fermentation, Osaka (IFO) since Aug. 17, 1993, and under accession number FERM BP-4444 at the National Institute of Bioscience and Human-Technology (NIBH), Agency of Industrial Science and Technology, Ministry of International Trade and Industry, since Oct. 18, 1993.

Any microorganism can be used to produce TAN-1868, a compound of the present invention, as long as it belongs to the genus *Aspergillus* and is capable of producing TAN-1868. Such microorganisms include FL-47958, a mold strain newly isolated from soil of Osaka Prefecture, Japan.

This strain is characterized as follows:

a) Morphology

The strain FL-47958 grows well in malt extract agar medium, potato-glucose agar medium, oat meal agar medium etc. The mycelium has a septal wall; conidiophores are formed on aerial mycelia. The conidiophore is slightly curved, 80–160 μm in length, with a smooth surface. Its top end thickens to form a vesicle. The vesicle is semi-spherical and 15–20 μm in diameter, with metulae in the upper half. The metula is cylindrical and 3.5–4.5 μm×1.5–2.0 μm in size, having 2 to 4 bottle-shape$_d$ fascicled phialides (5–6 μm×1.0–2.0 μm) with a smooth surface thereon. Conidia (2.0–2.5 μm×1.0–2.0 μm) are spherical to semi-spherical, linked together, with a smooth surface.

b) Properties on Agar Medium (1) Malt extract agar medium: Growth at 24° C. is moderate, with limitative colony expansion; colony diameter reaches 35 mm 2 weeks later. Surface is flat; colony comprises velvety mycelia with a slightly risen center. Outer margin is regular. Development of aerial mycelia is good, while formation of conidia is poor. Center to periphery is light grayish white to light yellowish white. Back face center to periphery is dark yellow-brown to light yellow-brown. No soluble pigments are formed.

(2) Potato-glucose agar medium: Growth at 24° C. is moderate, with limitative colony expansion; colony diameter reaches 33 mm 2 weeks later. Surface is flat; colony comprises velvety mycelia with a slightly risen center. Outer margin is slightly irregular. Development of aerial mycelia is good, while formation of conidia is poor. Center to intermediate portion is light grayish white, and periphery is white. Back face center is dark red-brown to red-brown, intermediate portion is dark red-brown, and periphery is light yellow-brown. No soluble pigments are formed.

(3) Oat meal agar medium: Growth at 24° C. is moderate; colony diameter reaches 30 mm 2 weeks later. Surface comprises slightly risen powdery to velvety mycelia with a slightly sunken center and a thin periphery. Outer margin is regular. Development of aerial mycelia and formation of conidia are good. Center is yellow-brown with slightly grayish white streaks, intermediate portion is light yellow-brown in a ring pattern, intermediate portion to periphery is cream to light grayish white. Back face center is light yellow-brown to cream, intermediate portion to periphery is light yellow-brown to ivory. No soluble pigments are formed.

c) Physiological Properties

Growth conditions for this strain were examined using potato-glucose agar medium. The growth temperature range is 12°–37° C., the optimum temperature being 23°–29° C. The strain grows well over the pH range 3–12. On the basis of these findings and with reference to *Separation, Cultivation and Identification of Fungi* (by D. Malloch, translated into Japanese by S. Udagawa, 1983, Ishiyaku Publishers), this strain was identified as belonging to the genus *Aspergillus*, and designated as *Aspergillus* sp. FL-47958 strain.

This strain has been deposited under accession number IFO 32583 at the Institute for Fermentation, Osaka (IFO) since Aug. 17, 1993, and under accession number FERM BP-4446 at the National Institute of Bioscience and Human-Technology (NIBH), Agency of Industrial Science and Technology, Ministry of International Trade and Industry, since Oct. 18, 1993.

Like other molds, the TAN-1803 producer fungi belonging to the genus *Trichoderma* and the TAN-1868 producer fungi belonging to the genus *Aspergillus* can be mutated by various means of mutation such as irradiation with ultraviolet rays, radioactive rays etc., single cell separation and various chemical mutagens. Any artificial mutant as such or, even naturally-occurring mutant, can be used in the method of the present invention, as long as it is substantially identical with one of the above-described strains as compared on the basis of the above taxonomic characters, and as long as it is capable of producing the relevant compound.

The medium used to culture a TAN-1803 producer fungus or a TAN-1868 producer fungus is substantially the same as that used to culture a TAN-1756 A, B, C and/or D producer fungus or a TAN-1854 A and/or B producer fungus.

To collect the desired compound TAN-1803 or TAN-1868 from the culture, there may be used as appropriate a means in common use to collect microbial metabolites from a culture of the microorganism. TAN-1803, a water-soluble amphoteric substance, and TAN-1868, a water-soluble acidic substance, are collected in substantially the same manner as that in the case of TAN-1756 A, B, C and/or D and TAN-1854 A and/or B.

Since TAN-1803 is an amphoteric substance, it can be obtained as an alkali metal salt such as sodium salt or potassium salt, an alkaline earth metal salt such as calcium salt or magnesium salt, or an acid-addition salt, particularly a pharmacologically acceptable acid-addition salt, by a per se known method. Such salts include salts formed with inorganic acids (e.g., hydrochloric acid, sulfuric acid, phosphoric acid) or organic acids (e.g., acetic acid, propionic acid, citric acid, tartaric acid, malic acid, oxalic acid, methanesulfonic acid). Since TAN-1868 is an acidic substance, it can be obtained as an alkali metal salt such as sodium salt or potassium salt, or an alkaline earth metal salt such as calcium salt or magnesium salt by a per se known method.

A method of producing compound (I) above or a salt thereof is hereinafter described.

Protecting groups and reagents often mentioned herein are abbreviated as follows:

| | |
|---|---|
| Fmoc: | 9-fluorenylmethyloxycarbonyl |
| Z: | Benzyloxycarbonyl |
| Boc: | tert-butoxycarbonyl |
| Bzl: | Benzyl |
| Ph: | Phenyl |
| Trt: | Trityl |
| But: | Butyryl |
| Ts: | p-toluenesulfolyl |
| TFA: | Trifluoroacetic acid |
| Tos: | p-toluenesulfonic acid |
| DCC: | N,N'-dicyclohexylcarbodiimide |
| BOP: | Benzotriazol-1-yloxytris(dimethylamino)phosphonium hexafluorophosphate |
| DIC: | N,N'-diisopropylcarbodiimide |
| HONB: | N-hydroxy-5-norbornane-2,3-dicarboxyimide |
| HOBT: | 1-hydroxybenzotriazole |
| WSC: | Water-soluble carbodiimide [1-ethyl-3-(3-dimethylaminopropyl)carbodiimide hydrochloride] |
| R-: | R-configuration |
| S-: | S-configuration |

A compound represented by general formula (I) above or a salt thereof can be produced by reacting a compound represented by the general formula:

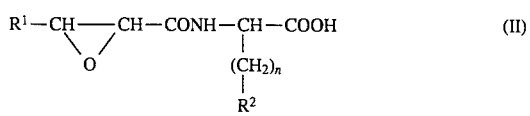

wherein $R^1$, $R^2$ and n have the same definitions as above, or a salt thereof, with a compound represented by the general formula:

wherein $R^3$ and $R^4$ have the same definitions as above, or a salt thereof, followed by a deprotection reaction if necessary, or by reacting a compound represented by the general formula:

wherein $R^1$ has the same definition as above, or a salt thereof, with a compound represented by the general formula:

wherein $R^2$, $R^3$, $R^4$ and n have the same definitions as above, or a salt thereof, followed by a deprotection reaction if necessary.

This production method employs a conventional means of peptide synthesis, such as liquid phase synthesis or solid phase synthesis. Any optionally chosen known method can be used for such peptide synthesis. For example, the desired compound is produced by the methods described by M. Bondasky and M. Ondetti in Peptide Synthesis, Interscience Publishers, New York (1966), by F. M. Finn and K. Holmann in The Proteins, Vol. 2, edited by H. Nenrath and R. L. Hill, Academic Press Inc., New York (1976), by Nobuo Izumiya et al. in "Peptide Gosei No Kiso To Jikken" (in Japanese), Maruzen (1985), by H. Yajima, S. Sakakibara et al. in "Seikagaku Jikken Koza 1," edited by the Japanese Biochemical Society, Tokyo Kagaku Dojin (1977), by T. Kimura et al. in "Zoku Seikagaku Jikken Koza 2," edited by the Japanese Biochemical Society, Tokyo Kagaku Dojin (1987), and by J. M. Stewart and J. D. Young in Solid Phase Peptide Synthesis, Pierce Chemical Company, Illinois (1984), or modifications thereof. Specifically, there may be mentioned the azide method, the chloride method, the acid anhydride method, the mixed acid anhydride method, the DCC method, the active ester method, the method using Woodward reagent K, the carbonylimidazole method, the oxidation reduction method, the DCC/HONB method, the DIC/HONB method, the DCC/HOBT method, the WSC/HOBT method and the method using BOP reagent, in which compound (E) or a salt thereof or compound (IV) or a salt thereof has its carboxylic acid moiety activated and is then condensed with compound (III) or a salt thereof or compound (V) or a salt thereof, respectively.

With respect to the protection of functional groups not to be involved in the starting material reaction, the protecting groups used, elimination of the protecting groups, activation of the functional groups involved in the reaction, etc., per se known functional groups or per se known means can be chosen as appropriate.

This reaction may be carried out in the presence of a base. Useful bases include tertiary amines such as trimethylamine, triethylamine, tripropylamine, N-methylpiperidine, N-methylpyrrolidine, cyclohexyldimethylamine and N-methylmorpholine, secondary mines such as di-n-butylamine, diisobutylamine and dicyclohexylamine, aromatic amines such as pyridine, lutidine and collidine, hydroxides or salts of alkali metals such as lithium, sodium and potassium, and hydroxides or salts of alkaline earth metals such as calcium and magnesium.

In this method, a reactive derivative of carboxylic acid compound (II) or (IV) is normally used at 1 mol per tool of compound (III) or (V), but may be used in excess, as long as the reaction is not interfered with. When a base is used, its mount is normally 1 to 5 tool, preferably about 1 to 3 mol per mol of compound (III) or (V), varying depending on starting material compound used, kind of reactive carboxylic acid derivative and other reaction conditions.

This reaction is normally carried out in a solvent which does not interfere with the reaction. The solvent is chosen as appropriate from known solvents useful in peptide condensation reaction. Such solvents include amides such as formamide, N,N-dimethylformamide and N-methylpyrrolidone, sulfoxides such as dimethyl sulfoxide, aromatic amines such as pyridine, halogenated hydrocarbons such as chloroform and dichloromethane, ethers such as tetrahydrofuran and dioxane, nitriles such as acetonitrile, esters such as ethyl acetate and ethyl formate, and appropriate mixtures thereof.

Reaction temperature is normally about -50° to 150° C., preferably -30° to 80° C., although it does not subject to limitation, as long as the reaction proceeds. Reaction time is normally several scores of minutes to several scores of hours, depending on starting material, base, reaction temperature and kind of solvent used.

A compound represented by general formula (I) or a salt thereof can be produced by subjecting a compound or a salt thereof produced by the above-described method to a deprotection reaction if necessary. This deprotection reaction can be carried out by a per se known method, such as a method in common use in peptide chemistry (see Gosei Kagaku Series, Peptide Gosei, by N. Izumiya, M. Ono, T. Kato and T. Aoyagi, published by Maruzen, 1975).

The deprotection reaction for the amino group protected by an urethane type protecting group is carried out in contact with an acid in the absence of a solvent or in a solvent which does not interfere with the reaction. The solvent is exemplified by halogenated hydrocarbons (e.g., dichloromethane, chloroform, 1,2-dichloroethane), alcohols (e.g., methanol, ethanol), water and appropriate mixtures thereof. The acid is exemplified by haloacetic acids (e.g., trifluoroacetic acid) and hydrohalo acids (e.g., hydrochloric acid, hydrobromic acid).

It is advantageous that the N-benzyloxycarbonyl (Z) group and the N-4-methoxybenzyloxycarbonyl group be eliminated by catalytic hydrogenation using, e.g., a palladium catalyst (e.g., palladium/barium sulfate, palladium/activated carbon, palladium black), a rhodium catalyst or the like. This reaction is carried out in a solvent which does not interfere with the reaction. Such solvents include amides (e.g., N,N-dimethylformamide, acetamide), alcohols (e.g., methanol, ethanol), cyclic ethers (e.g., tetrahydrofuran), organic carboxylic acids (e.g., acetic acid, propionic acid), water and appropriate mixtures thereof.

It is advantageous that the N-9-fluorenylmethyloxycarbonyl (Fmoc) group be eliminated using an organic amine such as diethylamine, piperidine, morpholine, 4-dimethylaminopyridine or dicyclohexylamine. This reaction is carried out in a solvent which does not interfere with the reaction. Such solvents include amides (e.g., N,N-dimethylformamide, acetamide), alcohols (e.g., methanol, ethanol) and appropriate mixtures thereof.

It is advantageous that the N-2,2,2-trichloroethyloxycarbonyl group be eliminated using a metal (e.g., zinc) along with an organic carboxylic acid (e.g., acetic acid, propionic acid). This reaction is carried out in a solvent which does not interfere with the reaction. Such solvents include the above-mentioned organic carboxylic acids, alcohols (e.g., methanol, ethanol), water and appropriate mixtures thereof.

The deprotection reaction (deacylation) of the acylated hydroxy group is achieved in contact with an acid in a solvent which does not interfere with the reaction. Such solvents include halogenated hydrocarbons (e.g., dichloromethane, chloroform, 1,2-dichloroethane), alcohols (e.g., methanol, ethanol), water and appropriate mixtures thereof. Useful acids include haloacetic acids (e.g., trifluoroacetic acid) and hydrohalo acids (e.g., hydrochloric acid, hydrobromic acid).

It is advantageous that the O-benzyl (Bzl) group be eliminated by catalytic hydrogenation using, e.g., a palladium catalyst (e.g., palladium/barium sulfate, palladium/activated carbon, palladium black) or a rhodium catalyst. In this case, a solvent known from the literature, such as a cyclic ether (e.g., tetrahydrofuran), is used singly or, in some cases, in mixture with another inert solvent [e.g., lower aliphatic acid amide (e.g., N,N-dimethylformamide)].

For the O-tetrahydropyranyl group or O-tert-butyl group, deprotection can be achieved by acid hydrolysis as in the above-described deacylation.

The carboxyl protecting group can be eliminated by acid hydrolysis in the same manner as above. For example, the benzyl ester can be eliminated by catalytic hydrogenation in the same manner as for the above-described elimination of the O-benzyl group. The methyl ester or ethyl ester can be eliminated in contact with a base in a solvent which does not interfere with the reaction. The solvent is exemplified by alcohols (e.g., methanol, ethanol), cyclic ethers (e.g., tetrahydrofuran), water and appropriate mixtures. The base is exemplified by sodium hydroxide, potassium hydroxide, sodium carbonate and potassium carbonate.

The 2-(trimethylsilyl)-ethyl group can be eliminated by reacting a salt of hydrofluoric acid, such as a quaternary nitrogen base salt of hydrofluoric acid (e.g., tetraethylammonium fluoride) in an appropriate solvent under neutral conditions.

Compound (I) or a salt thereof thus produced is collected by a process of isolating peptide, for example, extraction, distribution, reprecipitation, crystallization, recrystallization, various kinds of chromatography, high performance liquid chromatography, or the like, after completion of the reaction.

Compound (II) above or a salt thereof can be produced by condensing compound (IV) or a salt thereof and a compound represented by the general formula:

wherein $R^2$ and n have the same definitions as above; $R^7$ represents a protected carboxyl group, or a salt thereof, by a conventional means of peptide synthesis like that described above, followed by a deprotection reaction to eliminate the carboxyl protecting group.

The carboxyl-protecting group in the protected carboxyl group represented by $R^7$ above is exemplified by (1) $C_{1-6}$ alkyl groups (e.g. methyl, ethyl, propyl, isopropyl, butyl, isobutyl, sec-butyl, tert-butyl, pentyl, isopentyl, sec-pentyl, neopentyl, tert-pentyl, hexyl) optionally having 1 to 3 substituents selected from (a) halogen atoms (e.g. chlorine, bromine, fluorine), (b) $C_{2-7}$ alkanoyl groups (e.g. acetyl, propionyl, butyryl, valeryl) and (c) nitro group, (2) $C_{6-10}$ aryl groups (e.g. phenyl, naphthyl) optionally having 1 to 3 substituents selected from (a) halogen atoms (e.g. chlorine, bromine, fluorine), (b) $C_{1-6}$ alkoxy groups (e.g. methoxy, ethoxy, propoxy, isopropoxy, butoxy, isobutoxy, sec-butoxy, tert-butoxy) and (c) nitro group, (3) $C_{7-12}$ aralkyl groups optionally having 1 to 3 substituents selected from (a) halogen atoms (e.g. chlorine, bromine, fluorine), (b) $C_{1-6}$ alkoxy groups (e.g. methoxy, ethoxy, propoxy, isopropoxy, butoxy, isobutoxy, sec-butoxy, tert-butoxy) and (c) nitro group, (4) trityl group optionally having 1 to 3 substituents selected from (a) halogen atoms (e.g. chlorine, bromine, fluorine), (b) $C_{2-7}$ alkanoyl group (e.g. acetyl, propionyl, butyryl, valeryl) and (c) nitro group, and (5) tri-$C_{1-4}$ alkylsilyl groups (e.g. trimethylsilyl, triethylsilyl).

Compound (V) above or a salt thereof can be produced by condensing a compound represented by the general formula:

wherein $R^2$ and n have the same definitions as above; $R^8$ represents a protected amino group, or a salt thereof and compound (III) or a salt thereof by a conventional means of peptide synthesis like that described above, followed by a deprotection reaction to eliminate the amino protecting group.

The amino-protecting group in the protected amino group for $R^8$ above is identical with the protecting group for the amino group in the hydrocarbon residue which is substituted by an optionally protected amino group for $R^4$ above.

A method of producing the compound (XI) or a salt thereof is described below.

The compound (XI) or a salt thereof can be produced by reacting a compound represented by the general formula:

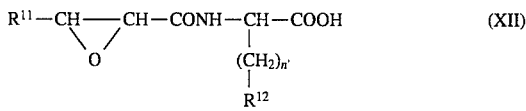

wherein $R^{11}$, $R^{12}$ and n' have the same definitions as above, or a salt thereof, with a compound represented by the general formula:

wherein $R^{13}$ and $R^{14}$ have the same definitions as above, or a salt thereof, followed by a deprotection reaction if necessary, or by reacting a compound represented by the general formula:

wherein $R^{11}$ has the same definition as above, or a salt thereof, with a compound represented by the general formula:

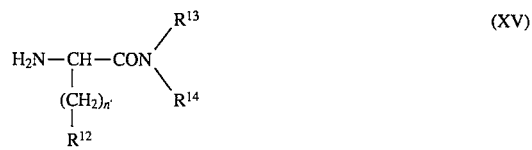

wherein $R^{12}$, $R^{13}$, $R^{14}$ and n' have the same definitions as above, or a salt thereof, followed by a deprotection reaction if necessary.

In this production method, the reaction between the compound (XII) and the compound (XTII) is conducted in substantially the same manner as the above-described reaction between the compound (II) and the compound (III). And, the reaction between the compound (XIV) and the compound (XV) is conducted in substantially the same manner as the above-described reaction between the compound (IV) and the compound (V). Further, the deprotection reaction is conducted in substantially the same manner as in the method of producing the compound (I).

The compound (XI) or a salt thereof thus produced is collected, after completion of the reaction, by a process of isolating peptide, for example, extraction, distribution, reprecipitation, crystallization, recrystallization, various kinds of chromatography, high performance liquid chromatography or the like.

The above-mentioned compound (XII) or a salt thereof can be produced by condensing the compound (XIV) or a salt thereof and a compound represented by the general formula:

wherein $R^{12}$ and n' have the same definitions as above; $R^{17}$ represents a protected carboxyl group, or a salt thereof, by a conventional means of peptide synthesis like that described above, followed by a deprotection reaction to eliminate the carboxyl protecting group. The carboxyl protecting group in the protected carboxyl group for $R^{17}$ is substantially the same as that in the protected carboxyl group for $R^7$.

The above-mentioned compound (XV) or a salt thereof can be produced by condensing the compound represented by the general formula

wherein $R^{12}$ and n' have the same definitions as above, $R^{18}$ represents a protected amino group, or a salt thereof and the compound (XIII) or a salt thereof by a conventional means for peptide synthesis like that described above, followed by a deprotection reaction to eliminate the amino protecting group.

The amino protecting group in the protected amino group for $R^{18}$ mentioned above has the same definitions as the amino-protecting group in the hydrocarbon residue which is substituted by an optionally protected amino group for $R^4$ mentioned above.

A method of producing compound (XXI) or a salt thereof is described below.

A compound represented by general formula (XXI) above or a salt thereof can be produced by reacting a compound represented by the general formula:

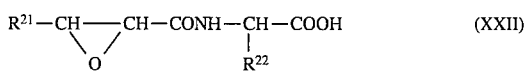

wherein $R^{21}$ and $R^{22}$ the same definitions as above, or a salt thereof, with a compound represented by the general formula:

wherein $R^{23}$ and $R^{24}$ have the same definitions as above, or a salt thereof, followed by a deprotection reaction if necessary, or by reacting a compound represented by the general formula:

wherein $R^{21}$ has the same definition as above, or a salt thereof, with a compound represented by the general formula:

wherein $R^{22}$, $R^{23}$ and $R^{24}$ have the same definitions as above, or a salt thereof, followed by a deprotection reaction if necessary.

In this production method, the reaction between the compound (XXII) and the compound (XXIII) is conducted in substantially the same manner as the above-described reaction between the compound (II) and the compound ((III). And, the reaction between the compound (XXIV) and the compound (XXV) is conducted in substantially the same manner as the above-described reaction between the compound (IV) and the compound (V). Further, the deprotection reaction is conducted in substantially the same manner as in the method of producing the compound (I).

Compound (XXI) or a salt thereof thus produced can be collected by isolating peptide, for example, extraction, distribution, reprecipitation, crystallization, recrystallization, various kinds of chromatography high performance liquid chromatography, or the like, after completion of the reaction.

Compound (XXII) above or a salt thereof can be produced by condensing compound (XXIV) or a salt thereof and a compound represented by the general formula:

wherein $R^{22}$ has the same definition as above; $R^{25}$ represents a protected carboxyl group, or a salt thereof, by the same production method as above, followed by a deprotection reaction to eliminate the carboxyl protecting group.

The protecting group for the protected carboxyl group for $R^{25}$ above is identical with the protecting group for the protected carboxyl group for $R^7$ above.

Compound (XXV) above or a salt thereof can be produced by condensing a compound represented by the general formula:

wherein $R^{22}$ has the same definition as above; $R^{26}$ represents a protected amino group, or a salt thereof, and compound (XXIII) or a salt thereof by the same production method as above, followed by a deprotection reaction to eliminate the amino protecting group.

The protecting group for the protected amino group for $R^{26}$ above is identical with the protecting group for the amino group in the alkyl group which is substituted by an optionally protected amino group for $R^4$ above.

The compound (I) of the present invention can also be obtained as an alkali metal salt such as sodium salt and potassium salt, an alkaline earth metal salt such as calcium salt and magnesium salt, an acid-addition salt, particularly a pharmacologically acceptable acid-addition salt by a per se known method. Such salts include salts formed with inorganic acids (e.g., hydrochloric acid, sulfuric acid, phosphoric acid) and salts formed with organic acids (e.g., acetic acid, propionic acid, citric acid, tartaric acid, malic acid, oxalic acid, methanesulfonic acid, octanesulfonic acid).

With respect to the salts of compounds (II) through (VII), the same applies as with compound (I).

With respect to the salts of compound (XI) and compounds (XII) through (XVII), the same applies as with compound (I).

With respect to the salts of compound (XXI) and compounds (XXII) through (XXVII), the same applies as with compound (I).

The structural formulas of the compounds obtained in the Examples below are given below.

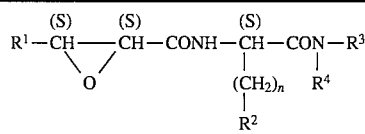

| Compound No. | Example No. | (*,*,*) | n | $R^1$ | $R^2$ | $R^3$ | $R^4$ |
|---|---|---|---|---|---|---|---|
| 1 | 2 | (S,S,S) | 1 | COOH | Ph | H | $(CH_2)_4NH_2$ |
| 2 | 2 | (S,S,S) | 1 | COOH | 4-OH—Ph | H | $(CH_2)_4NH_2$ |
| 3 | 4 | (S,S,S) | 1 | COOH | Ph | $(CH_2)_3NH_2$ | $(CH_2)_4NH_2.HCl$ |

-continued

| | | | | | | | |
|---|---|---|---|---|---|---|---|
| 4 | 4 | (S,S,S) | 1 | COOH | 4-OH—Ph | (CH$_2$)$_3$NH$_2$ | (CH$_2$)$_4$NH$_2$.HCl |
| 5 | 5 | (S,S,S) | 1 | COOC$_2$H$_5$ | Ph | H | (CH$_2$)$_4$NHZ |
| 6 | 6 | (S,S,S) | 1 | COOH | Ph | H | (CH$_2$)$_4$NHZ |
| 7 | 8 | (S,S,S) | 1 | COOC$_2$H$_5$ | 4-(OBzl)-Ph | H | (CH$_2$)$_4$NHZ |
| 8 | 9 | (S,S,S) | 1 | COOH | 4-(OBzl)-Ph | H | (CH$_2$)$_4$NHZ |
| 9 | 11 | (S,S,R) | 1 | COOC$_2$H$_5$ | Ph | H | (CH$_2$)$_4$NHZ |
| 10 | 12 | (S,S,R) | 1 | COOH | Ph | H | (CH$_2$)$_4$NHZ |
| 11 | 13 | (S,S,R) | 1 | COOH | Ph | H | (CH$_2$)$_4$NH$_2$ |
| 12 | 14 | (R,R,S) | 1 | COOCH$_3$ | Ph | H | (CH$_2$)$_4$NHZ |
| 13 | 15 | (R,R,S) | 1 | COOH | Ph | H | (CH$_2$)$_4$NHZ |
| 14 | 16 | (R,R,S) | 1 | COOH | Ph | H | (CH$_2$)$_4$NH$_2$ |
| 15 | 17 | (S,S,S) | 1 | COOC$_2$H$_5$ | 3-indolyl | H | (CH$_2$)$_4$NHZ |
| 16 | 18 | (S,S,S) | 1 | COOH | 3-indolyl | H | (CH$_2$)$_4$NHZ |
| 17 | 19 | (S,S,S) | 1 | COOH | 3-indolyl | H | (CH$_2$)$_4$NH$_2$ |
| 18 | 20 | (S,S,S) | 1 | COOC$_2$H$_5$ | Ph | H | (CH$_2$)$_2$NHZ |
| 19 | 21 | (S,S,S) | 1 | COOH | Ph | H | (CH$_2$)$_2$NHZ |
| 20 | 22 | (S,S,S) | 1 | COOH | Ph | H | (CH$_2$)$_2$NH$_2$ |
| 21 | 23 | (S,S,S) | 1 | COOC$_2$H$_5$ | Ph | H | (CH$_2$)$_8$NHZ |
| 22 | 24 | (S,S,S) | 1 | COOH | Ph | H | (CH$_2$)$_8$NHZ |
| 23 | 25 | (S,S,S) | 1 | COOH | Ph | H | (CH$_2$)$_8$NH$_2$ |
| 24 | 26 | (S,S,S) | 1 | COOC$_2$H$_5$ | Ph | —(CH$_2$)$_2$N(CH$_3$)(CH$_2$)$_2$— | |
| 25 | 27 | (S,S,S) | 1 | COOH | Ph | —(CH$_2$)$_2$N(CH$_3$)(CH$_2$)$_2$— | |
| 26 | 28 | (S,S,S) | 1 | COOC$_2$H$_5$ | Ph | —(CH$_2$)$_2$O(CH$_2$)$_2$— | |
| 27 | 29 | (S,S,S) | 1 | COONa | Ph | —(CH$_2$)$_2$O(CH$_2$)$_2$— | |
| 28 | 30 | (S,S,S) | 1 | COOC$_2$H$_5$ | Ph | H | (CH$_2$)$_4$NHAc |
| 29 | 31 | (S,S,S) | 1 | COONa | Ph | H | (CH$_2$)$_4$NHAc |
| 30 | 34 | (S,S,S) | 1 | COOH | Ph | H | (CH$_2$)$_4$NH(CH$_3$)$_3$NH$_2$.1/2H$_2$SO$_4$ |
| 31 | 34 | (S,S,S) | 1 | COOH | Ph | H | (CH$_2$)$_4$NH(CH$_2$)$_4$NH$_2$.1/2H$_2$SO$_4$ |
| 32 | 35 | (S,S,S) | 1 | COOC$_2$H$_5$ | Ph | H | (CH$_2$)$_4$NHTs |
| 33 | 36 | (S,S,S) | 1 | COONa | Ph | H | (CH$_2$)$_4$NHTs |
| 34 | 37 | (S,S,S) | 1 | COOC$_2$H$_5$ | Ph | H | (CH$_2$)$_4$NHBut |
| 35 | 38 | (S,S,S) | 1 | COONa | Ph | H | (CH$_2$)$_4$NHBut |
| 36 | 39 | (S,S,S) | 1 | COOC$_2$H$_5$ | 2-F—Ph | H | (CH$_2$)$_4$NHZ |
| 37 | 40 | (S,S,S) | 1 | COOH | 2-F—Ph | H | (CH$_2$)$_4$NHZ |
| 38 | 41 | (S,S,S) | 1 | COOH | 2-F—Ph | H | (CH$_2$)$_4$NH$_2$ |
| 39 | 42 | (S,S,S) | 1 | COOC$_2$H$_5$ | 5-(1-Ts-imidazolyl) | H | (CH$_2$)$_4$NHZ |
| 40 | 43 | (S,S,S) | 1 | COOH | 5-imidazolyl | H | (CH$_2$)$_4$NHZ |
| 41 | 44 | (S,S,S) | 1 | COOH | 5-imidazolyl | H | (CH$_2$)$_4$NH$_2$ |
| 42 | 45 | (S,S,S) | 4 | COOC$_2$H$_5$ | NHZ | H | (CH$_2$)$_4$NHZ |
| 43 | 46 | (S,S,S) | 4 | COOH | NHZ | H | (CH$_2$)$_4$NHZ |
| 44 | 47 | (S,S,S) | 1 | COOC$_2$H$_5$ | OBzl | H | (CH$_2$)$_4$NHZ |
| 45 | 48 | (S,S,S) | 1 | COOH | OBzl | H | (CH$_2$)$_4$NHZ |
| 46 | 49 | (S,S,S) | 1 | COOH | OBzl | H | (CH$_2$)$_4$NH$_2$ |
| 47 | 49 | (S,S,S) | 1 | COOH | OH | H | (CH$_2$)$_4$NH$_2$ |
| 48 | 50 | (S,S,S) | 1 | COOC$_2$H$_5$ | STrt | H | (CH$_2$)$_4$NHBoc |
| 49 | 51 | (S,S,S) | 1 | COOH | STrt | H | (CH$_2$)$_4$NHBoc |
| 50 | 52 | (S,S,S) | 1 | COOH | STrt | H | (CH$_2$)$_4$NH$_2$ |
| 51 | 53 | (S,S,S) | 2 | COOC$_2$H$_5$ | CONH$_2$ | H | (CH$_2$)$_4$NHZ |
| 52 | 54 | (S,S,S) | 2 | COOH | CONH$_2$ | H | (CH$_2$)$_4$NHZ |
| 53 | 55 | (S,S,S) | 2 | COOH | CONH$_2$ | H | (CH$_2$)$_4$NH$_2$ |
| 54 | 56 | (S,S,S) | 2 | COOC$_2$H$_5$ | COOBzl | H | (CH$_2$)$_4$NHZ |
| 55 | 57 | (S,S,S) | 2 | COOCH$_3$ | COOCH$_3$ | H | (CH$_2$)$_4$NHZ |
| 56 | 58 | (S,S,S) | 1 | COOC$_2$H$_5$ | Ph | H | (CH$_2$)$_4$NH$_2$.1/2H$_2$SO$_4$ |
| 57 | 59 | (S,S,S) | 1 | COOC$_2$H$_5$ | Ph | H | (CH$_2$)$_4$NH$_2$.C$_8$H$_{17}$SO$_3$H |
| 58 | 60 | (S,S,S) | 1 | COOC$_2$H$_5$ | 4-(OBzl)-Ph | —(CH$_2$)$_2$O(CH$_2$)$_2$— | |
| 59 | 61 | (S,S,S) | 1 | COOC$_2$H$_5$ | 4-OH—Ph | —(CH$_2$)$_2$O(CH$_2$)$_2$— | |
| 60 | 62 | (S,S,S) | 1 | COONa | 4-OH—Ph | —(CH$_2$)$_2$O(CH$_2$)$_2$— | |
| 61 | 63 | (S,S,S) | 1 | COOC$_2$H$_5$ | 3,4-di-OH—Ph | —(CH$_2$)$_2$O(CH$_2$)$_2$— | |
| 62 | 64 | (S,S,S) | 1 | COONa | 3,4-di-OH—Ph | —(CH$_2$)$_2$O(CH$_2$)$_2$— | |
| 63 | 65 | (S,S,S) | 0 | COOC$_2$H$_5$ | Ph | —(CH$_2$)$_2$O(CH$_2$)$_2$— | |
| 64 | 66 | (S,S,S) | 0 | COONa | Ph | —(CH$_2$)$_2$O(CH$_2$)$_2$— | |
| 65 | 67 | (S,S,S) | 2 | COOC$_2$H$_5$ | Ph | —(CH$_2$)$_2$O(CH$_2$)$_2$— | |
| 66 | 68 | (S,S,S) | 2 | COONa | Ph | —(CH$_2$)$_2$O(CH$_2$)$_2$— | |
| 67 | 69 | (S,S,S) | 1 | COOC$_2$H$_5$ | 4-Cl—Ph | —(CH$_2$)$_2$O(CH$_2$)$_2$— | |
| 68 | 70 | (S,S,S) | 1 | COONa | 4-Cl—Ph | —(CH$_2$)$_2$O(CH$_2$)$_2$— | |
| 69 | 71 | (S,S,S) | 1 | COOC$_2$H$_5$ | 4-F—Ph | —(CH$_2$)$_2$O(CH$_2$)$_2$— | |
| 70 | 72 | (S,S,S) | 1 | COONa | 4-F—Ph | —(CH$_2$)$_2$O(CH$_2$)$_2$— | |
| 71 | 73 | (S,S,S) | 1 | COOC$_2$H$_5$ | 4-NO$_2$—Ph | —(CH$_2$)$_2$O(CH$_2$)$_2$— | |
| 72 | 74 | (S,S,S) | 1 | COONa | 4-NO$_2$—Ph | —(CH$_2$)$_2$O(CH$_2$)$_2$— | |
| 73 | 75 | (S,S,S) | 1 | COOC$_2$H$_5$ | 2-Thienyl | —(CH$_2$)$_2$O(CH$_2$)$_2$— | |
| 74 | 76 | (S,S,S) | 1 | COONa | 2-Thienyl | —(CH$_2$)$_2$O(CH$_2$)$_2$— | |
| 75 | 77 | (S,S,S) | 1 | COOC$_2$H$_5$ | Cyclohexyl | —(CH$_2$)$_2$O(CH$_2$)$_2$— | |
| 76 | 78 | (S,S,S) | 1 | COONa | Cyclohexyl | —(CH$_2$)$_2$O(CH$_2$)$_2$— | |
| 77 | 79 | (S,S,S) | 1 | COOC$_2$H$_5$ | 4-(OCH$_3$)—Ph | —(CH$_2$)$_2$O(CH$_2$)$_2$— | |
| 78 | 80 | (S,S,S) | 1 | COONa | 4-(OCH$_3$)—Ph | —(CH$_2$)$_2$O(CH$_2$)$_2$— | |
| 79 | 81 | (S,S,S) | 1 | COOC$_2$H$_5$ | 1-Naphthyl | —(CH$_2$)$_2$O(CH$_2$)$_2$— | |
| 80 | 82 | (S,S,S) | 1 | COONa | 1-Naphthyl | —(CH$_2$)$_2$O(CH$_2$)$_2$— | |
| 81 | 83 | (S,S,S) | 1 | COOC$_2$H$_5$ | 2-Naphthyl | —(CH$_2$)$_2$O(CH$_2$)$_2$— | |
| 82 | 84 | (S,S,S) | 1 | COONa | 2-Naphthyl | —(CH$_2$)$_2$O(CH$_2$)$_2$— | |

-continued

| | | | | | | | |
|---|---|---|---|---|---|---|---|
| 83 | 85 | (S,S,S) | 1 | COOC$_2$H$_5$ | Ph | | —(CH$_2$)$_2$S(CH$_2$)$_2$— |
| 84 | 86 | (S,S,S) | 1 | COONa | Ph | | —(CH$_2$)$_2$S(CH$_2$)$_2$— |
| 85 | 87 | (S,S,S) | 1 | CONHC$_3$H$_7$ | Ph | H | (CH$_2$)$_4$NHZ |

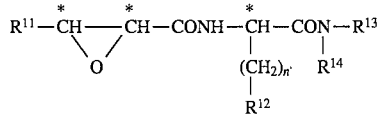

| Compound No. | Example No. | (*,*,*) | n' | R$^{11}$ | R$^{12}$ | R$^{13}$ | R$^{14}$ |
|---|---|---|---|---|---|---|---|
| 86 | 88 | (S,S,S) | 1 | COOC$_2$H$_5$ | Ph | H | CH$_2$CH=CH$_2$ |
| 87 | 89 | (S,S,S) | 1 | COONa | Ph | H | CH$_2$CH=CH$_2$ |
| 88 | 90 | (S,S,S) | 1 | COOC$_2$H$_5$ | 3-Indolyl | H | (CH$_2$)$_2$CH(CH$_3$)$_2$ |
| 89 | 91 | (S,S,S) | 1 | COONa | 3-Indolyl | H | (CH$_2$)$_2$CH(CH$_3$)$_2$ |
| 90 | 92 | (S,S,S) | 1 | COOC$_2$H$_5$ | 2-Naphthyl | H | (CH$_2$)$_2$CH(CH$_3$)$_2$ |
| 91 | 93 | (S,S,S) | 1 | COOH | 2-Naphthyl | H | (CH$_2$)$_2$CH(CH$_3$)$_2$ |

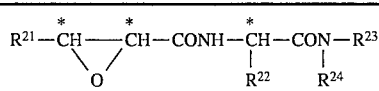

| Compound No. | Example No. | (*,*,*) | R$^{21}$ | R$^{22}$ | R$^{23}$ | R$^{24}$ |
|---|---|---|---|---|---|---|
| 92 | 95 | (S,S,S) | COOH | CH$_2$CH(CH$_3$)$_2$ | (CH$_2$)$_3$NH$_2$ | (CH$_2$)$_4$NH$_2$·HCl |
| 93 | 96 | (S,S,S) | COOC$_2$H$_5$ | CH$_2$CH(CH$_3$)$_2$ | (CH$_2$)$_3$NHZ | (CH$_2$)$_4$NHZ |
| 94 | 97 | (S,S,S) | COOH | CH$_2$CH(CH$_3$)$_2$ | (CH$_2$)$_3$NHZ | (CH$_2$)$_4$NHZ |

S and R indicate that the carbon atoms marked therewith are in the S-and R-configurations, respectively; Ph represents a phenyl group; 4-OH-Ph represents a 4-hydroxyphenyl group; 4-Bzl-O-Ph represents a 4-benzyloxyphenyl group; Ac represents an acetyl group.

The bioactivities of the compounds of the present invention are described below. Compounds (I), (XI) and (XXI) or salts thereof of the present invention potently inhibit thiol protease. Their inhibitory activities against cathepsin L and cathepsin B were determined by the methods described below. The results are given in Table 6.

(a) Determination of Cathepsin L Inhibitory Activity

To 75 μl of a reaction mixture containing 1 ng of human recombinant cathepsin L (as produced in Reference Examples 1 through 7 below), 2 μM dithiothreitol (hereinafter referred to as DTT), 1 mM ethylenediaminetetraacetate disodium salt, 0.1M sodium acetate buffer (pH 5.5) and various concentrations of sample, 25 μl of 20 μM benzyloxycarbonyl-L-phenylalanyl-L-arginine-4-methylcoumaryl-7-amide (hereinafter referred to as Z-Phe-Arg-7MCA, produced by Peptide Institute, Inc.) was added to initiate the reaction. After incubation at 37° C. for 20 minutes, 100 μl of a reaction stopper solution containing 100 mM sodium monochloroacetate was added. The amount of liberated 4-methyl-7-aminocoumarin was determined at an excitation wavelength of 365 nm and a fluorescence wavelength of 450 nm, using a fluorophotometer (FCA; produced by Baxter). The sample concentration required to cause 50% inhibition was expressed as the IC$_{50}$ value, with the fluorescence value obtained from the same reaction in the absence of the sample taken as 100%.

(b) Determination of Cathepsin B Inhibitory Activity

To 75 μl of a reaction mixture containing 30 ng of cathepsin B (produced by Sigma), 2 μM DTT, 1 mM ethylenediaminetetraacetate disodium salt, 0.1M sodium acetate buffer (pH 5.5) and various concentrations of sample, 25 μl of 20 μM Z-Phe-Arg-7MCA was added to initiate the reaction. After reaction mixture incubation at 37° C. for 20 minutes, 100 μl of a reaction stopper solution containing 100 mM sodium monochloroacetate was added. The amount of liberated 4-methyl-7-aminocoumarin was determined at an excitation wavelength of 365 nm and a fluorescence wavelength of 450 nm, using a fluorophotometer. The sample concentration required to cause 50% inhibition was expressed as the IC$_{50}$ value, with the fluorescence value obtained from the same reaction in the absence of the sample taken as 100%.

TABLE 6

| Compound number | Inhibitory activity potency IC$_{50}$ (ng/ml) | |
|---|---|---|
| | Cathepsin L | Cathepsin B |
| 23 | 2 | 24 |
| 37 | 1 | 14 |
| 82 | 2 | 34 |

Compounds (I), (XI) and (XXI) or salts thereof excellently suppress bone resorption. Their suppressive action against bone resorption as enhanced by PTH (parathyroid hormone) was determined by the method described below. The results are given in Table 7.

Determination of Bone Resorption Suppressive Activity

Femurs were aseptically isolated from female BALB/c mice at 8–10 weeks of age. After the bone marrow cavity was washed with a Ham F12 medium containing 10% (w/w) thermally inactivated fetal calf serum, 100 unit/ml penicillin G and 100 unit/ml streptomycin (hereinafter referred to as culture broth), each femur was added to 1 ml of the culture broth and precultured for 3 hours at 37° C. in the presence of 5% carbon dioxide and 95% air. Each bone was transferred to 1 ml of the culture broth supplemented with PTH (produced by Peptide Institute, Inc., final concentration 1 μM) and the test compound (final concentration 10 μg/ml) and cultured for 7 more days, after which the total calcium content in the culture broth was determined using Calcium E-Test Wako (produced by Wako Pure Chemical Industries). The bone resorption suppressive activity of the test compound was calculated using the following equation:

Bone resorption suppressive activity (%)=100×(Cp−Cs)/(Cp−Cc)

Cc: Total calcium content in the culture broth containing neither PTH nor test compound
Cp: Total calcium content in the culture broth containing PTH
Cs: Total calcium content in the culture broth containing both PTH and test compound

TABLE 7

| Compound number | Bone resorption suppressive activity (%) |
| --- | --- |
| 1 | 150 |
| 92 | 149 |

Toxicity Study

TAN-1756A caused no death in mice when it was intraperitoneally or orally administered at 400 mg/kg.

TAN-1803 monohydrochloride caused no death in mice when it was intraperitoneally or orally administered at 400 mg/kg.

As described hereinbefore, the compounds (I), (XI) and (XXI) or salts thereof have an inhibitory activity against thiol protease such as cathepsin L and cathepsin B, which can be used as thiol protease inhibitory agents being useful for prophylactic and therapeutic agents for diseases caused by thiol protease (e.g. muscular dystrophy, aerocystic distal myopathy). Besides, since substances inhibiting thiol protease show an anti-inflammatory activity the inhibitory agent of the present invention can be used as an anti-inflammatory agent as well.

Further, the compounds (I), (XI) and (XXI) or salts thereof have bone resorption suppressive activity, which are used as prophylactic and therapeutic agents for bone diseases such as osteoporosis, hypercalcemia in malignancy and Paget's disease.

The compounds (I), (XI) and (XXI) or salts thereof are low in toxicity, which can be safely used for mammals (e.g. dogs, cats, horses, cows, monkeys, humans).

When compound (I) or a salt thereof is administered to, for example, a human, it can be safely administered orally or non-orally as such, or in a pharmaceutical composition along with an appropriate pharmacologically acceptable carrier, excipient and diluent.

Such pharmaceutical compositions include non-oral preparations such as injections, and oral preparations (e.g., powders, granules, capsules, tablets).

These preparations can be produced by per se known methods in common use for pharmaceutical preparation.

Compound (I) or a salt thereof can be formulated into an aqueous injection along with a dispersing agent [e.g., Tween 80 (produced by Atlas Powder, USA), HCO 60 (produced by Nikko Chemicals), polyethylene glycol, carboxymethyl cellulose, sodium alginate], a preservative (e.g., methyl paraben, propyl paraben, benzyl alcohol, chlorobutanol), an isotonizing agent (e.g., sodium chloride, glycerol, sorbitol, glucose) and other additives.

Also, compound (I) or a salt thereof can be prepared as an oral preparation by compressive shaping in the presence of an excipient (e.g., lactose, sucrose, starch), a disintegrating agent (e.g., calcium carbonate), a binder (e.g., gum arabic, carboxymethyl cellulose, polyvinylpyrrolidone, hydroxypropyl cellulose), a lubricant (e.g., talc, magnesium stearate, polyethylene glycol 6000) and other additives, followed by coating if necessary for the purpose of taste masking, enteric release or sustained release by a per se known method. Coating agents for this purpose include ethyl cellulose, hydroxymethyl cellulose, polyoxyethylene glycol, cellulose acetate phthalate, hydroxypropylmethyl cellulose phthalate and Eudragit (produced by Rohm, Germany, methacrylic acid-acrylic acid copolymer).

The dose of compound (I) or a salt thereof in humans is normally about 1 mg to 2 g, preferably about 10 mg to 2 g, more preferably about 20 mg to 1 g daily, based on active ingredient content, in oral administration to an adult patient weighing 50 kg, varying depending on target disease, route of administration, age of subject individual and severity of disease.

When the compound (XI) or a salt thereof is administered to, for example, a human, it can be safely administered orally or non-orally as such or in a pharmaceutical composition along with an appropriate pharmaceutically acceptable carrier, excipient and diluent, as in the case of the above-described compound (I) or a salt thereof.

The dose of compound (XI) or a salt thereof in humans is substantially the same as that of the above-described compound (I) or a salt thereof.

When the compound (XXI) or a salt thereof is administered to, for example, a human, it can be safely administered orally or non-orally as such or in a pharmaceutical composition along with an appropriate pharmaceutically acceptable carrier, excipient and diluent, as in the case of the above-described compound (I) or a salt thereof.

The dose of compound (XXI) or a salt thereof in humans is substantially the same as that of the above-described compound (I) or a salt thereof.

The present invention is hereinafter described in more detail by means of, but not limited to, the following reference examples, working examples and preparation examples. Percent (%) ratios are percent by weight/volume, unless otherwise stated. Figures for mixing ratios for mixed solvents are by volume.

NMR spectra were taken using the Bruker AC-300 spectrometer. The internal substances used were dioxane (δ 69.5 ppm) for $^{13}$C-NMR spectrometry and 3-(trimethylsilyl)propionic acid-$d_4$ sodium salt in heavy water and tetramethylsilane in other solvents for $^1$H-NMR spectrometry; all δ values are expressed in ppm. The symbols used in the present specification have the following meanings: Q, quaternary carbon; CH, roethine; $CH_2$, methylene; $CH_3$, methyl; s, singlet; d, doublet; t, triplet; q, quartet; dd, double doublet; dr, double triplet; ddd, double double doublet; ddt, double double triplet; m, multipict; br., broad; $CDCl_3$, heavy chloroform; DMSO-$d_6$, heavy dimethyl sulfoxide; $D_2O$, heavy water.

Reference Example 1

Cloning of Cathepsin L cDNA of Human Renal Origin

To amplify human cathepsin cDNA by the polymerase chain reaction (PCR) method, four primers were synthesized in accordance with a reported base sequence of cathepsin L of human renal origin IS. Gal and M. M. Gottesman, Biochemical Journal, Vol. 253, p. 303 (1988)] as follows:
Sense primer No. 1: 5'-TTTTCAGGGGGCAGTAAGAT-3'
Sense primer No. 2: 5'-pCCGGATCCGGCTTTTAGGAT-TGGTCTA-3'
Antisense primer No. 3: 5'-GGGGGCTGGTAGACT-GAAGA-3'
Antisense primer No. 4: 5'-pCCGGATCCATTCCTCCCAT-GCATGCGCC-3'

3 µl of a solution of the human renal cDNA library λgt11 (CLONTECH Laboratories, Inc.) and 50 µl of distilled water were mixed. After incubation at 95° C. for 5 minutes, the mixture was immediately cooled in ice. Two primers (Nos. 1 and 3 above, 50 pmol of each) were added, and PCR was carried out in the instruction manual for the kit supplied by Cetus/Perkin-Elmer, in which a series of reactions at 94° C. for 1 minute, 55° C. for 2 minutes and 72° C. for 3 minutes was repeated in 50 cycles. To the reaction mixture, two other primers (Nos. 2 and 4 above, 50 pmol of each) were added, and PCR was carried out in the same manner as above. The PCR product was separated by electrophoresis on 1.2% agarose gel; an amplified DNA fragment was seen at a position corresponding to the size (1132 bp) expected from the base sequence of cathepsin L of human renal origin. This DNA fragment was recovered from the gel and subcloned to the plasmid vector pBluescript$^R$ II SK+(produced by STRATAGENE). The base sequence of the cDNA portion was determined by the dideoxynucleotide synthetic chain termination method [J. Messing et al., Nucleic Acid Research, 9,309 (1981)]; it proved identical with the reported sequence. The plasmid containing this cDNA fragment was named pHCL-5.

Reference Example 2

Expression of human cathepsin L in *Escherichia coli* MM294(DE3)

The cDNA of Reference Example 1 was cleaved with restriction enzyme EcoRI and a 798 bp fragment (which encodes a part of the human cathepsin L precursor and the whole matured human cathepsin L) was recovered. To both ends of this fragment was ligated a BamHI linker (5'-pCCCGGATCCGGG-3'), and the ligation product was inserted to the plasmid vector pET-3c for expression in *Escherichia coli* [Methods in Enzymology, ed. D. V. Goeddel, Vol. 185, p. 68, Academic Press (1990)]. The thus-constructed plasmid was designated as pET-HCLα. *Escherichia coli* MM294(DE3) was transformed with pET-I-ICLα to express human cathepsin L in the presence of the T7 promoter [Methods in Enzymology, Vol. 185, p. 60 (1990)]. The thus-obtained *Escherichia coli* transformant [*Escherichia coli* JM109/pTBN-HCLneo, harboring the plasmid pTBN-I-HCLneo, has been deposited under accession number IFO 15341 at the Institute for Fermentation, Osaka (IFO) since Jun. 12, 1992, and under accession number FERM BP 3897 at the National Institute of Bioscience and Human-Technology (NIBH), Agency of Industrial Science and Technology, Ministry of International Trade and Industry, since Jun. 22, 1992] was cultured, and cells were disrupted by sonication and subjected to SDS-PAGE; a unique band appeared near 30 kDal, corresponding to human cathepsin L. Since the expressed product formed an inclusion body, human cathepsin L was crudely purified from the precipitated fraction of the ultrasonically disrupted transformant.

Reference Example 3

Preparation of Antiserum to Recombinant Human Cathepsin L

The partially purified recombinant human cathepsin L described in Reference Example 2 was mixed with an equal amount of Freund's complete adjuvant, and about 1 ml was inoculated to a rabbit. Later, a mixture of a partially purified human cathepsin L and an equal amount of Freund's incomplete adjuvant was injected 8 times at 10-day intervals, and blood was collected seven days after final injection. The obtained blood was kept standing at 87° C. for 30 minutes and then at 4° C. overnight, after which it was centrifuged to yield a human cathepsin L antiserum.

Reference Example 4

Preparation of Recombinant DNA for Expression of Human Cathepsin L Gene in Animal Cells After the plasmid pHCL-5, described in Reference Example 1, was digested with restriction enzyme BamHi, a fragment of human cathepsin L cDNA was recovered by agarose gel electrophoresis. Next, this cDNA fragment was inserted to the restriction enzyme BglII site of the vector pTB551 for transient expression in animal cells [prepared by converting the EcoRI site to BglII site in the plasmid pTB889 described by Ono et al. in Science, Vol. 2S6, p. 1116 (1989)]by the action of T4 DNA ligase and ATP, to yield the expression plasmid pTB-HCL. MuLV-LTR was inserted between the restriction enzyme HindlII and ClaI sites of pTB-HCL to yield the expression plasmid pTBN-HCL.

Reference Example 5

Preparation of Recombinant DNA for Expression of Human Cathepsin L Gene in Animal Cells To obtain an animal cell line that stably expresses human cathepsin L, the drug resistance marker neogene was inserted to the vector pTBN-HCL described in Reference Example 4 as follows: first, a fragment comprising the SV40 early promoter and the neogene was inserted between the restriction enzyme ClaI and SalI sites of the plasmid pTBN-HCL to yield the plasmid pTBN-HCLneo.

Reference Example 6

Expression of Human Cathepsin L Gene in Animal Cells

Using the plasmid described in Reference Example 5 (pTBN-HCLneo), mouse myeloma Sp2/0 cells were transformed as follows: Sp2/0 cells, cultivated in an ASF104 medium supplemented with 5% fetal calf serum FCS (5% FCS/ASF medium), were suspended in phosphate-buffered saline (PBS) (−) [the same as Dullbecco's PBS but $CaCl_2$ and $MgCl_2$ were removed] to adjust $1 \times 10^7$ cells/ml. 500 µl of this cell suspension was injected to a cuvette, 10 µg of said plasmid DNA was added, and the mixture was kept standing on ice for 5 minutes. This liquid was pulsated at 125 µF and 300 V, using a gene pulsar (produced by Bio-Rad Laboratories), and then again kept standing on ice for 10 minutes. This liquid was transferred to 10 ml of 5% FCS/ASF104 medium and cultured at 37° C. in the presence of 5% carbon dioxide. Forty-eight hours later the culture was transferred to a selection medium (5% FCS/ASF104 medium containing 200 μg/ml G418) and cultured on a 24-well plate for 2 weeks. A number of colonies emerged, each of which was transferred to an ASF104 medium containing 200 μg/ml G418 and cultured, followed by Western blot analysis of the culture supernatant using the human cathepsin L antiserum prepared in Reference Example 3. In response to the antiserum, unique bands corresponding to molecular weights of about 40,000 to 30,000 and lower molecular weights appeared; they were identified as a precursor of human cathepsin L and a processing product thereof, estimated from these molecular weights. The culture supernatant was assayed for cathepsin L activity, in accordance with the method of A. J. Barrett and H. Kirschke [Methods in Enzymology, Vol. 80, p. 535 (1981)]; human cathepsin L activity was detected.

These findings confirm that transformant mouse myeloma cells expressing cathepsin L were obtained, which were designated as the mouse myeloma Sp-HCL26.

Reference Example 7

Purification of Human Cathepsin L

The strain obtained in Reference Example 6, showing high expression of cathepsin L, (the mouse myeloma Sp-HCL26, transformed with the plasmid pTBN-HCLneo, has been deposited under accession number IFO 50371 at the Institute for Fermentation, Osaka (IFO) since Jun. 16, 1992, and under accession number FERM BP 3902 at the National Institute of Bioscience and Human-Technology (NIBH), Agency of Industrial Science and Technology, Ministry of International Trade and Industry, since Jun. 24, 1992), was cultured in 20 ml of an ASF104 medium supplemented with 10% FCS and 200 μg/ml G418, after which it was transferred to 50 ml of a serum-free selection medium (ASF104 medium supplemented with 200 μg/ml G418) and cultured for 5 days. After the culture supernatant was applied to a column of CM-Sephadex C-50 (25×4.4 cm), the column was washed with buffer A (20 mM sodium acetate, 1 mM EDTA, pH 5.5), followed by elution on a sodium chloride (NaCl) density gradient from 0 to 1M, to elute human cathepsin L near an NaCl concentration of about 0.4M. This fraction was applied to the Mono S column (HR5/5) of an FPLC system (produced by Pharmacia), followed by column washing and human cathepsin L elution in the same manner as above. The human cathepsin L fraction, eluted near an NaCl concentration of about 0.36M, was concentrated to yield a purified standard preparation.

Reference Example 8

(2S,3S)-Ethyl Hydrogen Trans-Epoxysuccinate

After (2S,3S)-trans-epoxysuccinic acid diethyl ester as described in Tetrahedron, Vol. 36, p. 87 (1980) (15.1 g) was dissolved in ethanol (500 ml), 1N aqueous sodium hydroxide (80.3 ml) was added under ice cooling conditions, followed by stirring for 2 hours. To the reaction mixture, water (100 ml) was added, followed by concentration. After the concentrate was adjusted to pH 2.5, sodium chloride was added to saturation, followed by extraction with ethyl acetate (150 ml×6). The ethyl acetate layer was washed with saturated saline (100 ml×4) and then dried over anhydrous sodium sulfate and concentrated, to yield the title compound (11.6 g) as a colorless oily substance (yield 90%).

$^1$H NMR δ ppm (CDCl$_3$) 1.33 (3H, t, J=7.2 Hz), 3.71 (1H, d, J=1.7 Hz), 3.72 (1H, d, J=1.6 Hz), 4.27 (1H, dd, J=7.1, 10.8 Hz), 4.31 (1H, dd, J=7.2, 10.8 Hz)

Reference Example 9

(2R,3R)-Methyl Hydrogen Trans-Epoxysuccinate

After (2R,3R)-trans-epoxysuccinic acid as described in Japanese Patent Unexamined Publication No. 277373/1987 (10.0 g) was dissolved in ethanol (100 ml), concentrate sulfuric acid (2.45 ml) was added, followed by refluxing with heating for 7 hours. After neutralization with saturated aqueous sodium hydrogen carbonate, the reaction mixture was concentrated and distributed with ethyl acetate-water. The ethyl acetate layer was washed with 2% aqueous sodium hydrogen carbonate, water and saturated saline and then dried over anhydrous sodium sulfate and concentrated, to yield (2R,3R)-transepoxysuccinic acid diethyl ester (10.4 g) as a colorless oily substance (yield 73%). After this substance was dissolved in methanol (500 ml), 1N aqueous sodium hydroxide (53.2 ml) was added under ice cooling conditions, followed by stirring for 2 hours. After the reaction mixture was concentrated and washed with ether (50 ml×2), it was adjusted to pH 2.0, after which sodium chloride was added to saturation, followed by extraction with ethyl acetate (200 ml×5). The ethyl acetate layer was washed with water and saturated saline, and then dried over anhydrous sodium sulfate and concentrated, to yield the title compound (6.27 g) as a colorless oily substance (yield 74%).

$^1$H NMR δ ppm (CDCl$_3$) 3.73 (1H, d, J=1.6 Hz), 3.74 (1H, d, J=1.6 Hz), 3.84 (3H, s), 8.74 (1H, br s)

Reference Example 10

N-Acetyl-N'-Z-1,4-Diaminobutane

After N-Z-1,4-diaminobutane as described in Hoppe-Seylers' Zeitschrift Physiolgische Chemie, Vol. 349, p. 251 (1968) (1.10 g) was dissolved in pyridine (5 ml), acetic anhydride (10 ml) and dichloromethane (5 ml) were added under ice cooling conditions, followed by stirring at room temperature for 24 hours. The reaction mixture was concentrated to dryness under reduced pressure. After ethyl acetate was added, the resulting solution was washed with saturated saline and then dried over anhydrous sodium sulfate, followed by silica gel column chromatography (100 ml) for elution with an eluent (methanol sequentially added to ethyl acetate), to yield the title compound (0.95 g) (yield 73%) from the fraction eluted with 0–20% (v/v) methanol.

$^1$H NMR δ ppm (CDCl$_3$) 1.44–1.60 (4H, m), 1.96 (3H, s), 3.20–3.35 (4H, m), 4.95 (1H, br), 5.09 (2H, s), 5.77 (1H, br), 7.28–7.40 (5H, m)

Reference Example 11

Preparation of Main Culture Broth

*Aspergillus* FL-47958 strain grown on potato-dextrose agar slant medium was inoculated to 40 ml of a seed medium (pH 7.0) containing 2% glucose, 3% soluble starch, 1% soybean flour, 0.3% corn steep liquor, 0.5% peptone, 0.3% sodium chloride and 0.5% calcium carbonate in a 200 ml conical flask, and cultured at 28° C. for 48 hours on a reciprocal shaker. 1 ml of this culture broth was transferred to 40 ml of a main medium containing 5% dextrin, 3% corn steep liquor, 0.5% polypepton, 1% calcium chloride and 0.5% calcium carbonate (pH 7.0) in a 200 ml conical flask, and cultured at 24° C. for 5 days on a rotary shaker, to yield the main culture broth.

Reference Example 12

TAN-1868 Monosodium Salt

Figure 15:
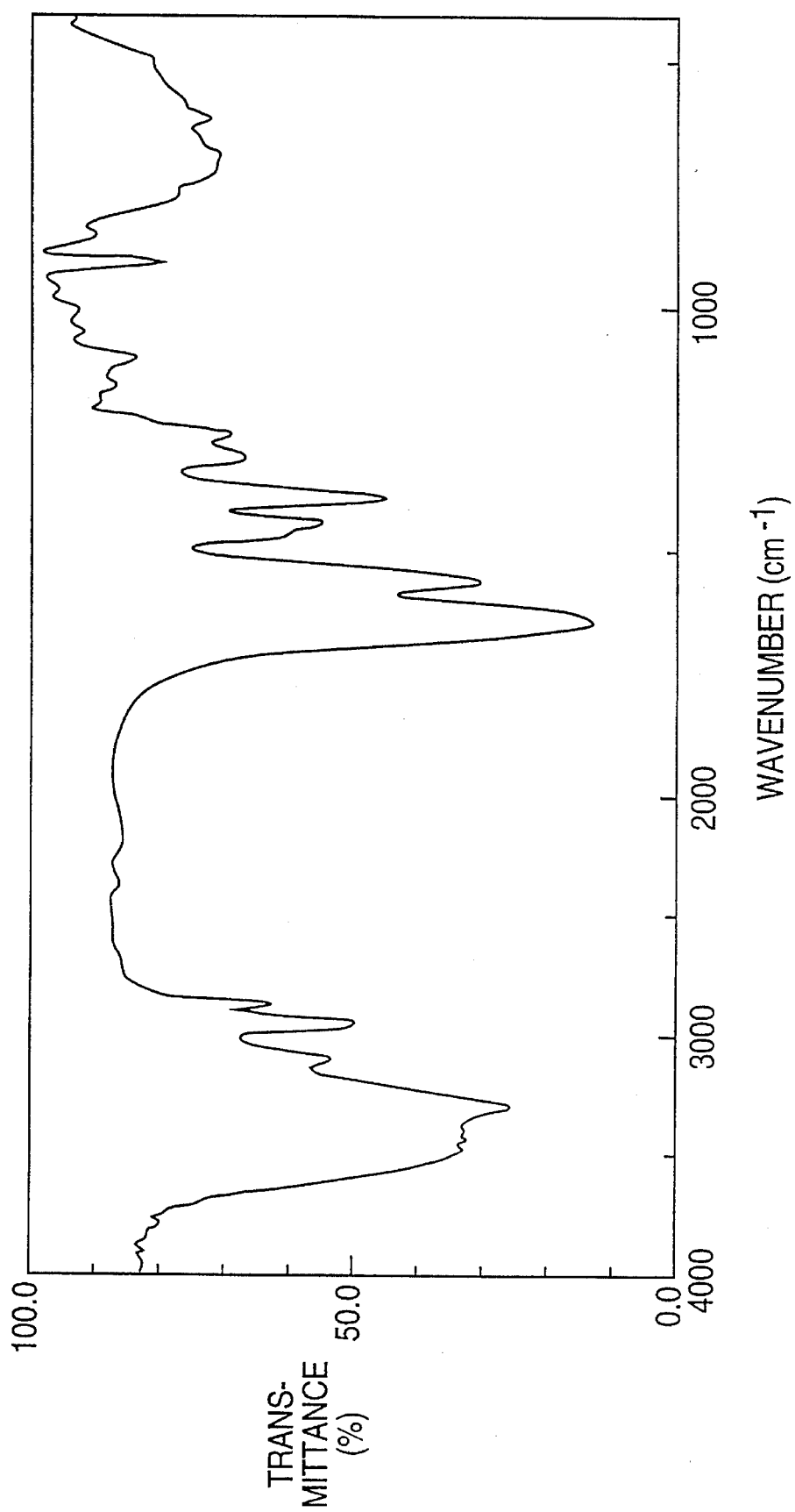
Figure 16:
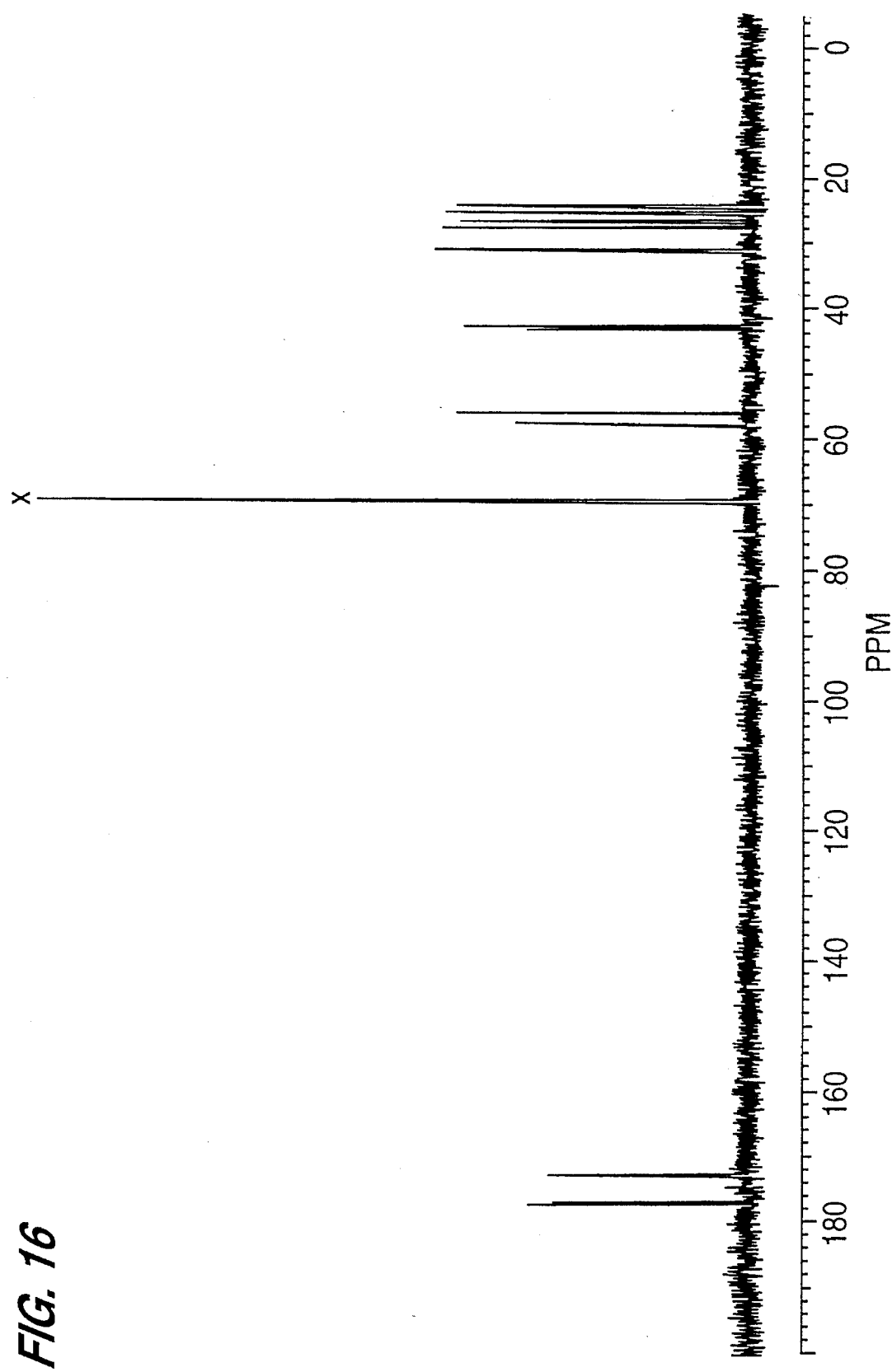

The culture broth (3.3 L) obtained in Reference Example 11 was filtered using a filter aid (Hyflo Super Cel, produced by Johns-Manville Products, USA). After adjustment to pit 7.0, the filtrate was subjected to column chromatography with Diaion HP-20 (200 ml), washed with water (600 ml) and then eluted with 50% (v/v) aqueous methanol (1,000 ml). The eluate was concentrated to 600 ml under reduced pressure, passed through a column packed with Amberlite IRA-68 (Cl type, 160 ml), washed with water (500 ml) and then eluted with 1M saline (800 ml). The eluate was subjected to column chromatography with Diaion HP-20 (50–100 mesh, 150 ml), washed with water (300 ml) and then sequentially eluted with water (300 ml) and 20% (v/v) aqueous methanol (300 ml). The eluate was concentrated, passed through a column packed with QAE-Sephadex A-25 (Cl type, 100 ml), washed with water (300 ml), and then eluted with 0.05M saline. After adjustment to pH 7.1, the active fraction (400 to 600 ml) was desalinized with Diaion HP-20 (50–100 mesh, 50 ml), to yield a crude powder (52 mg). This crude powder was subjected to preparative HPLC [column YMC-Pack, D-ODS-5 (S-5 120A); mobile phase 9% (v/v) acetonitrile/0.01M phosphate buffer (pH 6.3); flow rate 10 ml/min]. The fraction showing a single peak in analytical HPLC was collected, concentrated, and desalinized with Diaion HP-20 (50–100 mesh, 25 ml). The eluate was concentrated and lyophilized to yield N-acetyl-N'-{N-[(2S,3S)-3-trans-carboxyoxirane-2-carbonyl]-L-leucyl}-1, 5-diaminopentane monosodium salt (TAN-1868 monosodium salt) (compound 95; 27 mg).
1) Appearance: White powder
2) Optical rotation: +17° (c 0.53, water, 25° C.)
3) Molecular weight: m/z 394 (M+H)$^+$, 416 (M+Na)$^+$ (SI-mass spectrum)
4) Elemental analysis (%, 1.5 mol water assumed) Found: C, 48.97; H, 7.73; N, 10.17; Na, 5.70 Calculated: C, 48.57; H, 7.43; N, 9.99; Na, 5.47
5) Molecular formula: $C_{17}H_{28}N_3O_6Na$
6) UV spectrum in water: End absorption
7) IR spectrum (in KBr tablet, major absorptions shown, wave-number cm$^{-1}$, FIG. 15): 3290, 2940, 1650, 1560, 1440, 1390, 1300, 1260, 1100, 900
8) $^{13}C$ NMR spectrum (75 Mz, in heavy water, δ ppm, FIG. 16): 176.9 (Q), 176.3 (Q), 176.6 (Q), 172.5 (Q), 57.3 (CH), 55.8 (CH), 55.6 (CH), 42.8 (CH$_2$), 42.2 (CH$_2$), 42.1 (CH$_2$), 30.9 (CH$_2$), 30.8 (CH$_2$), 27.3 (CH), 26.2 (CH$_2$), 25.0 (CH$_3$), 24.8 (CH$_3$), 23.7 (CH$_3$)
9) Coloring reactions:
   Positive; peptide reaction, phosphomolybdic acid reaction
   Negative; ninhydrin reaction, Sakaguchi reaction, Ehrlich reaction
10) High performance liquid chromatography (HPLC):
   Column; YMC-Pack A-312, ODS
   Mobile phase; 10% (v/v) acetonitrile/0.01M phosphate buffer (pH 6.3)
   Flow rate; 2.0 ml/min
   Detection 214 nm
   Retention time; 9.2 minutes
11) Thin-layer chromatography (TLC): Carrier; Silica gel 60F254 (produced by Merck, Germany) Developing solvent (by volume); n-butanol:acetic acid:water (2:1:1) Rf value; 0.64

EXAMPLE 1

Preparation of Main Culture Broth

*Chaetomium globosum* FL-41927 strain grown on potato-dextrose agar slant medium was inoculated to 500 ml of a seed medium (pH 7.0) containing 2% glucose, 3% soluble starch, 1% soybean flour, 0.3% corn steep liquor, 0.5% peptone, 0.3% sodium chloride and 0.5% calcium carbonate in a 2 L Sakaguchi flask, and cultured at 28° C. for 48 hours on a reciprocal shaker. 500 ml of this culture broth was transferred to 120 liters of a main medium containing 5% soluble starch, 1.5% corn gluten meal, 0.3% beer yeast, 1% magnesium sulfate, 0.7% potassium dihydrogen phosphate, 2% disodium hydrogen phosphate and 0.7% calcium carbonate (pH not modified) in a 200 liter stainless steel tank. The fermentation was carried out 28° C. with aeration of 120 liters/min, agitation of 180 rpm and an inner pressure of 1 kg/cm$^2$ for 5 days to yield the main culture broth.

EXAMPLE 2

TAN-1756A and TAN-1756B

The culture broth (220 L) obtained in Example 1 was filtered using a filter aid (Radiolite 600, produced by Showa Chemical Industry). After adjustment to pit 7.0, the filtrate (190 L) was subjected to column chromatography with activated carbon (4 L), washed with water (15 L) and then eluted with 8% (v/v) aqueous isobutanol (40 L). After adjustment to pH 7, the eluate was passed through a column packed with Amberlite IRA-402 (OH type, 4 L), washed with water (15 L) and then eluted with 1M saline (40 L). After adjustment to pH 7, the eluate was subjected to column chromatography with Diaion HP-20 (10 L), washed with water (30 L) and then eluted with 50% (v/v) aqueous methanol (40 L). The eluate was concentrated under reduced pressure, passed through a column packed with Amberlite IRA-402 (Cl type, 500 ml), and washed with water (1 L). The effluent was combined with washings, followed by concentration and lyophilization, to yield a crude powder (11.4 g).

The resulting crude powder was dissolved in water (20 ml) and then subjected to column chromatography with microcrystalline cellulose (Funacel, 500 ml) for sequential elution with acetonitrile (1 L), acetonitrile: water [90:10 (1.5 L, fractions 3–5), 85:15 (2.5 L, fractions 6–10), 80:20 (3 L, fractions 11–16), 70:30 (1.5 L, fractions 17–19)], to yield 500 ml fractions, which were divided into three combined fractions: fraction Nos. 9–12, 13–16 and 17–19. After concentration, each fraction was lyophilized to yield powder I (3.13 g), powder II (2.74 g) and powder III (1.98 g), all containing TAN-1756A and B. Powder II was further subjected to column chromatography with microcrystalline cellulose (Funacel, 200 ml) for sequential elution with acetonitrile (400 ml), acetonitrile: water [90:10 (600 ml), 85:15 (1800 ml), 80:20 (1000 ml)]. The fraction eluted with acetonitrile: water [85:15 (800–1800 ml)]was concentrated and lyophilized to yield power IV (1.56 g) containing TAN-1756A. Separately, the fraction eluted with acetonitrile: water [80:20 (0–800 ml)] was concentrated; the resulting crystal was collected by filtration to yield crystals (239 mg) of N-{N[(2S,3S )-3-trans-carboxyoxirane-2-carbonyl]-

L-tyrosyl}-1,4-diaminobutane [TAN-1756B (compound 2)]. The mother liquor was concentrated and then lyophilized to yield powder V (659 mg) containing TAN-1756B.

Powders I and III were combined together and subjected to two cycles of the same procedure of column chromatography with microcrystalline cellulose as above, to yield powder VI (2.6 g) containing TAN-1756A and powder VII (361 mg) containing TAN-1756B.

Powders IV and VI, both containing TAN-1756A, were subjected to preparative HPLC [column YMC-Pack, S-363–15, ODS; mobile phase 5% (v/v) aqueous acetonitrile; flow rate 20 ml/min]; the fraction showing a single peak in analytical HPLC was collected, concentrated and then lyophilized to yield a powder (181 mg) of N-{N-[(2S, 3S)-3-trans-carboxyoxirane-2-carbonyl]-L-phenylalanyl}-1,4-diaminobutane [TAN-1756A (compound 1)].

Powders V and VII, both containing TAN-1756B, were subjected to preparative HPLC [column YMC-Pack, S-363–15, ODS; mobile phase 2% (v/v) aqueous acetonitrile; flow rate 20 ml/min]; the fraction showing a single peak in analytical HPLC was collected, concentrated, and the resulting crystal was collected by filtration, to yield crystals (307 mg) of TAN-1756B (compound 2).

TAN-1756A

Figure 2:
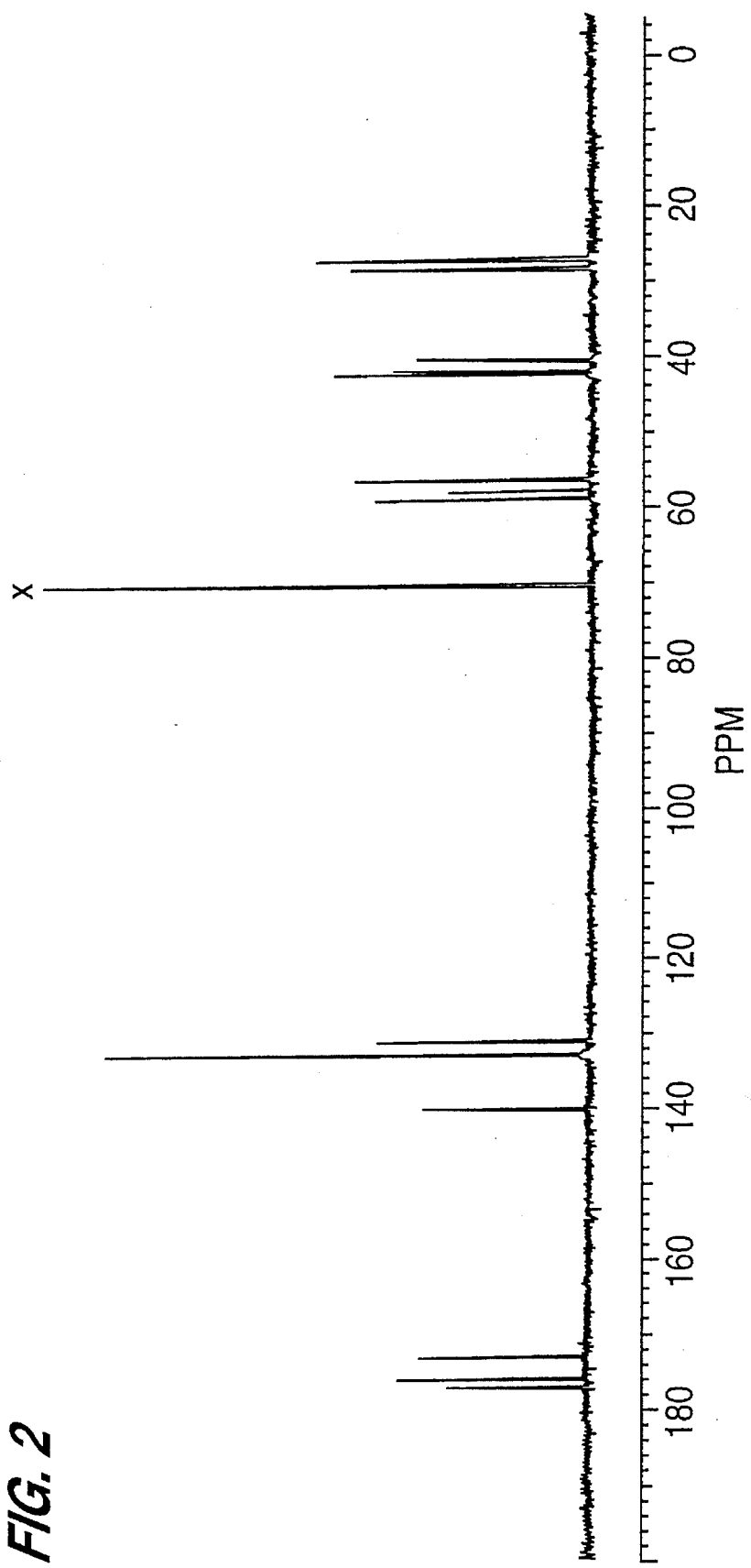
FIG. 2 is the $^{13}$C-NMR spectrum of TAN-1756A.

1) Appearance: White powder
2) Optical rotation: +53° (c 0.50, 0.1N hydrochloric acid, 25° C.)
3) Molecular weight: m/z 350 (M+H)$^+$, (SI-mass spectrum)
4) Elemental analysis (%, 1.5 mol water assumed) Found: C, 54.46; H, 6.40; N, 10.87 Calculated: C, 54.25; H, 6.96; N, 11.16
5) Molecular formula: $C_{17}H_{23}N_3O_5$
6) UV spectrum in water:
   Maximum; 257 nm ($\epsilon$ 300, shoulder)
7) IR spectrum (in KBr tablet, major absorptions shown, wave-number cm$^{-1}$, FIG. 1): 3280, 3080, 2930, 1650, 1600, 1560, 1450, 1390, 1310, 1240, 890, 700
8) $^{13}$C NMR spectrum (75 Mz, in heavy water, 3 ppm, FIG. 2): 176.5 (Q), 175.4 (Q), 172.4 (Q), 139.2 (Q), 132.1×2 (CH), 131.7×2 (CH), 130.2 (CH), 58.2 (CH), 57.3 (CH), 55.7 (CH), 42.0 ($CH_2$), 41.4 ($CH_2$), 39.9 ($CH_2$), 28.2 ($CH_2$), 27.0 ($CH_2$)
9) Coloring reactions:
   Positive; ninhydrin reaction, peptide reaction, phosphomolybdic acid reaction
   Negative; Sakaguchi reaction, Ehrlich reaction
10) High performance liquid chromatography (HPLC):
    Column; YMC-Pack A-312, ODS
    Mobile phase; 5% (v/v) acetonitrile/0.01M phosphate buffer (pH 6.3)
    Flow rate; 2.0 ml/min
    Detection; 214 nm
    Retention time; 15.5 minutes
11) Thin-layer chromatography (TLC):
    Carrier; Silica gel 60F$_{254}$ (produced by Merck, Germany)
    Developing solvent; n-butanol:acetic acid:water (2:1:1) (by volume)
    Rf value; 0.49

TAN-1756B

Figure 3:
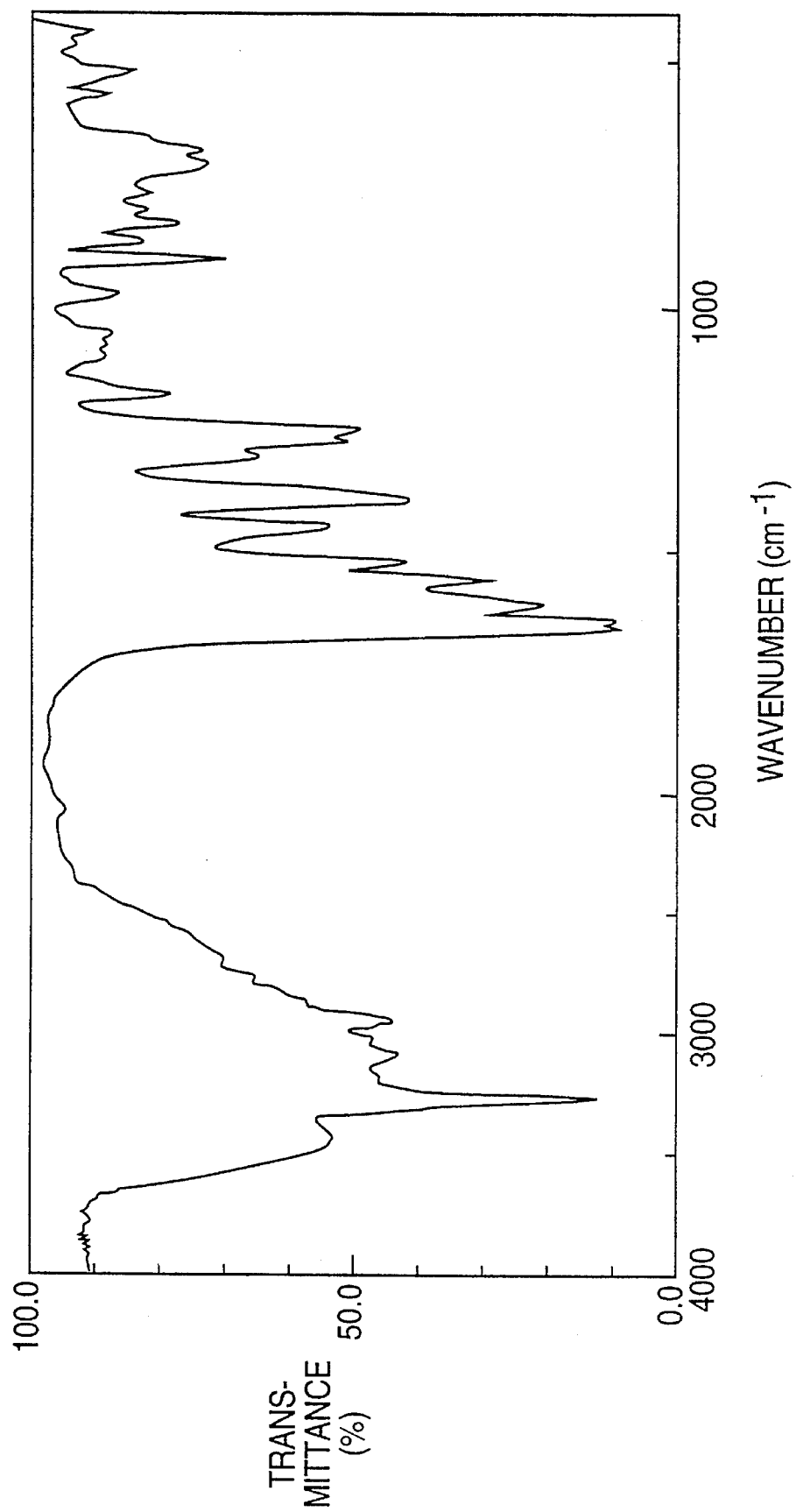
FIG. 3 is the IR spectrum of TAN-1756B.
Figure 4:
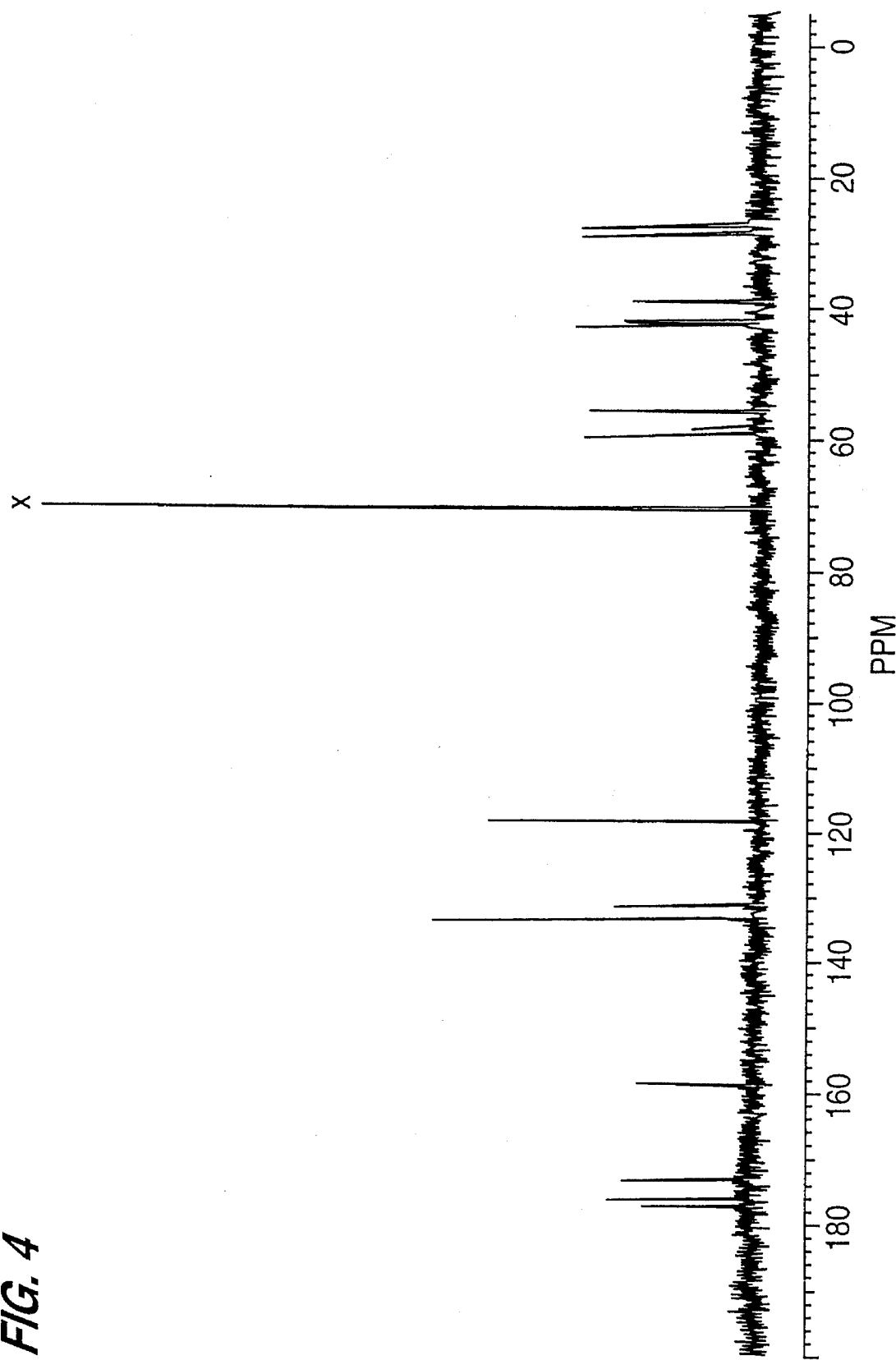
FIG. 4 is the $^{13}$C-NMR spectrum of TAN-1756B.

1) Appearance: Colorless crystals
2) Melting point: 116°–118° C.
3) Optical rotation: +60° (c 0.53, 0.1N hydrochloric acid, 25° C.)
4) Molecular weight: m/z366 (M+H)$^+$, (SI-mass spectrum)
5) Elemental analysis (%, 0.5 mol water assumed) Found: C, 54.56; H, 6.37; N, 11.30 Calculated: C, 54.54; H, 6.46; N, 11.22
6) Molecular formula: $C_{17}H_{23}N_3O_6$
7) UV spectrum in water:
   Maximum; 221 nm ($\epsilon$ 10,400), 273 nm ($\epsilon$ 1,300)
8) IR spectrum (in KBr tablet, major absorptions shown, wave-number cm$^{-1}$, FIG. 3): 3280, 3090, 2950, 1660, 1650, 1610, 1560, 1520, 1440, 1390, 1270, 1240, 1170, 900, 700
9) $^{13}$C NMR spectrum (75 Mz, in heavy water, $\delta$ ppm, FIG. 4): 176.5 (Q), 175.5 (Q), 172.4 (Q), 157.8 (q), 133.5×2 (CH), 130.7 (Q), 118.6×2 (CH), 58.5 (CH), 57.2 (CH), 55.7 (CH), 42.0 ($CH_2$), 41.4 ($CH_2$), 39.0 ($CH_2$), 28.2 ($CH_2$), 27.0 ($CH_2$)
10) Coloring reactions:
    Positive; ninhydrin reaction, peptide reaction, phosphomolybdic acid reaction
    Negative; Sakaguchi reaction, Ehrlich reaction
11) High performance liquid chromatography (HPLC):
    Column; YMC-Pack A-312, ODS
    Mobile phase; 5% (v/v) acetonitrile/0.01M phosphate buffer (pH 6.3)
    Flow rate; 2.0 ml/min
    Detection; 214 nm, 254 nm
    Retention time; 5.2 minutes
12) Thin-layer chromatography (TLC):
    Carrier; Silica gel 60F$_{254}$ (produced by Merck, Germany)
    Developing solvent; n-butanol:acetic acid:water (2:1:1) (by volume)
    Rf value; 0.41

EXAMPLE 3

Preparation of Main Culture Broth

*Tolypocladium cylindrosporum* FL-43974 strain grown on potato-dextrose agar slant medium was inoculated to 500 ml of a seed medium (pH 7.0) containing 2% glucose, 3% soluble starch, 1% soybean flour, 0.3% corn steep liquor, 0.5% peptone, 0.3% sodium chloride and 0.5% calcium carbonate in a 2 L Sakaguchi flask, and cultured at 28° C. for 48 hours on a reciprocal shaker. 500 ml of this culture broth was transferred to 120 liters of a main medium containing 5% dextrin, 3% corn steep liquor, 0.5% polypepton, 1% calcium chloride and 0.5% calcium carbonate (pH 7.0) in a 200 liter stainless steel tank. The fermentation was carried out at 24° C. with aeration of 120 liters/min, agitation of 180 rpm and an inner pressure of i kg/cm$^2$ for 5 days to yield the main culture broth.

EXAMPLE 4

TAN-1854A Monohydrochloride and TAN-1854B Monohydrochloride

The culture broth (225 L) obtained in Example 3 was filtered using a filter aid (Radiolite 600). After adjustment to pH 7.0, the filtrate (218 L) was subjected to column chromatography with activated carbon (8 L), washed with water (24 L) and then eluted with 8% (v/v) aqueous isobutanol (80 L). The eluate was concentrated under reduced pressure, passed through a column packed with Amberlite IRC-50 (H type, 14 L), washed with water (42 L) and then eluted with 1M saline (70 L). After adjustment to pH 7.0, the eluate was subjected to column chromatography with Diaion HP-20 (30 L), washed with water (90 L) and then eluted with 50% (v/v) methanol/0.01M hydrochloric acid (90 L). After adjustment to pit 7.0, the eluate was concentrated under reduced pressure, subjected to column chromatography with Diaion HP-20 (100–200 mesh, 600 ml), and washed with water (900 ml), followed by sequential elution with water (900 ml), 50% (v/v) aqueous methanol (820 ml) and 50% (v/v) methanol/0.005N hydrochloric acid (900 ml). The eluate was concentrated, passed through a column packed with CM-Sephadex C-25 (Na type, 300 ml), and washed with water (900 ml), after which it was eluted and fractionated with 0.05M saline. The resulting fractions were divided into two combined fractions: a fraction dominated by TAN-1854A (2.4–3.0 L) and a fraction containing both TAN-1854A and TAN-1854B (3.0–3.9 L). Each fraction was desalinized with Diaion HP-20 (100–200 mesh). The eluate was concentrated and lyophilized to yield a powder (251 mg) containing TAN-1854A and another powder (259 mg) containing both TAN-1854A and TAN-1854B.

The powder (257 mg) containing both TAN-1854A and TAN-1854B was subjected to preparative HPLC [column YMC-Pack, S-363-15, ODS; mobile phase 1–3% (v/v) acetonitrile/0.02M phosphate buffer (pH 3.0); flow rate 20 ml/min]. The eluate was thus fractionated into two fractions: a fraction showing a single peak of TAN-1854A in analytical HPLC [fraction (I)] and another fraction showing a single peak of TAN-1854B in analytical HPLC [fraction (II)]. Fraction (II) was passed through a column packed with Amberlite IRA-402 (Cl type, 40 ml), and washed with water (40 ml). The effluent was combined with washings, and the mixture was concentrated and then desalinized with Diaion HP-20 (100–200 mesh, 50 ml). The eluate was concentrated and then lyophilized to yield N-{N-[(2S,3S)-3-transcarboxyoxirane-2-carbonyl]-L-tyrosyl}-N-(3-aminopropyl)-1, 4-diaminobutane monohydrochloride (TAN-1854B monohydrochloride) (compound 4; 99 mg).

The powder containing TAN-1854A (248 mg) was subjected to preparatory HPLC [column YMC-Pack, S-363-15, ODS; mobile phase 3% (v/v) acetonitrile/0.02 M phosphate buffer (pH 3.0); flow rate 20 ml/min]; the fraction showing a single peak in analytical HPLC was collected. This fraction was combined with fraction (I) described above, and the mixture was passed through a column packed with Amberlite IRA-402 (Cl type, 100 ml) and washed with water (100 ml). The effluent was combined with washings, and the mixture was concentrated and then desalinized with Diaion HP-20 (100–200 mesh, 50 ml). The eluate was concentrated and then lyophilized to yield N-{N-[(2S,3S)-3-trans-carboxyoxirane-2-carbonyl]-L-phenylalanyl}-N-(3-aminopropyl)-1,4-diaminobutane monohydrochloride (TAN-1854A monohydrochloride) (compound 3; 143 mg).

TAN-1854A monohydrochloride

Figure 5:
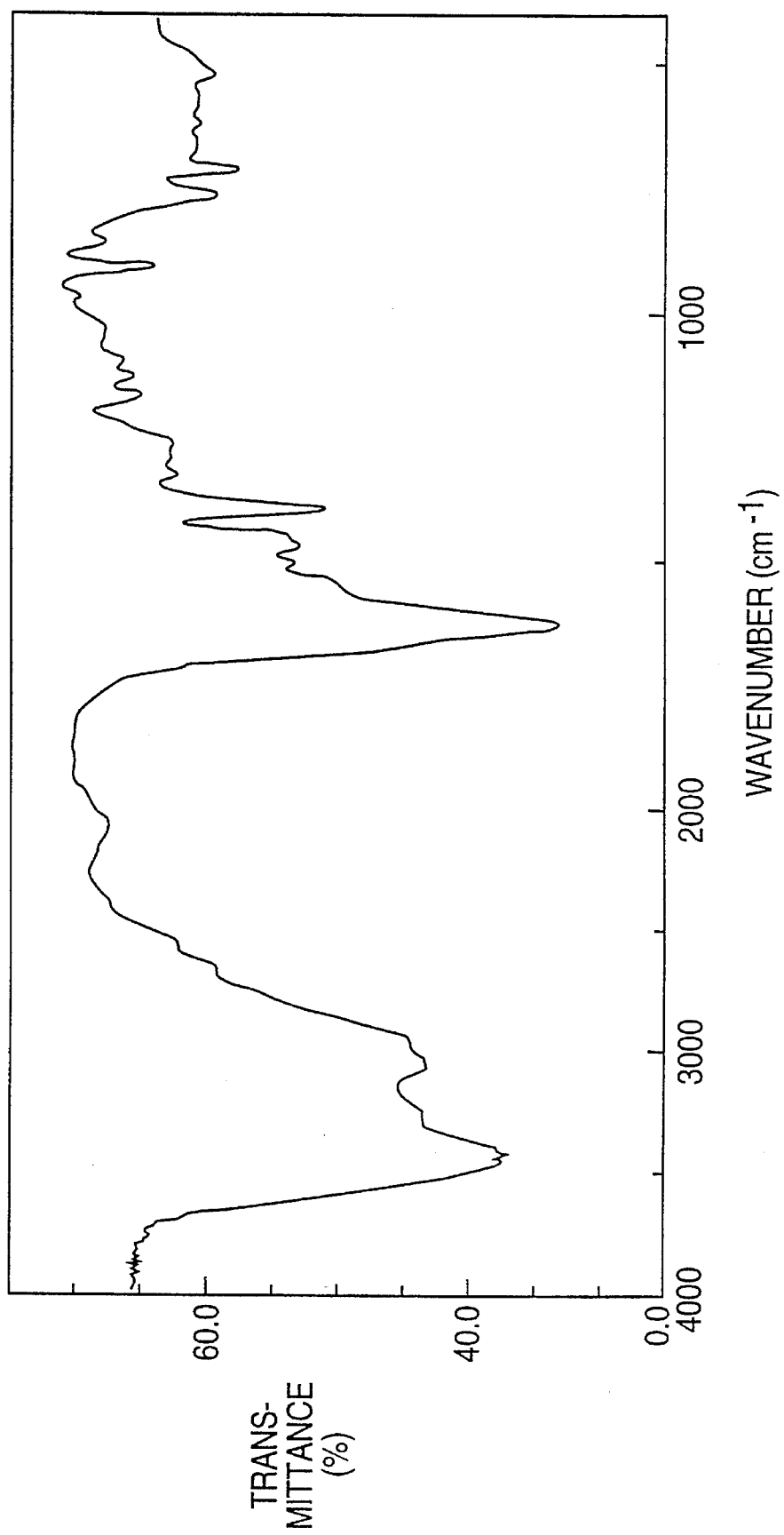
FIG. 5 is the IR spectrum of TAN-1854A monohydrochloride.
Figure 6:
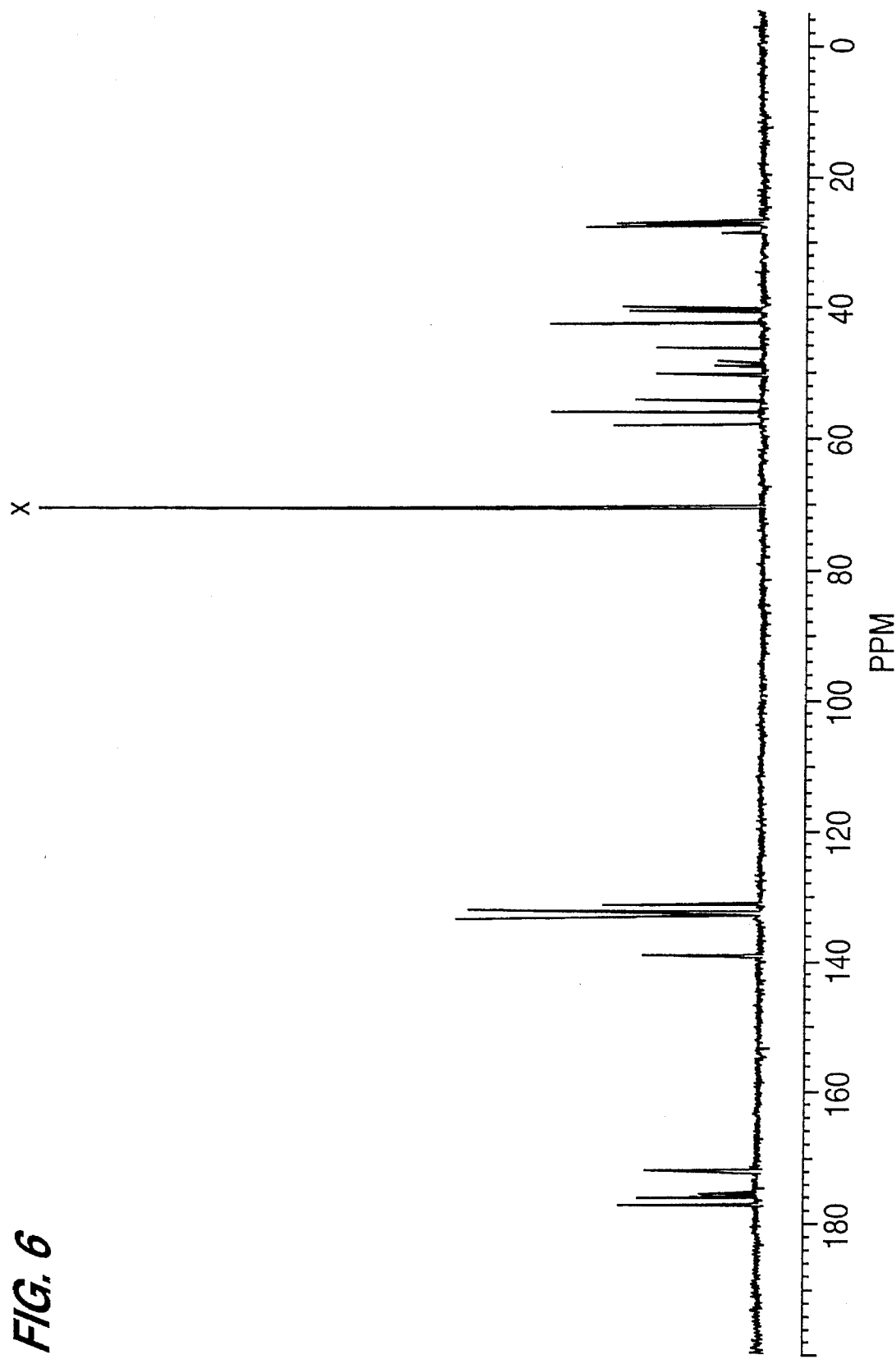
FIG. 6 is the $^{13}$C-NMR spectrum of TAN-1854A monohydrochloride.

1) Appearance: White powder
2) Optical rotation: +43° (c 0.52, 0.1 N hydrochloric acid, 24° C.)
3) Molecular weight: m/z 407 (M+H)$^+$, (SI-mass spectrum)
4) Elemental analysis (%, 1 mol water assumed) Found: C, 51.97; H, 7.15; N, 12.12; Cl, 8.87 Calculated: C, 52.11; H, 7.22; N, 12.15; Cl, 7.69
5) Molecular formula: $C_{20}H_{30}N_4O_5 \cdot HCl$
6) UV spectrum in water:
   Maximum; 257 nm (ε200, shoulder)
7) IR spectrum (in KBr tablet, major absorptions shown, wavenumber cm$^{-1}$, FIG. 5): 3430, 3260, 3060, 1630, 1380, 900, 750, 700
8) $^{13}$C NMR spectrum (75 Mz, in heavy water, δ ppm. TAN-1854A occurs as a mixture of two conformers in heavy water; the signal for the major conformer is shown. FIG. 6): 176.5 (Q), 175.5 (Q), 171.8 (Q), 138.8 (Q), 132.4×2 (CH), 131.8×2 (CH), 130.4 (CH), 57.2 (CH), 55.6 (CH), 54.1 (CH), 50.2 ($CH_2$), 46.1 ($CH_2$), 42.0 ($CH_2$), 40.5 ($CH_2$), 39.8 ($CH_2$), 27.8×2 ($CH_2$), 26.9 ($CH_2$)
9) Coloring reactions:
   Positive; ninhydrin reaction, peptide reaction, phosphomolybdic acid reaction
   Negative; Sakaguchi reaction, Ehrlich reaction
10) High performance liquid chromatography (HPLC):
    Column; YMC-Pack A-312, ODS
    Mobile phase; 5% (v/v) acetonitrile/0.01 M phosphate buffer (pH 3.0)
    Flow rate; 2.0 ml/min
    Detection; 214 nm
    Retention time; 7.2 minutes
11) Thin-layer chromatography (TLC):
    Carrier; Silica gel 60F254 (produced by Merck, Germany)
    Developing solvent; n-butanol:acetic acid:water (2:1:1) (by volume)
    Rf value; 0.20

TAN-1854B monohydrochloride

Figure 7:
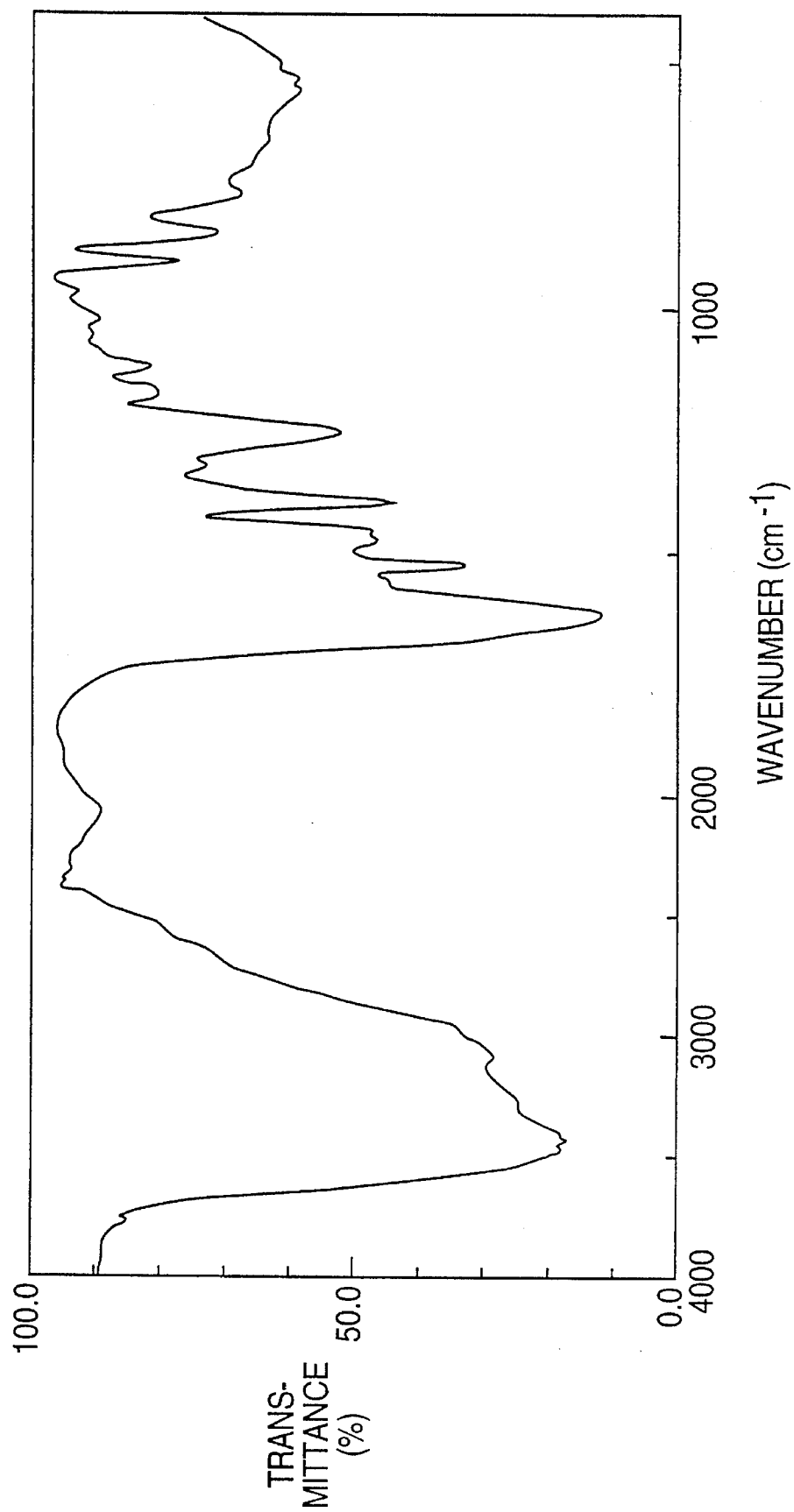
FIG. 7 is the IR spectrum of TAN-1854B monohydrochloride.
Figure 8:
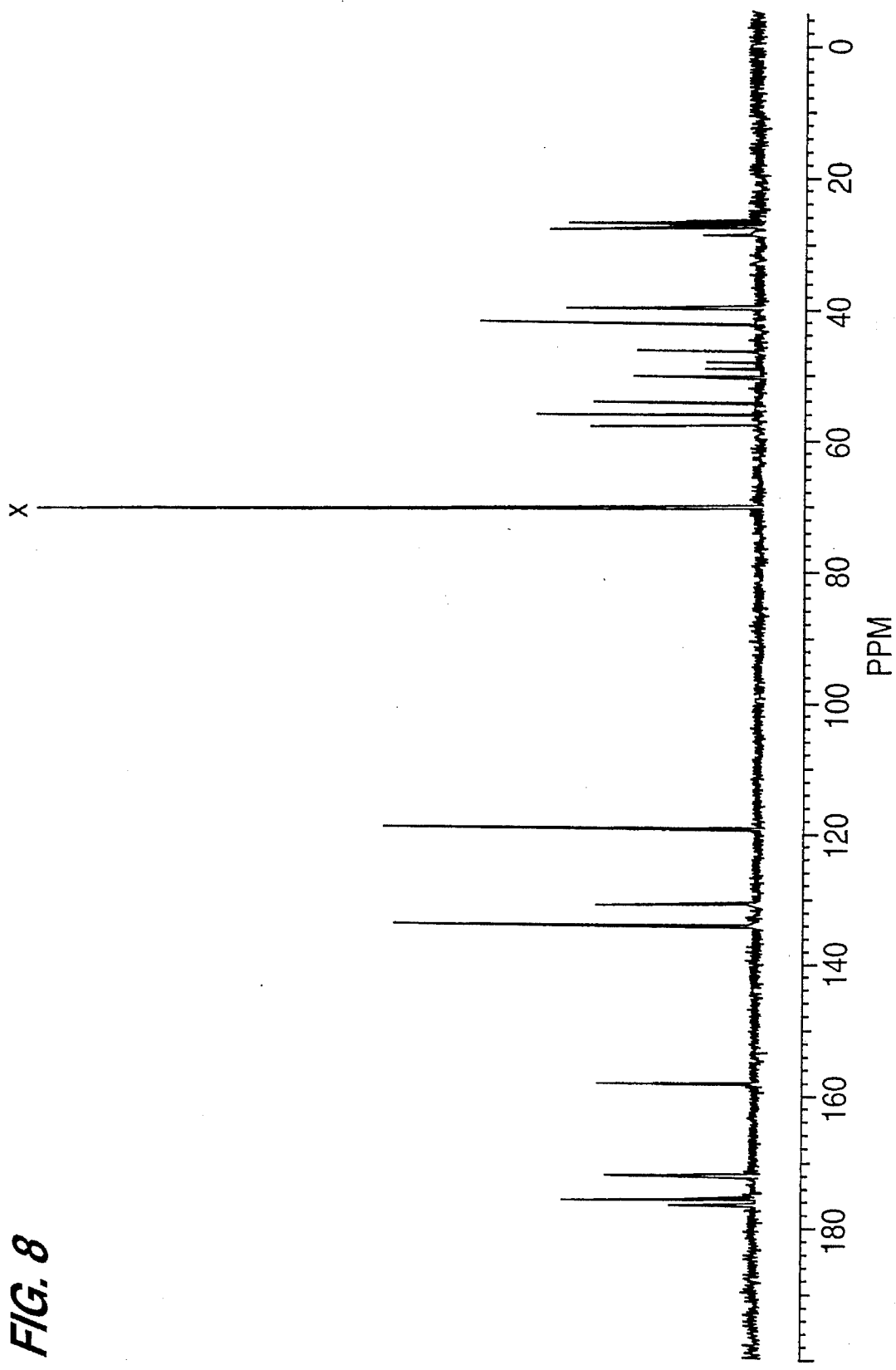
FIG. 8 is the $^{13}$C-NMR spectrum of TAN-1854B monohydrochloride.

1) Appearance: White powder
2) Optical rotation: +40° (c 0.52, 0.1 N hydrochloric acid, 24° C.)
3) Molecular weight: m/z 423 (M+H)$^+$, (SI-mass spectrum)
4) Elemental analysis (%, 1.5 mol water assumed) Found: C, 49.25; H, 6.92; N, 11.44; Cl, 8.97 Calculated: C, 49.43; H, 7.05; N, 11.53; Cl, 7.30
5) Molecular formula: $C_{20}H_{30}N_4O_6 \cdot HCl$
6) UV spectrum in water:
   Maximum; 221 nm (ε10,300), 273 nm (ε1,100)
7) IR spectrum (in KBr tablet, major absorptions shown, wavenumber cm$^{-1}$, FIG. 7): 430, 3260, 3070, 1620, 1520, 1380, 1240, 900, 840
8) $^{13}$C NMR spectrum (75 Mz, in heavy water, 3 ppm. TAN-1854B occurs as a mixture of two conformers in heavy water; the signal for the main conformer is shown. FIG. 8): 176.5 (Q), 175.7 (Q), 171.7 (Q), 157.9 (Q), 133.8×2 (CH), 130.5 (Q), 118.6×2 (CH), 57.2 (CH), 55.6 (CH), 54.3 (CH), 50.2 ($CH_2$), 46.1 ($CH_2$), 42.0 ($CH_2$), 39.8 ($CH_2$), 39.7 ($CH_2$), 27.8 ($CH_2$), 27.7 ($CH_2$), 27.0 ($CH_2$)
9) Coloring reactions:
   Positive; ninhydrin reaction, peptide reaction, phosphomolybdic acid reaction
   Negative; Sakaguchi reaction, Ehrlich reaction
10) High performance liquid chromatography (HPLC):
    Column; YMC-Pack A-312, ODS
    Mobile phase; 5% (v/v) acetonitrile/0.01 M phosphate buffer (pH 3.0)
    Flow rate; 2.0 ml/min
    Detection; 214 nm
    Retention time; 2.9 minutes
11) Thin-layer chromatography (TLC):
    Carrier; Silica gel 60F$_{254}$ (produced by Merck, Germany)

Developing solvent; n-butanol:acetic acid:water (2:1:1) (by volume)
Rf value; 0.19

EXAMPLE 5

N-Z-N'-[N-[(2S,3S)-3-trans-ethoxycarbonyloxirane-2-carbonyl]-L-phenylalanyl)-1,4-diaminobutane After N-Z-1,4-diaminobutane (1.00 g) and Boc-L-Phe-OH (1.31 g, produced by Peptide Institute, Inc.) were dissolved in dichloromethane (30 ml), HOBT (669 rag) and WSC (949 rag) were added under ice cooling conditions, followed by stirring at room temperature for 14 hours. After addition of ethyl acetate (200 ml), the reaction mixture was washed with 10% aqueous citric acid, water, 2% aqueous sodium hydrogen carbonate, water and saturated saline, and then dried over anhydrous sodium sulfate. The dry product was subjected to silica gel column chromatography (Kieselgel 60, produced by E. Merck, Germany, 200 ml) for elution with a chloroform eluent supplemented with sequentially added methanol, to yield N-(Boc-L-phenylalanyl)-N'-Z-1,4-diaminobutane (1.89 g) from the fraction eluted with 3% methanol (yield 90%). To this compound, trifluoroacetic acid (TFA, 19 ml) was added; the mixture was kept standing for 2 hours and then concentrated, to eliminate the Boc group. After the concentrate was dissolved in dichloromethane (50 ml), (2S,3S)-ethyl hydrogen trans-epoxysuccinate as obtained in Reference Example 8 (709 mg), triethylamine (1.25 ml), HOBT (599 mg) and WSC (849 mg) were added under ice cooling conditions, followed by stirring at room temperature for 14 hours. After addition of chloroform, the reaction mixture was washed with 10% aqueous citric acid, water, saturated aqueous sodium hydrogen carbonate, 2% aqueous sodium hydrogen carbonate, water and saturated saline, and then dried over anhydrous sodium sulfate. The dry product was subjected to silica gel column chromatography (200 ml) for elution with a chloroform eluent supplemented with sequentially added methanol, to yield the title compound (compound 5; 980 mg) as a white powder (yield 48%) from the fraction eluted with 1–2% (v/v) methanol.

$[\alpha]_D^{26}$ +22° (c 0.51, CHCl$_3$)

Elemental analysis (for $C_{27}H_{33}N_3O_7 \cdot 0.6H_2O$): Calculated: C; 62.08, H; 6.60, N; 8.04 Found: C; 61.94, H; 6.44, N; 8.13

$^1$H NMR δ ppm (CDCl$_3$) 1.30 (3H, t, J=7.1 Hz), 1.41 (4H, m), 3.03 (2H, m), 3.12 (1H, d, J=1.9 Hz), 3.17 (4H, m), 3.62 (1H, d, J=1.9 Hz), 4.24 (2H, m), 4.55 (1H,m), 4.85 (1H, br s), 5.10 (2H, s), 6.00 (1H, br s), 6.73 (1H, br d, J =8.0 Hz), 7.15–7.38 (10H, m)

EXAMPLE 6

N-Z-N'-{N-[(2S,3S)-3-trans-carboxyoxirane-2-carbonyl]-L-phenylalanyl}-1,4-diaminobutane After compound 5 (900 mg) was dissolved in methanol (100 ml), 1N aqueous sodium hydroxide (1.94 ml, 1.1 equivalents) was added under ice cooling conditions, followed by stirring at room temperature for 3 hours. After the reaction mixture was concentrated, water was added. After adjustment to pH 2.0, the mixture was extracted with ethyl acetate (200 ml×3). The ethyl acetate layer was washed with water and saturated saline, dried over anhydrous sodium sulfate, and then concentrated, to yield the title compound (compound 6; 790 mg) as a white powder (yield 93%).

Elemental analysis (for $C_{25}H_{29}N_3O_7 \cdot 0.4H_2O$): Calculated: C; 61.19, H; 6.12, N; 8.56 Found: C; 61.24, H; 6.00, N; 8.75

$^1$H NMR δ ppm (DMSO-d$_6$) 1.34 (4H, m), 2.79 (1H, dd, J=9.5, 13.6 Hz), 2.93–3.12 (5H, m), 3.28 (1H, d, J=1.8 Hz), 3.58 (1H, d, J=1.8 Hz), 4.50 (1H, dr, J=5.2, 8.9 Hz), 5.00 (2H, s), 7.15–7.40 (11H, m), 8.08 (1H, t, J=5.5 Hz), 8.59 (1H, d, J=8.6 Hz)

EXAMPLE 7

TAN-1756A

After compound 6 (730 mg) was dissolved in methanol (50 ml), water (20 ml) and palladium/activated charcoal [10% (w/w), produced by Engelhard K.K., 80 mg] were added, followed by stirring at room temperature for 2 hours in hydrogen atmosphere. After the catalyst was filtered off, the filtrate was concentrated and lyophilized to yield TAN-1756A (compound 1; 460 mg) as a white powder (yield 87%).

The physico-chemical data on this compound agreed with those on the compound obtained from the culture broth.

EXAMPLE 8

N-Z-N'-{O-benzyl-N-[(2S,3S)-3-trans-ethoxycarbonyloxirane-2-carbonyl]-L-tyrosyl{-1,4-diaminobutane N-Z-1,4-diaminobutane (1.10 g) and Boc-L-Tyr(Bzl)-OH (2.02 g, produced by Peptide Institute, Inc.) were condensed together in the same manner as in Example 5 to yield N-(O-benzyl-Boc-L-tyrosyl)-N'-Z-1,4-diaminobutane (3.01 g) as a white powder (yield quantitative). After Boc group elimination with TFA, the powder was condensed with (2S,3S)-ethyl hydrogen trans-epoxysuccinate as obtained in Reference Example 8 (628 mg) to yield the title compound (compound 7; 1.46 g) as a white powder (yield 66%).

$[\alpha]_D^{26}$+25° (c0.57, CHCl$_3$)

Elemental analysis (for $C_{34}H_{39}N_3O_8 \sim 0.2 CHCl_3$): Calculated: C; 64.02, H; 6.16, N; 6.55 Found: C; 63.99, H; 6.05, N; 6.40

$^1$H NMR δ ppm (CDCl$_3$) 1.29 (3H, t, J=7.1 Hz), 1.41 (4H, m), 2.97 (2H, m), 3.16 (4H, m), 3.20 (1H, d, J=1.9 Hz), 3.64 (1H, d, J=1.9 Hz), 4.24 (2H, m), 4.50 (1H, m), 4.88 (1H, br s), 5.03 (2H, s), 5.09 (2H, s), 5.98 (1H, br s), 6.73 (1H, br d, J=8.1 Hz), 6.91 (2H, d, J=8.7 Hz), 7.08 (2H, d, J=8.7 Hz), 7.27–7.44 (10H, m)

EXAMPLE 9

N-Z-N'-{O-benzyl-N-[(2S,3S)-3-trans-carboxyoxirane-2-carbonyl]-L-tyrosyl}-1,4-diaminobutane Compound 7 (1.35 g) was subjected to alkali hydrolysis in the same manner as in Example 6 to yield the title compound (compound 8; 1.22 g) as a white powder (yield 95%).

Elemental analysis (for $C_{32}H_{35}N_3O_8 \cdot 0.25H_2O$): Calculated: C; 64.69, H; 6.02, N; 7.07 Found: C; 64.57, H; 5.85, N; 6.93

$^1$H NMR δ ppm (DMSO-d$_6$) 1.35 (4H, m), 2.73 (1H, dd, J=9.5, 13.5 Hz), 2.91 (1H, dd, J=5.4, 13.7 Hz), 2.98 (4H, m), 3.29 (1H, d, J=1.8 Hz), 3.58 (1H, d, J=1.8 Hz), 4.44 (1H, dt, J=5.6, 8.8 Hz), 5.00 (2H, s), 5.05 (2H, s), 6.91 (2H, d, J=8.6

Hz), 7.14 (2H, d, J=8.6 Hz), 7.24 (1H, t, J=5.6 Hz), 7.26–7.46 (10H, m), 8.08 (1H, t, J=5.5 Hz), 8.56 (1H, d, J=8.6 Hz)

EXAMPLE 10

TAN-1756B

Compound 8 (1.10 g) was subjected to catalytic reduction to eliminate the Z group in the same manner as in Example 7, after which it was purified by preparative high performance liquid chromatography [column, YMC-Pack S-363-15 I-15 ODS; mobile phase, 2.5% (v/v) aqueous acetonitrile; flow rate, 20 ml/min; detection wavelength, 214 nm]. The major peak was collected, concentrated and lyophilized to yield TAN-1756B (compound 2; 306 mg) as a white powder (yield 45%).

The physico-chemical data on this compound agreed with those on the compound obtained from the culture broth.

EXAMPLE 11

N-Z-N'-{N-[(2S,3S)-3-trans-ethoxycarbonyloxirane-2-carbonyl]-D-phenylalanyl}-1,4-diaminobutane N-Z-1,4-diaminobutane (1.00 g) and Boc-D-Phe-OH (1.31 g) were condensed together in the same manner as in Example 5 to yield N-(Boc-D-phenylalanyl)-N'-Z-1,4-diaminobutane (1.76 g) as a white powder (83.4%). After Boc group elimination with TFA, the powder was condensed with (2S,3S)-ethyl hydrogen trans-epoxysuccinate as obtained in Reference Example 8 (622 mg) to yield the title compound (compound 9; 990 mg) as a white powder (yield 57%).

$[\alpha]_D^{26}$ +19° (c 0.56, CHCl$_3$)

Elemental analysis (for C$_{27}$H$_{33}$N$_3$O$_7$·0.2CHCl$_3$): Calculated: C; 61.01, H; 6.25, N; 7.85 Found: C; 60.98, H; 6.26, N; 8.17

$^1$H NMR δ ppm (CDCl$_3$) 1.30 (3H, t, 5=7.2 Hz), 1.34 (4H, m), 2.94–3.21 (6H, m), 3.51 (1H, d, J=1.8 Hz), 3.65 (1H, d, J=1.9 Hz), 4.25 (2H, m), 4.51 (1H, m), 4.81 (1H, br s), 5.10 (2H, s), 5.74 (1H, br s), 6.77 (1H, br d, J=8.4 Hz), 7.18–7.37 (10H, m)

EXAMPLE 12

N-Z-N'-{N-[(2S,3S)-3-trans-carboxyoxirane-2-carbonyl]-D-phenylalanyl}-1,4-diaminobutane Compound 9 (900 mg) was subjected to alkali hydrolysis in the same manner as in Example 6 to yield the title compound (compound 10; 810 mg) as a white powder (yield 95%).

Elemental analysis (for C$_{25}$H$_{29}$N$_3$O$_7$·0.25H$_2$O): Calculated: C; 61.53, H; 6.09, N; 8.61 Found: C; 61.67, H; 5.97, N; 8.75

$^1$H NMR δ ppm (DMSO-d$_6$) 1.34 (4H, m), 2.78 (1H, dd, J=9.3, 13.6 Hz), 2.93–3.10 (5H, m), 3.31 (1H, d, J=1.8 Hz), 3.60 (1H, d, J=1.8 Hz), 4.48 (1H, dt, J=5.4, 8.8 Hz), 5.00 (2H, s), 7.15–7.40 (11H, m), 8.07 (1H, t, J=5.6 Hz), 8.68 (1H, d, J=8.5 Hz)

EXAMPLE 13

N-{N-[(2S,3S)-3-trans-carboxyoxirane-2-carbonyl]-D-phenylalanyl}-1,4-diaminobutane Compound 10 (750 mg) was subjected to catalytic reduction to eliminate the Z group in the same manner as in Example 7, after which it was lyophilized to yield the title compound (compound 11; 510 mg) as a white powder (yield 94%).

$[\alpha]_D^{26}$ +33° (c 0.56, 0.1 N HCl)

Elemental analysis (for C$_{17}$H$_{23}$N$_3$O$_5$·1.5H$_2$O): Calculated: C; 54.25, H; 6.96, N; 11.16 Found: C; 54.44, H; 6.93, N; 11.25

$^1$H NMR δ ppm (D$_2$O) 1.45 (4H, m), 2.87–3.16 (6H, m), 3.34 (1H, d, J=2.1 Hz), 3.52 (1H, d, J=2.0 Hz), 4.49 (1H, t, J=7.9 Hz), 7.24–7.42 (5H, m)

EXAMPLE 14

N-Z-N'-{N-[(2R,3R)-3-trans-methoxycarbonyloxirane-2-carbonyl]-L-phenylalanyl}-1,4-diaminobutane After Boc group elimination with TFA in the same manner as in Example 5, N-(Boc-L-phenylalanyl)-N'-Z-1,4-diaminobutane (1.65 g) was condensed with (2R,3R)-methyl hydrogen trans-epoxysuccinate as obtained in Reference Example 9 (604 mg) to yield the title compound (compound 12; 1.12 g) as a white powder (yield 64%).

$[\alpha]_D^{26}$ −19° (c 0.53, CHCl$_3$)

Elemental analysis (for C$_{26}$H$_{31}$N$_3$O$_7$·0.5H$_2$O): Calculated: C; 61.65, H; 6.37, N; 8.30 Found: C; 61.78, H; 6.03, N; 8.59

$^1$H NMR δ ppm (CDCl$_3$) 1.34 (4H, m), 2.94–3.20 (6H, m), 3.54 (1H, d, J=1.8 Hz), 3.66 (1H, d, J=1.9 Hz), 3.79 (3H, s), 4.54 (1H, m), 4.87 (1H, br t, J=5.5 Hz), 5.09 (2H, s), 5.90 (1H, br s), 6.88 (1H, br d, J=8.0 Hz), 7.17–7.37 (10H, m)

EXAMPLE 15

N-Z-N'-{N-[(2R,3R)-3-trans-carboxyoxirane-2-carbonyl]-L-phenylalanyl}-1,4-diaminobutane The methyl ester of compound 12 (1.00 g) was subjected to alkali hydrolysis in the same manner as in Example 6 to yield the title compound (compound 13; 970 mg) as a white powder (yield quantitative).

Elemental analysis (for C$_{25}$H$_{29}$N$_3$O$_7$·0.7CHCl$_3$): Calculated: C; 54.43, H; 5.28, N; 7.41 Found: C; 54.58, H; 5.62, N; 7.06

$^1$H NMR δ ppm (DMSO-d$_6$) 1.34 (4H, m), 2.82 (1H, dd, J=9.5, 13.5 Hz), 2.91–3.04 (5It, m), 3.05 (1H, m), 3.30 (1H, m), 4.43 (1H, m), 5.00 (2H, s), 7.14–7.40 (11H, m), 8.05 (1H, t, J=5.1 Hz), 8.29 (1H, d, J=8.4 Hz)

EXAMPLE 16

N-{N-[(2R,3R)-3-trans-carboxyoxirane-2-carbonyl]-L-phenylalanyl}-1,4-diaminobutane Compound 13 (860 mg) was subjected to catalytic reduction to eliminate the Z group in the same manner as in Example 7 and then lyophilized to yield the title compound (compound 14; 450 mg) as a white powder (yield 72%).

$[\alpha]_D^{25}$ −35° (c 0.51, 0.1 N HCl)

Elemental analysis (for $C_{17}H_{23}N_3O_5 \cdot 1.5H_2O$): Calculated: C; 54.25, H; 6.96, N; 11.16 Found: C; 54.52, H; 7.05, N; 11.16

$^1$H NMR δ ppm ($D_2O$)

1.47 (4H, m), 2.90–3.16 (6H, m), 3.35 (1H, d, J=2.1 Hz), 3.53 (1H, d, J=1.9 Hz), 4.50 (1H, t, J=7.9 Hz), 7.25–7.43 (5H, m)

EXAMPLE 17

N-Z-N'-{N-[(2S,3S)-3-trans-ethoxycarbonyloxirane-2-carbonyl]-L-tryptophanyl}-1,4-diaminobutane N-Z-1,4-diaminobutane (1.20 g) and Fmoc-L-Trp-OH (2.54 g, produced by Peptide Institute, Inc.) were condensed together in the same manner as in Example 5 to yield N-(Fmoc-L-tryptophanyl)-N'-Z-1,4-diaminobutane (3.75 g) as a white powder (yield quantitative). After a portion (3.50 g) of this powder was dissolved in N,N-dimethylformamide (DMF, 63 ml), piperazine (7.0 ml) was added, followed by stirring at room temperature for 1 hour. After the reaction mixture was concentrated, ethyl acetate (300 ml) was added, followed by two extractions with 0.023 N aqueous hydrochloric acid (300 ml). After adjustment to pit 6.0, the water layer was washed with hexane (100 ml) 6 times, followed by adjustment to pit 8.0 and 3 extractions with ethyl acetate (200 ml). The extract was dried over anhydrous sodium sulfate and concentrated to yield N-(L-tryptophanyl)-N'-Z-1,4-diaminobutane (2.11 g) as a colorless oily substance (yield 93%). After a portion (2.00 g) of this substance was dissolved in DMF (67 ml), (2S,3S)-ethyl hydrogen trans-epoxysuccinate as obtained in Reference Example 8 (862 mg), HOBT (728 mg) and WSC (1.33 g) were added under ice cooling conditions, followed by stirring at room temperature for 14 hours. After the reaction mixture was concentrated, ethyl acetate was added; the mixture was washed with 10% aqueous citric acid, water, saturated aqueous sodium hydrogen carbonate, 2% aqueous sodium hydrogen carbonate, water and saturated saline, and then dried over anhydrous sodium sulfate. The dry product was subjected to silica gel column chromatography (200 ml) for elution with a chloroform eluent supplemented with sequentially added methanol, to yield the title compound (compound 15; 1.83 g) as a white powder (yield 68%) from the fraction eluted with 2% (v;v) methanol.

$[\alpha]_D^{25}$+44° (c 0.56, DMSO)

Elemental analysis (for $C_{29}H_{34}N_4O_7 \cdot 0.25H_2O$): Calculated: C; 62.75, H; 6.32, N; 10.18 Found: C; 62.67, H; 6.22, N; 10.35

$^1$H NMR δ ppm ($CDCl_3$) 1.20 (4H, m), 1.31 (3H, t, J=7.1 Hz), 2.91 (1H, m), 3.07 (3H, m), 3.26 (2H, m), 3.31 (1H, d, J=1.5 Hz), 3.65 (1H, d, J=1.9 Hz), 4.25 (2H, m), 4.65 (1H, m), 4.84 (1H, br s), 5.15 (2H, s), 5.54 (1H, br s), 6.92 (1H, d, J=7.2 Hz), 6.97 (1H, d, J=2.3 Hz), 7.17 (2H, m), 7.30–7.41 (6H, m), 7.70 (1H, d, J=7.5 Hz), 8.60 (1H, br s)

EXAMPLE 18

N-Z-N'-{N-[(2S,3S)-3-trans-carboxyoxirane-2-carbonyl]-L-tryptophanyl}-1,4-diaminobutane The ethyl ester of compound 15 (1.73 g) was subjected to alkali hydrolysis in the same manner as in Example 6 to yield the title compound (compound 16; 1.77 g) as a white powder (yield quantitative).

Elemental analysis (for $C_{27}H_{30}N_4O_7 \cdot 0.8H_2O$): Calculated: C; 60.39, H; 5.93, N; 10.43 Found: C; 60.47, H; 6.08, N; 10.03

$^1$H NMR δ ppm (DMSO-$d_6$) 1.34 (4H, m), 3.00 (5H, m), 3.11 (1H, dd, J=5.5, 14.6 Hz), 3.32 (1H, d, J=1.8 Hz), 3.62 (1H, d, J=1.8 Hz), 4.52 (1H, dt, J=5.5, 8.5 Hz), 5.00 (2H, s), 6.97 (1H, ddd, J=0.9, 6.9, 7.9 Hz), 7.06 (1H, ddd, J=1.1, 6.9, 8.2 Hz), 7.12 (1H, d, J=2.1 Hz), 7.22 (1H, t, J=5.7 Hz), 7.26–7.40 (6H, m), 7.60 (1H, d, J=7.7 Hz), 8.10 (1H, t, J=5.5 Hz), 8.56 (1H, d, J=8.4 Hz), 10.82 (1H, d, J=2.0 Hz)

EXAMPLE 19

N-(N-[(2S,3S)-3-trans-carboxyoxirane-2-carbonyl]-L-tryptophanyl}-1,4-diaminobutane Compound 16 (1.67 g) was subjected to catalytic reduction to eliminate the Z group in the same manner as in Example 7, after which it was lyophilized to yield the title compound (compound 17; 1.06 g) as a white powder (yield 85%).

$[\alpha]_D^{25}$+56° (c 0.64, 0.1 N HCl)

Elemental analysis (for $C_{19}H_{24}N_4O_5 \cdot 1.3H_2O$): Calculated: C; 55.41, H; 6.51, N; 13.60 Found: C; 55.28, H; 6.61, N; 13.72

$^1$H NMR δ ppm ($D_2O$) 1.29 (4H, m), 2.81 (2H, t, J=7.2 Hz), 3.01 (2H, m), 3.23 (2H, m), 3.24 (1H, d, J=1.7 Hz), 3.51 (1H, d, J=1.8 Hz), 4.54 (1H, t, J=7.5 Hz), 7.16 (1H, t, J=7.4 Hz), 7.24 (1H, t, J=7.6 Hz), 7.24 (1H, s), 7.49 (1H, d, J=8.0 Hz), 7.62 (1H, d, J=7.8 Hz)

EXAMPLE 20

N-Z-N'-{N-[(2S,3S)-3-trans-ethoxycarbonyloxirane-2-carbonyl-L-phenylalanyl}ethylenediamine (2S,3S)-ethyl hydrogen trans-epoxysuccinate as obtained in Reference Example 8 (5.00 g) was dissolved in dichloromethane (300 ml) and cooled with ice. To this solution, H-Phe-OBzl·Tos (12.0 g, produced by Peptide Institute, Inc.), HOBT (4.22 g), WSC (5.99 g) and triethylamine= (3.74 ml) were added, followed by stirring at room temperature for 14 hours. After concentration, the reaction mixture was dissolved in ethyl acetate, and washed with 10% aqueous citric acid, water, saturated aqueous sodium hydrogen carbonate, 2% aqueous sodium hydrogen carbonate, water and saturated saline, and then dried over anhydrous sodium sulfate. After concentration, the dry product was subjected to silica gel column chromatography for elution with a hexane eluent supplemented with sequentially added ethyl acetate to yield N-(2S,3S)-3-trans-ethoxycarbonyloxirane-2-carbonyl]-L-phenylalanine benzyl ester (8.56 g) as a white powder (yield 77%) from the fraction eluted with 30% ethyl acetate.

$[\alpha]_D^{26}$+55° (c 0.51, $CHCl_3$)

Elemental analysis (for $C_{22}H_{23}NO_6$): Calculated: C: 66.49, H; 5.83, N; 3.52 Found: C: 66.38, H; 5.82, N; 3.33 H $^1$H NMR δ ppm ($CDCl_3$) 1.29 (3H, t, J=7.1 Hz), 3.03 (1H, dd, J=6.6, 13.9 Hz), 3.16 (1H, d, J=1.9 Hz), 3.20 (1H, dd, J=5.9, 13.9 Hz), 3.62 (1H, d, J=1.9 Hz), 4.23 (2H, m), 4.87 (1H, ddd, J=6.2, 6.3, 8.0 Hz), 5.18 (2H, dd, J=12.1, 20.1 Hz), 6.54 (1H, d, J=8.0 Hz), 6.97 (2H, m), 7.21–7.41 (8H, m)

A portion (1.50 g) of this substance was dissolved in methanol (50 ml). To this solution, palladium/activated carbon [10% (w/w), 150 mg] was added, followed by stirring at room temperature for 1.5 hours in hydrogen atmosphere. After the catalyst was filtered off, the filtrate was concentrated to yield N-[(2S,3S)-3-trans-ethoxycarbonyloxirane-2-carbonyl]-L-phenylalanine (1.11 g) as a white powder (yield 96%).

A portion (870 mg) of this powder was dissolved in DMF (30 ml), N-Z-ethylenediamine (549 mg) as described in Hoppe-Seylers' Zeitschrift Physiolgische Chemie, Vol. 39, p. 251 (1968), HOBT (382 mg) and WSC (543 mg) were added under ice cooling conditions, followed by stirring at room temperature for 16 hours. After the reaction mixture was concentrated, ethyl acetate (200 ml) was added; the mixture was washed with 10% aqueous citric acid, water, saturated aqueous sodium hydrogen carbonate, 2% aqueous sodium hydrogen carbonate, water and saturated saline, and then dried over anhydrous sodium sulfate. The dry product was subjected to silica gel column chromatography for elution with a chloroform eluent supplemented with sequentially added methanol, to yield the title compound (compound 18; 980 mg) as a white powder (yield 72%) from the fraction eluted with 2–3% (v/v) methanol.

$[\alpha]_D^{26}$ +24° (c 0.55, CHCl$_3$)

Elemental analysis (for C$_{25}$H$_{29}$N$_3$O$_7$·0.25H$_2$O) Calculated: C; 61.53, H; 6.09, N; 8.61 Found: C; 61.76, H; 5.99, N; 8.71

$^1$H NMR δ ppm (CDCl$_3$) 1.30 (3H, t, J=7.2 Hz), 2.97 (1H, dd, J=7.5, 13.7 Hz), 3.08 (1H, dd, J=7.3, 13.7 Hz), 3.13 (1H, d, J=1.8 Hz), 3.15–3.40 (4H, m), 3.63 (1H, d, J=1.8 Hz), 4.23 (2H, m), 4.57 (1H, dt, J=7.9, 7.5 Hz), 5.08 (2H, s), 6.48 (1H, br s), 6.69 (1H, br d, J=8.1 Hz), 7.15 (2H, m), 7.22–7.39 (8H, m)

EXAMPLE 21

N-Z-N'-{[(2S,3S)-3-trans-carboxyoxirane-2-carbonyl]-L-phenylalanyl)ethylenediamine The ethyl ester of compound 18 (900 mg) was subjected to alkali hydrolysis in the same manner as in Example 6 to yield the title compound (compound 19; 860 mg) as a white powder (yield 96%).

Elemental analysis (for C$_{23}$H$_{25}$N$_3$O$_7$): Calculated: C: 60.65, H; 5.53, N; 9.23 Found: C; 60.70, H; 5.53, N; 9.30

$^1$H NMR δ ppm (DMSO-d$_6$) 2.79 (1H, dd, J=9.8, 13.7 Hz), 2.98–3.22 (5H,m), 3.27 (1H, d, J=1.8 Hz), 3.57 (1H, d, J=1.8 Hz), 4.49 (1H, dr, J=5.0, 9.1 Hz), 5.01 (2H, s), 7.16–7.40 (10H, m), 8.19 (1H, t, J=5.5 Hz), 8.59 (1H, d, J=8.6 Hz)

EXAMPLE 22

N-{N-[(2S,3S)-3-trans-carboxyoxirane-2-carbonyl]-L-phenylalanyl}-ethylenediamine Compound 19 (780 mg) was subjected to catalytic reduction to eliminate the Z group in the same manner as in Example 7, and then lyophilized to yield the title compound (compound 20; 480 mg) as a white powder (yield 87%).

$[\alpha]_D^{27}$ +50° (C 0.57, 0.1 N HCl)

Elemental analysis (for C$_{15}$H$_{19}$N$_3$O$_5$·1H$_2$O): Calculated: C: 53.09, H; 6.24, N; 12.38 Found: C; 52.89, H; 6.48, N; 12.47

$^1$H NMR δ ppm (D$_2$O) 3.02 (3H, m), 3.16 (1H, d, J=1.9 Hz), 3.18 (1H, m), 3.41 (2H, m), 3.49 (1H, d, J=1.9 Hz), 4.60 (1H, dd, J=6.9, 8.7 Hz), 7.23–7.43 (5H, m)

EXAMPLE 23

N-Z-N'-{N-[(2S,3S)-3-trans-ethoxycarbonyloxirane-2-carbonyl]-L-phenylalanyl}-1,8-diaminooctane N-[(2S,3S)-3-trans-ethoxycarbonyloxirane-2-carbonyl]-L-phenylalanine (1.11 g) and N-Z-1,8-diaminooctane (1.09 g) as produced from 1,8-diaminooctane in accordance with the method described in Hoppe-Seylers' Zeitschrift Physiolgische Chemie, Vol. 349, p. 251 (1968) were condensed together in the same manner as in Example 20 to yield the title compound (compound 21; 1.54 g) as a white powder (yield 76%).

$[\alpha]_D^{26}$ +18° (C 0.59, CHCl$_3$)

Elemental analysis (for C$_{31}$H$_{41}$N$_3$O$_7$·0.25H$_2$O): Calculated: C; 65.07, H; 7.31, N; 7.34 Found: C; 65.27, H; 7.28, N; 7.35

$^1$H NMR δ ppm (CDCl$_3$) 1.15–1.41 (12H, m), 1.30 (3H, t, J=7.2 Hz), 1.49 (2H, m), 3.03 (2H, m), 3.13 (1H, d, J=1.9 Hz), 3.17 (4H, m), 3.62 (1H, d, J=1.9 Hz), 4.24 (2H, m), 4.53 (1H, dt, J=7.8, 7.6 Hz), 4.79 (1H, br s), 5.09 (2H, s), 5.65 (1H, br s), 6.73 (1H, br d, J=7.9 Hz), 7.17 (2H, m), 7.23–7.38 (8H, m)

EXAMPLE 24

N-Z-N'-{N-[(2S,3S)-3-trans-carboxyoxirane-2-carbonyl]-L-phenylalanyl}-1,8-diaminooctane The ethyl ester of compound 21 (1.44 g) was subjected to alkali hydrolysis in the same manner as in Example 6 to yield the title compound (compound 22; 1.41 g) as a white powder (yield quantitative).

Elemental analysis (for C$_{29}$H$_{37}$N$_3$O$_7$·0.25H$_2$O): Calculated: C; 64.01, H; 6.95, N; 7.72 Found: C; 63.96, H; 6.98, N; 7.70

$^1$H NMR δ ppm (DMSO-d$_6$) 1.22 (8H, m), 1.36 (4H, m), 2.80 (1H, dd, J=9.2, 13.5 Hz), 3.00 (5H, m), 3.29 (1H, d, J=1.8 Hz), 3.58 (1H, d, J=1.8 Hz), 4.50 (1H, dr, J=5.4, 8.9 Hz), 5.00 (2H, s), 7.16–7.40 (10H, m), 8.07 (1H, t, J=5.6 Hz), 8.61 (1H, d, J=8.6 Hz)

EXAMPLE 25

N-(N-[(2S,3S)-3-trans-carboxyoxirane-2-carbonyl]-L-phenylalanyl}-1,8-diaminooctane Compound 22 (1.30 g) was subjected to catalytic reduction to eliminate the Z group in the same manner as in Example 7, and then lyophilized to yield the title compound (compound 23; 872 mg) as a white powder (yield 90%).

$[\alpha]_D^{27}$ +46° (c 0.53, 0.1 N HCl)

Elemental analysis (for C$_{21}$H$_{31}$N$_3$O$_5$·0.25H$_2$O): Calculated: C; 61.52, H; 7.74, N; 10.25 Found: C; 61.75, H; 7.60, N; 10.08

$^1$H NMR δ ppm (D$_2$O) 1.33 (10H, m), 1.64 (2H, m), 2.98 (2H, m), 3.10 (4H, m), 3.22 (1H, d, J=1.9 Hz), 3.50 (1H, d, J=2.1 Hz), 4.53 (1H, t, J=7.8 Hz), 7.24–7.42 (5H, m)

EXAMPLE 26

N-methyl-N'-{N-[(2S,3S)-3-trans-ethoxycarbonyloxirane-2-carbonyl]-L-phenylalanyl}piperazine N-[(2S,3S)-3-trans-ethoxycarbonyloxirane-2-carbonyl]-L-phenylalanine (1.50 g) and N-methylpiperazine (651 μl) were condensed together in the same manner as in Example 20 to yield the title compound (compound 24; 1.59 g) as a colorless oily substance (yield 84%).

$[\alpha]_D^{26}$ +30° (c0.59, CHCl$_3$)

Elemental analysis (for C$_{20}$H$_{27}$N$_3$O$_5$·0.22CHCl$_3$): Calculated: C: 58.42, H; 6.60, N; 10.11 Found: C; 58.31, H; 6.60, N; 10.35

$^1$H NMR δ ppm (CDCl$_3$) 1.31 (3It, t, J=7.2 Hz), 1.90 (1H, m), 2.21 (3H, s), 2.23 (1It, m), 2.30 (2H, m), 2.97 (2H, m), 3.04 (1H, m), 3.32 (1H, d, J=1.9 Hz), 3.36 (1H, m), 3.51 (1H, m), 3.62 (1H, d, J=1.9 Hz), 3.66 (1H, m), 4.25 (2H, m), 5.13 (1H, ddd, J=6.4, 8.2, 8.2 Hz), 6.99 (1H, br d, J=8.2 Hz), 7.15 (2H, m), 7.22–7.34 (3H, m)

EXAMPLE 27

N-methyl-N'-{N-[(2S,3S)-3-trans-carboxyoxirane-2-carbonyl]-L-phenylalanyl}piperazine The ethyl ester of compound 24 (1.50 g) was subjected to alkali hydrolysis in the same manner as in Example 6 and concentrated. After water addition and adjustment to pH 6.5, the mixture was applied to a column with Diaion HP-20 (30 ml, produced by Mitsubishi Chemical Industries), washed with water, and then eluted with 50% (v/v) aqueous methanol. The eluate was concentrated and lyophilized to yield the title compound (compound 25; 1.17 g) as a white powder (yield 84%).

$[\alpha]_D^{27}$ +78° (c 0.58, 0.1 N HCl)

Elemental analysis (for C$_{18}$H$_{23}$N$_3$O$_5$·1.5H$_2$O): Calculated: C; 55.66, H; 6.75, N; 10.82 Found: C; 55.52, H; 6.89, N; 10.76

$^1$H NMR δ ppm (D$_2$O) 2.12 (1H, m), 2.64 (3H, s), 2.78 (1H, m), 3.07 (4H, m), 3.36 (1H, d, J=1.8 Hz), 3.49 (1H, m), 3.53 (1H, d, J=1.8 Hz), 3.60 (2H, m), 3.85 (1H, m), 5.07 (1H, dd, J=6.7, 9.2 Hz), 7.27–7.47 (5H, m)

EXAMPLE 28

N-{N-[(2S,3S)-3-trans-ethoxycarbonyloxirane-2-carbonyl]-L-phenylalanyl}-morpholine N-[(2S,3S)-3-trans-ethoxycarbonyloxirane-2-carbonyl]-L-phenylalanine (1.00 g) and morpholine (313 µl) were condensed together in the same manner as in Example 20 to yield the title compound (compound 26; 1.09 g) as a colorless oily substance (yield 89%).

$[\alpha]_D^{25}$ +41° (c 0.64, CHCl$_3$)

Elemental analysis (for C$_{19}$H$_{24}$N$_2$O$_6$·0.35CHCl$_3$): Calculated: C; 55.57, H; 5.87, N; 6.70 Found: C; 55.48, H; 5.85, N; 6.73

$^1$H NMR δ ppm (CDCl$_3$) 1.31 (3H, t, J=7.2 Hz), 2.99 (4H, m), 3.31 (1H, m), 3.35 (1H, d, J=1.9 Hz), 3.40–3.62 (5H, m), 3.63 (1H, d, J=1.9 Hz), 4.26 (2H, m), 5.10 (1H, q, J=7.6 Hz), 6.95 (1H, d, J=8.2 Hz), 7.17 (2H, m), 7.30 (3H, m)

EXAMPLE 29

N-{N-[(2S,3S)-3-trans-carboxyoxirane-2-carbonyl]-L-phenylalanyl}morpholine monosodium salt The ethyl ester of compound 26 (990 mg) was subjected to alkali hydrolysis in the same manner as in Example 27, desalinized with resin, concentrated and lyophilized to yield the title compound (compound 27; 700 mg) (yield 72%).

$[\alpha]_D^{25}$ +70° (c 0.63, H$_2$O)

Elemental analysis (for C$_{17}$H$_{19}$N$_2$O$_6$Na·0.7H$_2$O): Calculated: C; 53.31, H; 5.37, N; 7.32, Na; 6.00 Found: C: 53.52, H; 5.72, N; 7.32, Na; 6.00

$^1$H NMR δ ppm (D$_2$O) 2.98 (1H, m), 3.06 (2H, m), 3.26 (1H, m), 3.35 (1H, d, J=2.0 Hz), 3.46 (3H, m), 3.53 (1H, d, J=2.0 Hz), 3.56 (2H, m), 3.66 (1H, m), 5.07 (1H, dd, J=7.0, 8.6 Hz), 7.28 (2H, m), 7.38 (3H, m)

EXAMPLE 30

N-acetyl-N'-{N-[(2S,3S)-3-trans-ethoxycarbonyloxirane-2-carbonyl]-L-phenylalanyl}-1,4-diaminobutane After N-acetyl-N'-Z-1,4-diaminobutane as obtained in Reference Example 10 (0.94 g) was dissolved in methanol (32 ml), palladium/activated carbon [10% (w/w/), 94 mg] was added, followed by stirring at 25° C. for 1.5 hours in hydrogen atmosphere. After the catalyst was filtered off, the filtrate was concentrated to dryness to yield N-acetyl-1,4-diaminobutane (0.47 g).

N-[(2S,3S)-3-trans-ethoxycarbonyloxirane-2-carbonyl]-L-phenylalanine (1.22 g) and N-acetyl-1,4-diaminobutane (0.47 g) were condensed together in the same manner as in Example 20 to yield the title compound (compound 28; 0.96 g) as a white powder (yield 63%).

Elemental analysis (for C$_{21}$H$_{29}$N$_3$O$_6$·0.3H$_2$O): Calculated: C; 59.37, H; 7.02, N; 9.89 Found: C; 59.37, H; 6.89, N; 9.79

$^1$H NMR δ ppm (DMSO-d$_6$) 1.22 (3H, t, J=7.0 Hz), 1.32 (4H, m), 1.78 (3H, s), 2.79 (1H, dd, J=9.5, 14.0 Hz), 2.92–3.10 (5H, m), 3.42 (1H, d, J=2.0 Hz), 3.64 (1H, d, J=2.0 Hz), 4.17 (2H, m), 4.50 (1H, m), 7.16–7.31 (5H, m), 7.79 (1H, br t, J=5.5 Hz), 8.11 (1H, br t, J=5.5 Hz), 8.66 (1H, br d, J=8.5 Hz)

EXAMPLE 31

N-acetyl-N'-{N-[(2S,3S)-3-trans-carboxyoxirane-2-carbonyl]-L-phenylalanyl}-1,4-diaminobutane monosodium salt The ethyl ester of compound 28 (950 mg) was subjected to alkali hydrolysis in the same manner as in Example 27, desalinized with resin, concentrated and lyophilized to yield the title compound (compound 29; 858 mg) (yield 92%).

$[\alpha]_D^{24}$ +39° (c 0.52, H$_2$O)

Elemental analysis (for C$_{19}$H$_{24}$N$_3$O$_6$Na·H$_2$O): Calculated: C; 52.90, H; 6.07, N; 9.74, Na; 5.33 Found: C; 53.02, H; 6.36, N; 9.84, Na; 5.40

$^1$H NMR δ ppm (DMSO-d$_6$) 1.34 (4H, m), 1.78 (3H, s), 2.83 (1H, dd, J=10.5, 13.5 Hz), 2.90 (1H, d, J=2.0 Hz), 2.92–3.12 (5H, m), 3.24 (1H, d, J=2.0 Hz), 4.34 (1H, m), 7.16–7.32 (5H, m), 8.08 (1H, br t, J=5.5 Hz), 8.70 (1H, br t, J=5.0 Hz), 9.45 (1H, br d, J=8.0 Hz)

EXAMPLE 32

TAN-1854A monohydrochloride

N-Z-N'-(Z-3-aminopropyl)-1,4-diaminobutane as produced from 3-amino-1-propanol and 1,4-diaminobutane in accordance with the method described in Japanese Patent Unexamined Publication No. 192347/1982 (116 mg) and Boc-L-Phe-OH (118 mg, produced by Peptide Institute, Inc.) were condensed together in the same manner as in Example 5 to yield N-(Boc-L-phenylalanyl)-N-(Z-3-aminopropyl)-N'-Z-1,4-diaminobutane (162 mg) as a white powder (yield 61%). After Boc group of this compound (157 mg) was deprotected with TFA, the resulting powder was condensed with (2S,3S)-ethyl hydrogen trans-epoxysuccinate as obtained in Reference Example 8 (35 mg) to yield N-Z-N'-{N-[(2S,3S)-3-trans-ethoxycarbonyloxirane-2-carbonyl]-L-phenylalanyl]-N'-(Z-3-aminopropyl)-1,4-diaminobutane (88 mg) as a white powder (yield 53%).

This compound (87 mg) was subjected to alkali hydrolysis in the same manner as in Example 6 to yield N-Z-N'-{N-[(2S,3S)-3-trans-carboxyoxirane-2-carbonyl]-L-phenylalanyl]-N'-(Z-3-aminopropyl)-1,4-diaminobutane (82 mg) (yield 98%).

After this compound (81 mg) was dissolved in methanol (7 ml), water (3.5 ml), acetic acid (8 μl) and palladium/activated carbon [10% (w/w), 23 mg] were added, followed by stirring at room temperature for 1.5 hours in hydrogen atmosphere. After the catalyst was filtered off, the filtrate was concentrated and subjected to column chromatography with CM-Sephadex C-25 (sodium type, 10 ml) for elution with 0.05 M saline. The fraction dominated by TAN-1854A was collected, concentrated, and then subjected to preparative HPLC [column YMC-Pack, D-ODS-5 (S-5 120A); mobile phase 3% (v/v) acetonitrile/0.01 M phosphate buffer (pH 6.3); flow rate 10 ml/min]. The fraction showing a single peak of TAN-1854A in analytical HPLC was collected, passed through a column packed with Amberlite IRA-402 (chlorine type, 20 ml) and washed with water (20 ml). The effluent was combined with washings, and the mixture was concentrated and desalinized with Diaion HP-20 (100–200 mesh, 15 ml). The eluate was concentrated and then lyophilized to yield TAN-1854A monohydrochloride (compound 3; 31 mg) (yield 58%).

The physico-chemical data on this compound agreed with those on the compound obtained from the culture broth.

EXAMPLE 33

Preparation of main culture broth of TAN-1756 A, B, C, D

*Chaetomium globosum* FL-41927 strain grown on potato-dextrose agar slant medium was inoculated to 500 ml of a seed medium (pH 7.0) containing 2% glucose, 3% soluble starch, 1% soybean flour, 0.3% corn steep liquor, 0.5% peptone, 0.3% sodium chloride and 0.5% calcium carbonate in a 2L Sakaguchi flask, and cultured at 28° C. for 48 hours on a reciprocal shaker.

500 ml of this culture broth was transferred to 120 liters of a seed medium (pH 7.0) in a 200 liter stainless steel tank. The fermentation was carried out at 24° C. for 48 hours with aeration of 120 liters/min, agitation of 120 rpm and an inner pressure of 1 kg/cm². And 12 liter of this culture broth was transferred to 1200 liters of a main medium containing 5% soluble starch, 1.5% corn gluten meal, 0.3% beer yeast, 1% magnesium sulfate, 0.7% potassium dihydrogen phosphate, 2% disodium hydrogen phosphate and 0.7% calcium carbonate (pH not modified) in a 2000 liter stainless steel tank. The fermentation was carried out at 28° C. with aeration of 1200 liters/min, agitation of 120 rpm and an inner pressure of 1 kg/cm², for 5 days to yield the main culture broth.

EXAMPLE 34

TAN-1756C ½ sulfate, TAN-1756D ½ sulfate

The culture broth (1100 L) obtained in Example 33 was filtered using a filter aid (Radiolite 600). After adjustment to pH 6.8, the filtrate (1420 L) was subjected to column chromatography with Diaion HP-20 (150 L), washed with water (450 L) and then eluted with 70% (v/v) aqueous methanol (750 L). The eluate was concentrated under reduced pressure, passed through a column packed with Amberlite IRA-402 (Cl type, 25 L), and washed with water (50 L). The effluent was combined with washings, which was adjusted to pH 7 and subjected to a column chromatography with Diaion HP-20 (60L). The column was washed with water (180L), then eluted with 70% (v/v) aqueous methanol (120L), and the eluate was concentrated under reduced pressure. In washings, TAN-1756B (2.6g) was detected by HPLC analysis. The concentrate was again subjected to a column chromatography with Diaion HP-20 (100–200 mesh, 2L). The column was subjected to fractional elution with water (6L) and 20% (v/v) aqueous methanol (6 L), successively. In the effluent and washings (0–2L), TAN-1756A (4.3 g) was detected by HPLC analysis. The fractions eluted with water (2–6L) and with 20% (v/v) (0–2L) were combined and concentrated. The concentrate was combined with the concentrate obtained from the culture broth (1200L) by substantially the same procedure to obtain 400 ml of the concentrate.

The concentrate (400 ml) thus obtained was subjected to a column chromatography with Amberlite IRC-50 (Na type, 1L). The column was subjected to fractional elution with water (4L) and 1M saline (6L), successively. The fraction eluted with water (1.5–4L) and that eluted with 1M saline were combined, which was subjected to a column chromatography with Diaion HP-20 (500 ml). The column was washed with water (2L) and 50% (v/v) aqueous methanol (1.5L), and then eluted with 50% (v/v) methanol/0.005M HCl (1L). The eluate was concentrated, which was lyophilized to give a crude powder (987 mg) containing TAN-1756C and D.

This crude powder (980 mg) was dissolved in water (100 ml). The solution was allowed to pass through a column packed with CM-sephadex C-25 (Na type, 80 ml), and washed with water (240 ml), followed by fractional elution with a 0.05M saline. The resulting fractions were divided into two combined fractions: a fraction dominated by TAN-1756C (1000–1240 ml) and a fraction dominated by TAN-1756D (740–1000 ml). Each fraction was desalinized with Diaion HP-20. The eluate was concentrated, lyophilized to yield a powder (330 mg) containing TAN-1756C and another powder (150 mg) containing TAN-1756D.

The powder containing TAN-1756C (320 mg) was subjected to preparative HPLC [column, YMC-Pack, S-363-15, ODS; mobile phase, 4% (v/v) acetonitrile/0.01M phosphate buffer solution (pH 3.0); flow rate, 20 ml/min.). The fractions giving a single peak of TAN-1756C in analytical HPLC, were collected, which was allowed to pass through a column packed with Amberlite IRA-402 (Cl type, 100 ml), and washed with water (100 ml). The effluent was combined with washings, and the mixture was concentrated and desalinized with Diaion HP-20 (30 ml). The eluate was concentrated and then lyophilized to yield TAN-1756C monohydrochloride (181 mg). TAN-1756C monohydrochloride (178 mg) was dissolved in water (20 ml), which was allowed to pass through a column packed with Amberlite IRA-402 (SO₄ type, 10 ml), then the column was washed with water (20 ml). The effluent and washings were combined, which was concentrated and then lyophilized to yield TAN-1756C ½ sulfate (Compound 30; 173 mg).

The powder containing TAN-1756D (145 mg) was subjected to preparative HPLC [column, YMC-Pack, D-ODS-5; mobile phase, 3% (v/v) acetonitrile/0.01M phosphate buffer (pH 3.0); flow rate, 10 ml/min.]. The fraction showing a single peak in analytical HPLC was collected, which was allowed to pass through a column packed with Amberlite IRA-402 ($SO_4$ type, 50 ml), then the column was washed with water (90 ml). The effluent and washings were combined, which was concentrated and then desalinized with Diaion HP-20 (15 ml). The eluate was concentrated and then lyophilized to yield TAN-1756D ½ sulfate (compound 31; 78 mg).

TAN-1756C ½ sulfate

Figure 9:
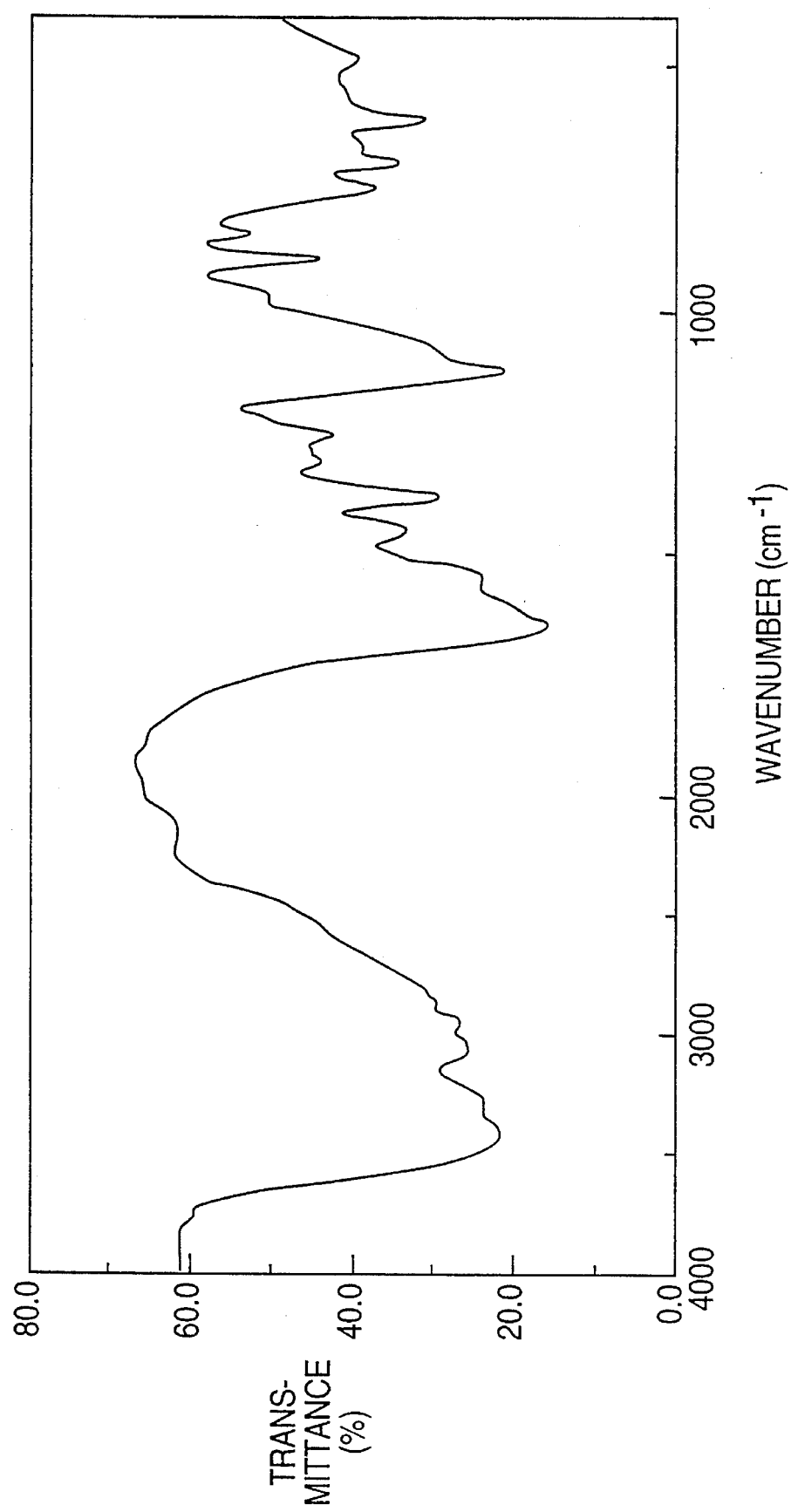
FIG. 9 is the IR spectrum of TAN-1756C ½ sulfate.
Figure 10:
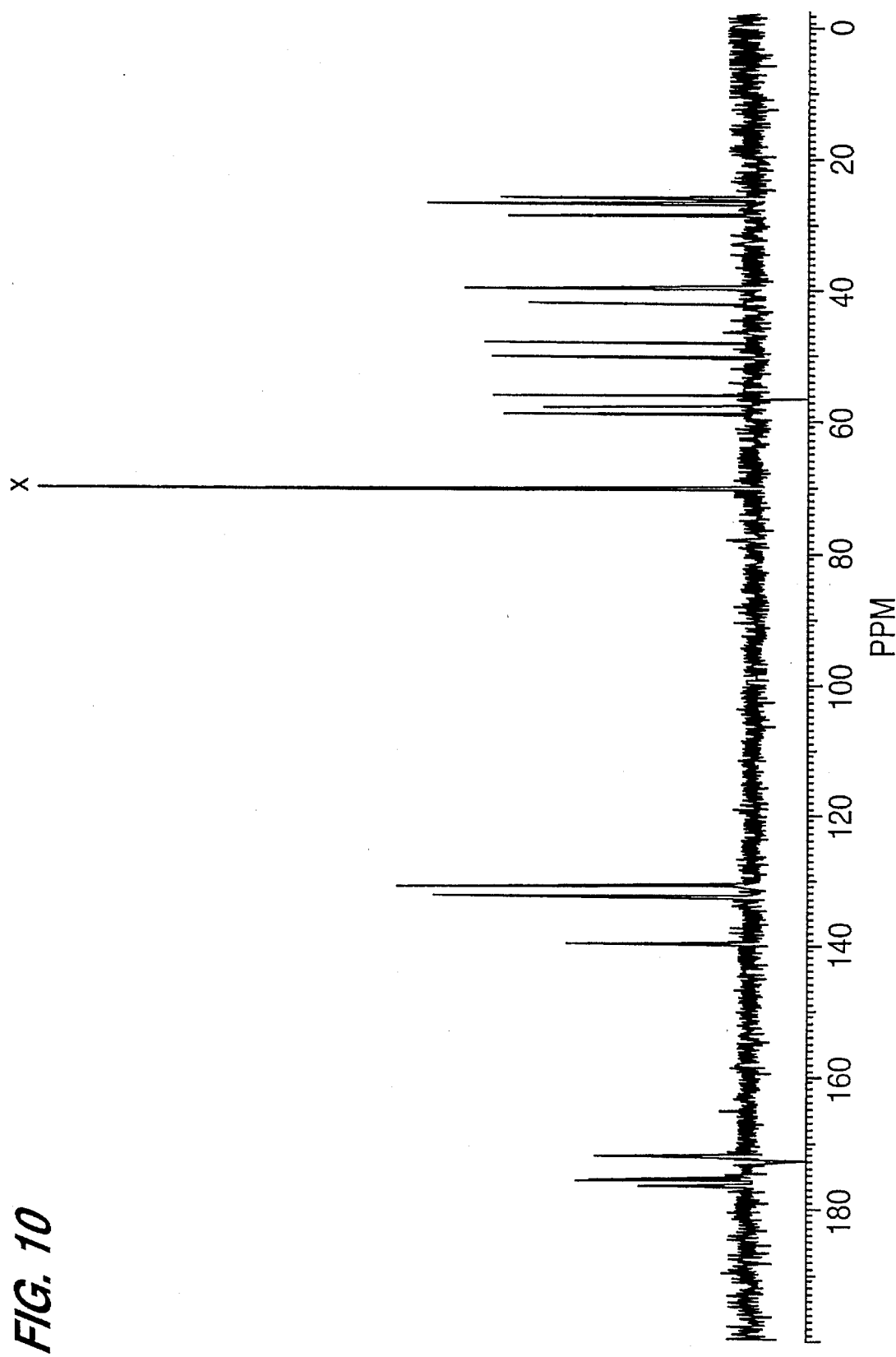

1) Appearance: white powder
2) Optical rotation: +39° (c 0.51, 0.1N HCl, 24° C.)
3) Molecular weight: m/z 407 (M+H)$^+$, (SI-mass spectrum)
4) Elemental analysis: (%, i mol water assumede) Found: C, 50.27; H, 7.00; N, 12.05; S, 2.95 Calcd.: C, 50.73; H, 7.02; N, 11.83; S, 3.39
5) Molecular formula: $C_{20}H_{30}N_4O_5 \cdot ½H_2SO_4$
6) UV spectrum: in water
   Maximum value: 257 nm (δ250, shoulder)
7) IR spectrum: in KBr tablet, major absorptions shown (wave number, cm$^{-1}$). (FIG. 9) 3430, 3280, 3060, 2950, 1650, 1550, 1450, 1380, 1250, 1120, 900, 750, 620
8) $^{13}$C NMR spectrum: 75Mz, in heavy water, δ ppm (FIG. 10) 176.5 (Q), 175.5 (Q), 172.4 (Q), 139.2(Q), 132.1×2 (CH), 131.7×2 (CH), 130.2 (CH), 58.3 (CH), 57.2 (CH), 55.7 (CH), 50.2 ($CH_2$), 47.3 ($CH_2$), 41.3 ($CH_2$), 39.7 ($CH_2$), 39.5 ($CH_2$), 28.3 ($CH_2$), 26.7 ($CH_2$), 25.7 ($CH_2$),
9) Coloring reactions:
   Positive: ninhydrin reaction, peptide reaction, phosphomolybdic acid reaction
   Negative: Sakaguchi reaction, Ehrlich reaction
10) High performance liquid chromatography (HPLC):
    Column: YMC-Pack A-312, ODS
    Mobile phase: 7% (v/v) acetonitrile/0.01 M phosphate buffer (pH 6.3)
    Flow rate: 2.0 ml/min
    Detection: 214 nm
    Retention time: 7.2 minutes
11) Thin-layer chromatography (TLC):
    Carrier; Silica gel 60F$_{254}$
    Developing solvent: n-butanol:aetic acid:water (2:1:1)
    Rf value: 0.14

TAN-1756D ½ sulfate

Figure 11:
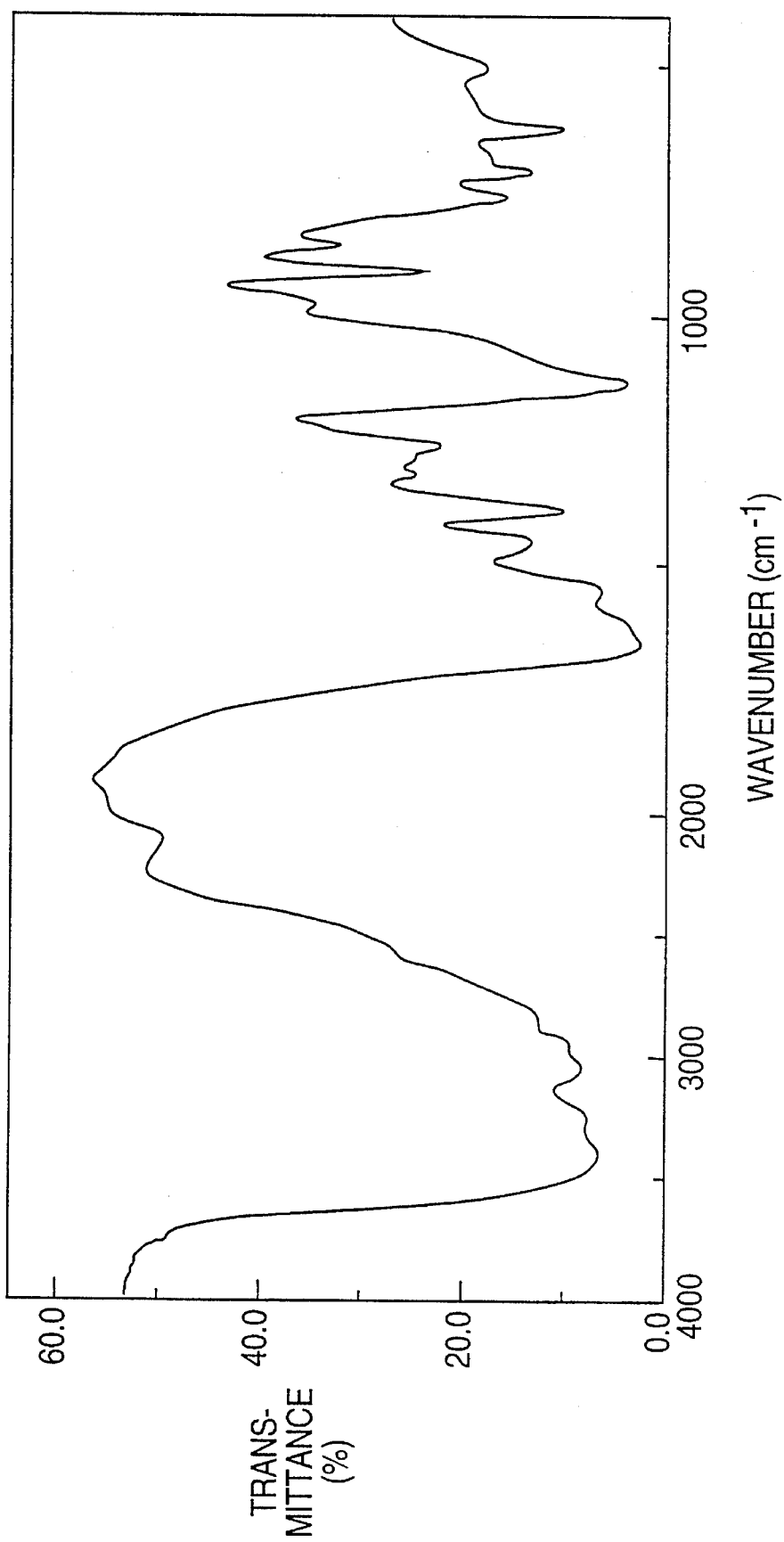
Figure 12:
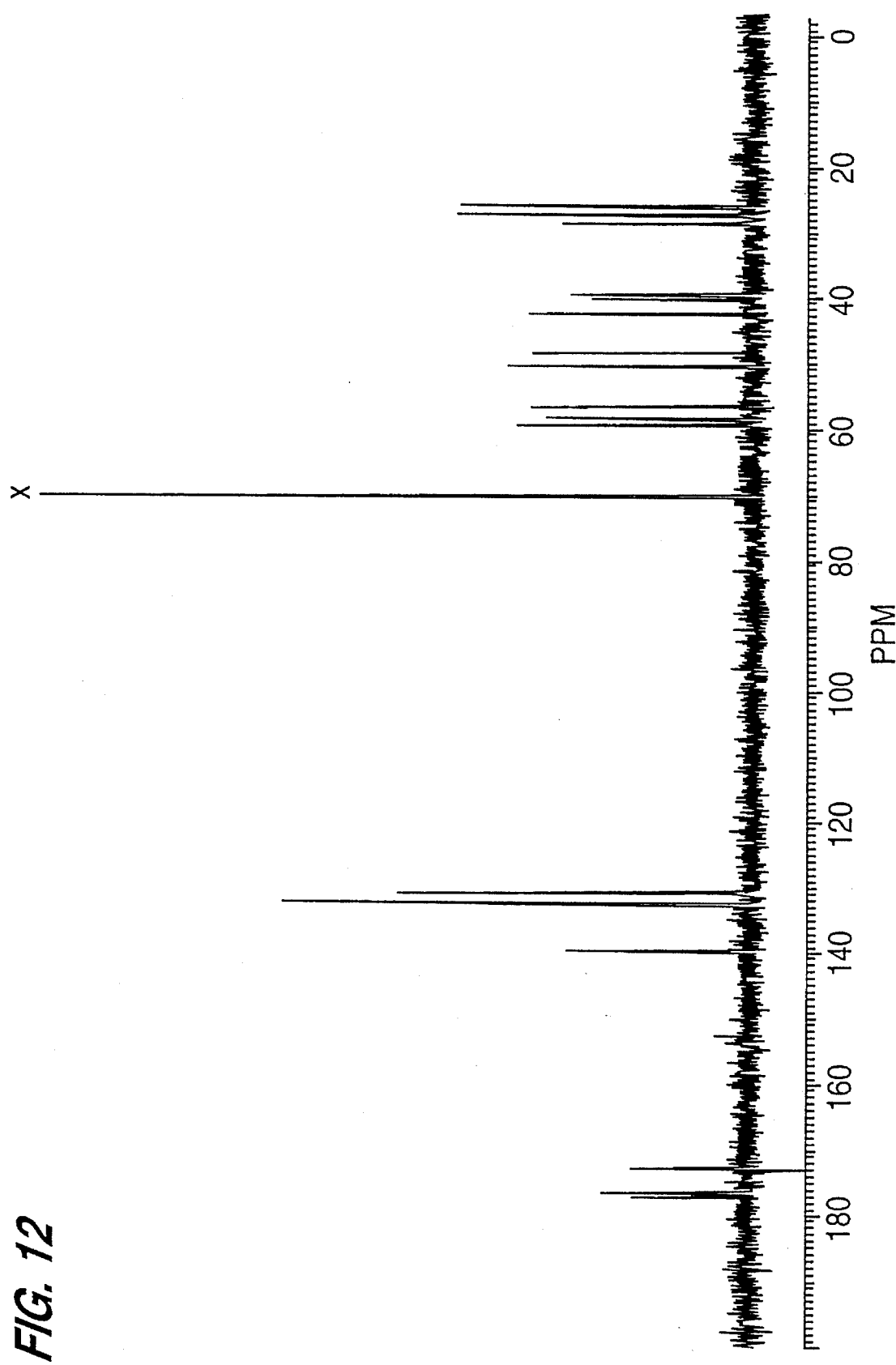

1) Appearance: white powder
2) Optical rotation: +46° (c 0.58, 0.1N HCl, 24° C.)
3) Molecular weight: m/z 407 (M+H)$^+$, (SI-mass spectrum)
4) Elemental analysis: (%, 1.5 mol water assumed) Found: C, 50.08; H, 7.07; N, 12.02 Calcd.: C, 49.78; H, 7.10; N, 11.61
5) Molecular formula: $C_{20}H_{30}N_4O_5 \cdot ½H_2SO_4$
6) UV spectrum: in water
   Maximum value: 257 nm (ε200, shoulder)
7) IR spectrum: in KBr tablet, major absorptions shown (wave number, cm$^{-1}$). (FIG. 11) 3430, 3270, 3060, 2950, 1650, 1550, 1450, 1380, 1250, 1120, 900, 750, 700, 620
8) $^{13}$C NMR spectrum: 75 Mz, in heavy water, δ ppm (FIG. 12) 176.5 (Q), 176.0 (Q), 172.5 (Q), 139. l(Q), 132.1×2 (CH), 131.3×2 (CH), 130.2 (CH), 58.3 (CH), 57.2 (CH), 55.6 (CH), 49.8 ($CH_2$), 47.8 ($CH_2$), 41.7 ($CH_2$), 39.6 ($CH_2$), 38.9 ($CH_2$), 26.8 ($CH_2$), 25.6 ($CH_2$)
9) Coloring reaction:
   Positive: ninhydrin reaction, peptide reaction, phosphomolybdic acid reaction
   Negative: Sakaguchi reaction, Ehrlich reaction
10) High performance liquid chromatography (HPLC):
    Column: YMC-Pack A-312, ODS
    Mobile phase: 7% (v/v)
    Flow rate: 2.0 ml/min
    Detection: 214 nm
    Retention time: 5.5 minutes
11) Thin-layer chromatography (TLC):
    Carrier; Silica gel 60F$_{254}$
    Developing solvent: n-butanol:aetic acid:water (2:1:1)
    Rf value: 0.14

EXAMPLE 35

N-tosyl-N'-{N-[(2S,3S)-3-trans-ethoxycarbonyloxirane-2-carbonyl]-L-phenylalanyl}-1,4-diaminobutane N-Z-1,4-diaminobutane (1.40 g) was dissolved in pyridine (20 ml), to which was added tosyl chloride (1.38 g) under ice-cooling conditions. The mixture was stirred for 7 hours at room temperature. The reaction mixture was concentrated to dryness under reduced pressure, to which was added ethyl acetate, followed by washing with 0.2N HCl, a 2% aqueous solution of sodium hydrogen carbonate and a saturated aqueous saline solution, successively. The organic layer was dried over anhydrous sodium sulfate, which was then subjected to a silica-gel column chromatography (100 ml) for elution with hexane eluent supplemented with sequentially added ethyl acetate, to yield N-tosyl-N'-Z-1,4-diaminobutane (1.97 g) from the fraction eluted with 50% (v/v) ethyl acetate (yield 83%).

N-tosyl-N'-Z-1,4-diaminobutane (1.90 g) thus obtained was dissolved in methanol (60 ml), to which was added palladium/activated carbon [10% (w/w), 190 mg]. The mixture was stirred for 1.5 hour at 25° C. in hydrogen atmosphere. The catalyst was filtered off, and the filtrate was concentrated to dryness to yield N-tosyl-1,4-diaminobutane (1.27 g). (The yield was quantitative.)

In substantially the same manner as in Example 5, N-tosyl-1,4-diaminobutane (1.27 g) was condensed with Boc-L-Phe-OH (1.47 g) to give N-(Boc-L-phenylalanyl)-N'-tosyl-1,4-diaminobutane (2.19 g) (yield 85%). After Boc group elimination with TFA, the product was condensed with (2S,3S)-ethyl hydrogen trans-epoxysuccinate (774 mg) as obtained in Reference Example 8 to yield the title compound (compound 32; 1.55 g) [yield 67%].

Elemental analysis for $C_{26}H_{33}N_3O_7S$ Calcd.: C, 58.74; H, 6.26; N, 7.90; S, 6.03 Found: C, 58.25; H, 6.21; N, 7.80; S, 6.04

$^1$H NMR δ ppm (DMSO-d$_6$) 1.22 (3H, t, J=7.0 Hz), 1.32 (4H, m), 2.38 (3H, s), 2.67 (2H, dt, J=6.0, 6.0 Hz), 2.78 (1H, dd, J=9.5, 13.5 Hz), 2.88–3.08 (3H, m), 3.42 (1H, d, J=1.5 Hz), 3.64 (1H, d, J=1.5 Hz), 4.17 (2H, m), 4.49 (1H, m), 7.16–7.30 (5H, m), 7.39 (2H, d, J=8.0 Hz), 7.47 (1H, t, J=6.0 Hz), 7.67 (2H, d, J=8.0 Hz), 8.08 (1H, t, J=6.0 Hz), 8.65 (1H, d, J=8.5 Hz)

EXAMPLE 36

N-Tosyl-N'-{N-[(2S,3S)-3-trans-carboxyoxirane-2-carbonyl]-L-phenylalanyl}-1,4-diaminobutane monosodium salt In substantially the same manner as in Example 27, the compound 32 (934 mg) was subjected to alkalihydrolysis of ethyl ester, followed by purification by using Diaion HP-20 to yield the title compound (compound 33; 890 mg) (yield 96%)

Elemental analysis for $C_{24}H_{28}N_3O_{7S}Na\cdot H_2O$: Calcd.: C, 53.03; H, 5.56; N, 7.73; S, 5.90; Na, 4.23 Found: C, 52.89; H, 5.72; N, 7.63; S, 5.92; Na, 4.10

$^1H$ NMR δ ppm ($D_2O$) 1.20 (4H, m), 2.39 (3H, s), 2.76 (2H, t, J=6.5H), 2.84–3.12 (4H, m), 3.21 (1H, d, J=2.0 Hz), 3.49 (1H, d, J=2.0 Hz), 4.49 (1H, t, J=7.7 Hz), 7.16–7.36 (5H, m), 7.42 (2H, d, J=8.3 Hz), 7.72 (2H, d, J=8.3 Hz)

EXAMPLE 37

N-butyryl-N'-{N-[(2S,3S)-3-trans-ethoxycarbonyloxirance-2-carbonyl]-L-phenylalanyl}-1,4-diaminobutane After compound 1 (560 mg) was dissolved in pyridine/DMF (1:1, 40 ml), butyryl chloride (300µl) was added under ice-cooling conditions, and the mixture was stirred for one hour under ice-cooling conditions. After the reaction mixture was concentrated, water was added. After adjustment to 2.5, the mixture was extracted with ethyl acetate. The organic layer was washed with a saturated saline, dried over anhydrous sodium sulfate, followed by concentration to dryness to yield an oily product (640 mg). The oily product was dissolved in ethanol (25 ml), to which was added conc. sulfuric acid (212 µl), followed by reflux for one hour. To the reaction mixture was added ice-cooled water, which was subjected to extraction with ethyl acetate, followed by washing with a saturated aqueous sodium hydrogen carbonate solution and a saturated saline, successively. The resultant was dried over anhydrous sodium sulfate, which was then subjected to a silica-gel column chromatography (100 ml) for elution with chloroform eluent supplemented with sequentially added methanol, to yield the title compound (compound 34; 290 mg) as a white powder (yield 50%) from the fraction eluted with 3% (v/v) methanol.

$[\alpha]_D$+46° (c 0.61, MeOH, 24° C.)

Elemental analysis for $C_{23}H_{33}N_3O_6$: Calcd.: C, 61.73; H, 7.43; N, 9.39 Found: C, 61.30; H, 7.46; N, 9.32

$^1H$ NMR δ ppm (DMSO-$d_6$) 0.84 (3H, t, J=7.5 Hz), 1.22 (3H, t, J=7.0 Hz), 1.23–1.42 (4H, m), 1.50 (2H, m), 2.02 (2H, t, J=7.5 Hz), 2.79 (1H, dd, J=9.0, 14.0 Hz), 2.90–3.13 (5H, m), 3.42 (1H, d, J=2.0 Hz), 3.64 (1H, d, J=2.0 Hz), 4.10–4.23 (2H, m), 4.50 (1H, ddd, J=5.0, 9.0, 9.0 Hz), 7.13–7.32 (5H, m), 7.72 (1H, t, J=5.5 Hz), 8.11 (1H, t, J=5.5 Hz), 8.65 (1H, d, J=9.0 Hz)

EXAMPLE 38

N-butyryl-N'-{N-[(2S,3S)-3-trans-carboxyoxirane-2-carbonyl]-L-phenylalanyl}-1,4-diaminobutane monosodium salt In substantially the same manner as in Example 27, compound 34 (122 mg) was subjected to alkali-hydroylsis of ethyl ester, which was desalinized with resin, followed by concentration. The concentrate was lyophilized to give the title compound (compound 35; 62 mg) as a white powder (yield 51%).

$[\alpha]_D$+36° (c 0.53, H20, 24° C.)

Elemental analysis for $C_{21}H_{28}N_3O_6Na\cdot 2H_2O$: Calcd.: C, 52.82; H, 6.75; N, 8.80 Found: C, 53.24; H, 6.70; N, 8.92

$^1H$ NMR δ ppm ($D_2O$) 0.91 (3H, t, J=7.5 Hz), 1.20–1.44 (4H, m), 1.61 (2H, m), 2.22 (2H, t, J=7.5 Hz), 2.98–3.25 (6H, m), 3.25 (1H, d, J=2.0 Hz), 3.52 (1H, d, J=2.0 Hz), 4.55 (1H, t, J=8.0 Hz), 7.22–7.46 (5H, m)

EXAMPLE 39

N-Z-N'-{N-(2S,3S)-trans-ethoxycarbonyloxirane-2-carbonyl]-o-fluoro-L-phenylalanyl}-1,4-diaminobutane In a mixture of dioxanes (10 ml) and water (5 ml), o-fluoro-L-phenylalanine (1.00 g, manufactured by Wako Pure Chemical Industries, Ltd.) was dissolved. To the solution were added, while stirring under ice-cooling conditions, a 1N aqueous solution of sodium hydroxide (5.46 ml) and di-tert-butyl dicarbonate (1.38 ml), followed by stirring for one hour at room temperature. The reaction mixture was concentrated, then the pH was adjusted to 2.5, followed by extraction with ethyl acetate (100 ml ×3). The ethyl acetate layer was washed with water and a saturated saline, dried over anhydrous sodium sulfate. After concentration, the concentrate was crystallized from ethyl acetate—petroleum ether to yield N-Boc-o-fluoro-L-phenylalanine (1.32 g) as colorless crystals (yield 85%). A portion (1.20 g) of this product and N-Z-1,4-diaminobutane (847 mg) were subjected to condensation in substantially the same manner as in Example 5 to yield N-(Boc-o-fluoro-L-phenylalanyl)-N'-1,4-diaminobutane (1.77 g) as a white powder (yield 95%). After Boc group elimination with TFA, the product was condensed with (2S,3S)-ethyl hydrogen trans-epoxyxuccinate (522 mg) as obtained in Reference Example 8 to yield the title compound (compound 36; 1.39 g) as a white powder (yield 81%).

$[\alpha]_D$+13° (c 0.56, $CHCl_3$, 22° C.)

Elemental analysis for $C_{27}H_{32}N_3O_7F\cdot 0.25CHCl_3$ Calcd.: C, 58.51; It, 5.81; N, 7.51; F, 3.40 Found: C, 58.59; H, 5.83; N, 7.60; F, 3.50

$^1H$ NMR δ ppm ($CDCl_3$) 1.30 (3H, t, J=7.2 Hz), 1.45 (4H, m), 3.05 (1H, dd, J=8.2, 13.9 Hz), 3.17 (5H, m), 3.22 (1H, d, J=1.9 Hz), 3.62 (1H, d, J=1.9 Hz), 4.24 (2H, m), 4.62 (1H, m), 4.92 (1H, br s), 5.10 (2H, s), 6.34 (1H, br s), 6.84 (1H, d, J=8.1 Hz), 7.06 (2H, m), 7.21 (2H, m), 7.35 (5H, m)

EXAMPLE 40

N-Z-N'-{N-(2S,3S)-3-trans-carboxyoxirane-2-carbonyl]-o-fluoro-L-phenylalanyl}-1,4-diaminobutane In substantially the same manner as in Example 6, compound 36 (1.29 g) was subjected to alkali hydrolysis to yield the title compound (compound 37; 1.07 g) as a white powder (yield 88%).

Elemental analysis for $C_{25}H_{28}N_3O_7F\cdot 0.25H_2O$: Calcd.: C, 59.34; H, 5.68; N, 8.30, F, 3.75 Found: C, 59.32; H, 5.66; N, 8.22, F, 3.76

$^1H$ NMR δ ppm (DMSO-$d_6$) 1.32 (4H, m), 2.84 (1H, dd, J=9.0, 13.9 Hz), 2.96 (4H, m), 3.06 (1H, dd, J=5.9, 13.9 Hz), 3.30 (1H, d, J=1.8 Hz), 3.59 (1H, d, J=1.8 Hz), 4.55 (1H, dt, J=6.0, 8.8 Hz), 5.00 (2H, s), 7.11 (2H, m), 7.24 (3H, m), 7.34 (5H, m), 8.10 (1H, t, J=5.6 Hz), 8.59 (1H, d, J=8.7 Hz)

EXAMPLE 41

N-{N-(2S,3S)-3-trans-carboxyoxirane-2-carbonyl]-o-fluoro-L-phenylalanyl}-1,4-diaminobutane In substantially the same manner as in Example 7, compound 37 (970 mg) was subjected to catalytic reduction to deprotect the Z group, followed by lyophilization to yield the title compound (compound 38; 670 mg) as a white powder (yield 94%).

$[\alpha]_D$+46° (c 0.52, 0.1N HCl, 25° C.)

Elemental analysis for $C_{17}H_{22}N_3O_5F \cdot 0.8H_2O$: Calcd.: C, 53.48; H, 6.23; N, 11.01; F, 4.98 Found: C, 53.43; H, 6.03; N, 10.83; F, 4.88

$^1$H NMR δ ppm (D$_2$O) 1.50 (4It,m), 2.95 (2H, t, J=7.3 Hz), 3.07 (1H, dd, J=8.1, 13.9 Hz), 3.15 (2H, m), 3.19 (1H, m), 3.25 (1H, d, J=1.9 Hz), 3.50 (1H, d, J=2.1 Hz), 4.57 (1H, dd, J=7.6, 7.9 Hz), 7.18 (2H, m), 7.30 (2H, m)

EXAMPLE 42

N-Z-N'-{N-[(2S,3S)-3-trans-ethoxycarboxyoxirane-2-carbonyl]-N$^{im}$-tosyl-L-histidyl}-1,4-diaminobutane In substantially the same manner as in Example 5, N-Z-1,4-diaminobutane (1.20 g) was subjected to condensation with Boc-N$^{im}$-tosyl-L-histidine (2.44 g, manufactured by Peptide Institute, Inc.) to yield N-(Boc-N$^{im}$-tosyl-L-histidyl)-N'-Z-1,4-diaminobutane (3.27 g) as a white powder (yield 99%). After Boc group elimination with TFA, the product was condensed with (2S,3S)-ethyl hydrogen trans-epoxysuccinate (776 mg) as obtained in Reference Example 8 to yield the title compound (compound 39; 2.42 g) as a white powder (yield 84%).

$[\alpha]_D$+31° (c 0.54, CHCl$_3$, 22° C.)

Elemental analysis for $C_{31}H_{37}N_5O_9S \cdot H_2O$: Calcd.: C, 55.26; H, 5.83; N, 10.40; S, 4.76 Found: C, 55.23; H, 5.52; N, 10.39; S, 4.74

$^1$H NMR δ ppm (CDCl$_3$) 1.31 (3H, t, J=7.1 Hz), 1.42 (4H, m), 2.44 (3H, s), 2.83 (1H, dd, J=6.4, 14.8 Hz), 3.02 (1H, dd, J=5.4, 14.8 Hz), 3.16 (4H, m), 3.54 (1H, d, J=1.8 Hz), 3.67 (1H, d, J=1.8 Hz), 4.26 (2H, m), 4.59 (1H, m), 5.00 (1H, br s), 5.10 (2H, s), 6.80 (1H, br s), 7.09 (1H, m), 7.27–7.39 (7H, m), 7.51 (1H, d, J=7.3 Hz), 7.81 (2H, d, J=8.4 Hz), 7.94 (1H, d, J=1.2 Hz)

EXAMPLE 43

N-Z-N'-{N-(2S,3S)-3-trans-carboxyoxirane-2-carbonyl]-L-histidyl}-1,4-diaminobutane In substantially the same manner as in Example 6, compound 39 (2.30 g) was subjected to alkali hydrolysis to yield the title compound (compound 40; 1.46 g) (yield 88%).

Elemental analysis for $C_{22}H_{27}N_5O_7 \cdot 2H_2O$: Calcd.: C, 51.86; H, 6.13; N, 13.75 Found: C, 51.89; H, 6.09; N, 13.86

$^1$H NMR δ ppm (D$_2$O) 1.37 (4H, m), 3.07 (6H, m), 3.27 (1H, d, J=2.0 Hz), 3.51 (1H, d, J=2.0 Hz), 4.57 (1H, dd, J=6.7, 8.0 Hz), 5.08 (2H, s), 7.05 (1H, s), 7.39 (5H, m), 8.02 (1H, s)

EXAMPLE 44

N-{N-(2S,3S)-3-trans-carboxyoxirane-2-carbonyl]-L-histidyl}-1,4-diaminobutane

In substantially the same manner as in Example 7, compound 40 (960 mg) was subjected to catalytic reduction to deprotect Z group, followed by lyophilization to give the title compound (compound 41; 455 mg) as a white powder (yield 47%).

$[\alpha]_D$+220 (c 0.57, 0.1N HCl, 22° C.)

Elemental analysis for $C_{14}H_{21}N_5O_5 \cdot 2.6H_2O$: Calcd.: C, 43.54; H, 6.84; N, 18.14 Found: C, 43.45; H, 6.89; N, 18.10

$^1$H NMR δ ppm (D$_2$O) 1.61 (4H, m), 3.03 (2H, t, J=7.3 Hz), 3.15 (1H, dd, J=8.9, 15.2 Hz), 3.26 (3H, m), 3.34 (1H, d, J=2.0 Hz), 3.57 (1H, d, J=2.1 Hz), 4.67 (1H, dd, J=6.0, 8.9 Hz), 7.25 (1H, br s), 8.39 (1H, d, J=1.1 Hz)

EXAMPLE 45

N-Z-N'-{N-[(2S,3S)-3-trans-ethoxycarbonyloxirane-2-carbonyl]-N$^\epsilon$-Z-L-lysyl}-1,4-diaminobutane In substantially the same manner as in Example 5, N-Z-1,4-diaminobutane (1.20 g) was condensed with Boc-L-Lys(Z)-OH (2.26 g, Peptide Institute, Inc.) to yield N-(Boc-N$^\epsilon$-Z-L-lysyl)-N'-Z-1,4-diaminobutane (3.32 g) as a white powder (yield, quantitative). After Boc group elimination with TFA, the product was condensed with (2S,3S)-ethyl hydrogen trans-epoxysuccinate (661 mg) as obtained in Reference Example 8 to yield the title compound (compound 42; 2.11 g) as a white powder (yield 82%).

$[\alpha]_D$+10° (c 0.60, CHCl$_3$, 22° C.)

Elemental analysis for $C_{32}H_{42}N_4O_9 \cdot 0.5H_2O$: Calcd.: C, 60.46; H, 6.82; N, 8.81 Found: C, 60.30; H, 6.65; N, 8.85

$^1$H NMR δ ppm (CDCl$_3$) 1.30 (3H, t, J=7.2 Hz), 1.30 (2H, m), 1.52 (6H, m), 1.62 (1H, m), 1.83 (1H, m), 3.17 (4H, m), 3.26 (2H, m), 3.51 (1H, d, J=1.6 Hz), 3.68 (1H, d, J=1.8 Hz), 4.25 (2H, m), 4.32 (1H, m), 4.98 (1H, m), 5.08 (5H, m), 6.44 (1H, br s), 6.89 (1H, d, J=7.2 Hz), 7.34 (10H, m)

EXAMPLE 46

N-Z-N'-{N-[(2S,3S)-3-trans-carbonyloxirane-2-carbonyl]-N$^\epsilon$-Z-L-lysyl}-1,4-diaminobutane In substantially the same manner as in Example 6, compound 42 (2.00 g) was subjected to alkali hydrolysis to yield the title compound (compound 43; 1.40 g) as a white powder (yield 73%).

Elemental analysis for $C_{30}H_{38}N_4O_9 \cdot 0.3CHCl_3$: Calcd.: C, 57.36; H, 6.08; N, 8.83 Found: C, 57.30; H, 6.13; N, 8.99

$^1$H NMR δ ppm (DMSO-d$_6$ +D$_2$O) 1.23 (2H, m), 1.38 (6H, m), 1.58 (2H, m), 2.98 (6H, m), 3.11 (1H, d, J=1.9 Hz), 3.37 (1H, d, J=1.9 Hz), 4.19 (1H, m), 5.00 (4H, s), 7.35 (10H, m), 8.09 (1H, t, J=5.4 Hz), 8.22 (1H, d, J=8.0 Hz)

EXAMPLE 47

N-Z-N'-{O-benzyl-N-[(2S,3S)-3-trans-ethoxycarbonyloxirane-2-carbonyl]-L-seryl}-1,4-diaminobutane In substantially the same manner as in Example 5, N-Z-1,4-diaminobutane (1.20 g) was condensed with Boc-L-Ser(Bzl)-OH (1.76 g, manufactured by Peptide Institute, Inc.) to yield N-(O-benzyl-Boc-L-seryl)-N'-Z-1,4-diaminobutane (2.42 g) as a white powder (yield 90%). After Boc group elimination with TFA, the product was condensed with (2S,3S)-ethyl hydrogen trans-epoxysuccinate (677 mg) as obtained in Reference Example 8 to yield the title compound (compound 44; 4.67 g) as a white powder (yield 73%).

$[\alpha]_D$+41° (c 0.55, CHCl$_3$, 22° C.)

Elemental analysis for $C_{28}H_{35}N_3O_8 \cdot 0.5H_2O$: Calcd.: C, 61.08; H, 6.59; N, 7.63 Found: C, 60.91; H, 6.31; N, 7.77

$^1$H NMR δ ppm (CDCl$_3$) 1.30 (3H, t, J=7.1 Hz), 1.48 (4H, m), 3.15 (2H, m), 3.27 (2H, m), 3.44 (1H, d, J=1.8 Hz), 3.48 (1H, dd, J=7.5, 9.1 Hz), 3.69 (1H, d, J=1.9 Hz), 3.82 (1H, dd, J=4.3, 9.2 Hz), 4.25 (2H, m), 4.48 (1H, d, J=11.8 Hz), 4.49 (1H, m), 4.57 (1H, d, J=11.8 Hz), 4.88 (1H, br s), 5.09 (2H, s), 6.60 (1H, br s), 7.05 (1H, d, J=6.8 Hz), 7.34 (10H, m)

EXAMPLE 48

N-Z-N'-{O-benzyl-N-[(2S,3S)-3-trans-carboxyoxirane-2-carbonyl]-L-seryl}-1,4-diaminobutane In substantially the same manner as in Example 6, the compound 44 (1.55 g) was subjected to alkali hydrolysis to yield the title compound (compound 45; 1.30 g) as a white powder (yield 89%).

Elemental analysis for $C_{26}H_{31}N_3O_8 \cdot 0.67H_2O$: Calcd.: C, 59.42; H, 6.20; N, 8.00 Found: C, 59.44; H, 6.09; N, 7.79

$^1$H NMR 3ppm (DMSO-d$_6$) 1.38 (4H, m), 2.97 (2H, m), 3.05 (2H, m), 3.46 (1H, d, J=1.8 Hz), 3.60 (2H, m) 3.75 (1H, d, J=1.8 Hz), 4.48 (2H, s), 4.52 (1H, m), 4.99 (2H, s), 7.23 (1H, t, J=5.5 Hz), 7.33 (10H, m), 8.12 (1H, t, J=5.7 Hz), 8.67 (1H, d, J=8.2 Hz)

EXAMPLE 49

N-{O-benzyl-N-[(2S,3S)-3-trans-carboxyoxirane-2-carbonyl]-L-seryl}-1,4-diaminobutane (compound 46),
N-{N-[(2S,3S)-3-trans-carboxyoxirane-2-carbonyl]-L-seryl}-1,4-diaminobutane (compound 47)

In substantially the same manner as in Example 7, compound 45 (800 mg) was subjected to catalytic reduction to deprotect Z group, and then subjected to a column chromatography with HP-20 (100 ml). Fractions eluted with water were lyophilized to yield compound 47 (310 mg) as a white powder (yield 69%), and fractions elated with 50% (v/v) methanol were lyophilized to yield compound 46 (60.0 mg) as a white powder (yield 10%).

Compound 46

$[α]_D$+33° (c 0.61, 0.1N HCl, 25° C.)

Elemental analysis for $C_{18}H_{25}N_3O_6 \cdot 1H_2O$: Calcd.: C, 54.15; H, 6.87; N, 10.53 Found: C, 54.01; H, 6.76; N, 10.56

$^1$H NMR δ ppm (D$_2$O) 1.57 (4H, m), 2.95 (2H, m), 3.23 (2H, m), 3.39 (1H, d, J=2.1 Hz), 3.58 (1H, d, J=2.0 Hz), 3.81 (1H, dd, J=4.8, 10.5 Hz), 3.87 (1H, dd, J=5.6, 10.5 Hz), 4.49 (1H, dd, J=4.9, 5.4 Hz), 4.56 (1H, d, J=12.0 Hz), 4.60 (1H, d, J=12.0 Hz), 7.41 (5H, m)

Compound 47

$[α]_D$+30° (c 0.53, 0.1N HCl, 25° C.)

Elemental analysis for $C_{11}H_{19}N_3O_6 \cdot 0.5H_2O$: Calcd.: C, 44.29; H, 6.76; N, 14.09 Found: C, 44.37; H, 6.68; N, 14.10

$^1$H NMR δ ppm (D$_2$O) 1.61 (4H, m), 3.01 (2H, m), 3.27 (2H, m), 3.44 (1H, d, J=2.1 Hz), 3.63 (1H, d, J=2.1 Hz), 3.88 (2H, d, J=5.4Hz), 4.40 (1H, t, J=5.1 Hz)

EXAMPLE 50

N-Boc-N'-{S-trityl-N-[(2S,3S)-3-trans-ethoxycarbonyloxirane-2-carbonyl]-L-cysteinyl}-1,4-diaminobutane N-Z-1,4-Diaminobutane (10.0 g) was dissolved in dichloromethane (100 ml), to which was added di-tert-butyl dicarbonate (10.3 ml). The mixture was stirred for one hour at room temperature, which was left standing overnight. The reaction mixture was washed with a 10% aqueous solution of citric acid, water, a saturated aqueous solution of sodium hydrogen carbonate, water, and a saturated saline, successively, which was dried over anhydrous sodium sulfate, followed by concentration to dryness to give N-Z-N'-Boc-1,4-diaminobutane (14.6 g) as a white powder (yield quantitative). A portion of this product (1.74 g) was dissolved in methanol (60 ml). To the solution was added a mixture of palladium/activated carbon [10%(w/w), 180 mg], followed by stirring for 2 hours at room temperature. The catalyst was filtered off, and the filtrate was concentrated to dryness to yield N-Boc-1,4-diaminobutane (1.02 g) as a white powder (yield quantitative). The compound thus obtained was condensed with Fmoc-S-trityl-L-cysteine (3.48 g, Peptide Institute, Inc.) in substantially the same manner as in Example 5 to give N-(Fmoc-S-trityl-L-cysteinyl)-N'-Boc-1,4-diaminobutane (3.25 g) as a white powder (yield 80%). A portion of this product (3.15 g) was dissolved in dichloromethane (28.8 ml), to which was added piperidine (3.2 ml), followed by stirring for one hour at room temperature. The reaction mixture was concentrated, which was subjected to a silica-gel column chromatography (200 ml). The column was washed with 50% (v/v) ethyl acetate/hexane, followed by elution with 100% methanol. The eluate was concentrated to dryness to give N-(S-trityl-L-cysteinyl)-N'-Boc-1,4-diaminobutane (1.92 g) as a white powder (yield 85%). A portion (1.82 g) of this product was condensed with (2S,3S)-ethyl hydrogen trans-epoxysuccinate (546 mg) as obtained in Reference Example 8 to yield the title compound (compound 48; 1.55 g) as a white powder (yield 67%).

$[α]_D$+30° (c 0.51, CHCl$_3$, 22° C.)

Elemental analysis for $C_{37}H_{45}N_3O_7S \cdot 0.25CHCl_3$: Calcd.: C, 63.40; H, 6.46; N, 5.95; S, 4.54 Found: C, 63.26; H, 6.40; N, 6.07; S, 4.53

$^1$H NMR δ ppm (CDCl$_3$) 1.32 (3H, t, J=7.1 Hz), 1.43 (9H, s), 1.46 (4H, m), 2.52 (1H, dd, J=6.0, 13.0 Hz), 2.65 (1H, dd, J=7.4, 13.1 Hz), 3.08 (2H, m), 3.18 (2H, m), 3.44 (1H, d, J=1.8 Hz), 3.61 (1H, d, J=1.8 Hz), 3.94 (1H, m), 4.26 (2H, m), 4.56 (1H, br s), 6.00 (1H, br s), 6.55 (1H, d, J=7.9 Hz), 7.20–7.44 (15H, m)

EXAMPLE 51

N-Boc-N'-{S-trityl-N-[(2S,3S)-3-trans-carboxyoxirane-2-carbonyl}-L-cysteinyl}-1,4-diaminobutane In substantially the same manner as in Example 6, the compound 48 (1.45 g) was subjected to alkali hydrolysis to yield the title compound (compound 49; 1.32 g) as a white powder (yield 95%).

Elemental analysis for $C_{35}H_{41}N_3O_7S \cdot 0.75H_2O$: Calcd.: C, 63.57; H, 6.48; N, 6.35; S, 4.85 Found: C, 63.51; H, 6.47; N, 6.12; S, 4.79

$^1$H NMR δ ppm (DMSO-d$_6$) 1.32 (4H, m), 1.36 (9H, s), 2.34 (1H, d, J=6.6 Hz), 2.87 (2H, m), 2.99 (2H, m), 3.42 (1H, d, J=1.8 Hz), 3.68 (1H, d, J=1.8 Hz), 4.35 (1H, dt, J=8.2, 6.6 Hz), 6.74 (1H, t, J=5.6 Hz), 7.29 (15H, m), 8.06 (1H, t, J=5.4 Hz), 8.74 (1H, d, J=8.6 Hz)

EXAMPLE 52

N-{S-trityl-N-[(2S,3S)-3-trans-carboxyoxirane-2-carbonyl]-L-cysteinyl}-1,4-diaminobutane The compound 49 (600 mg) was dissolved in dichloromethane (10 ml), to which was added TFA (4 ml). The mixture was left standing for 2 hours at room temperature. The reaction mixture was concentrated, to which was added a 2% aqueous solution of sodium hydrogen carbonate to adjust the pH to 7.5, followed by extraction seven times with chloroform:methanol (2:1). The extract was washed with water, which was then concentrated to dryness to yield the title compound (compound 50; 390 mg) as a white powder (yield 77%).

$[\alpha]_D$+31° (c 0.74, MeOH, 26° C.)

Elemental analysis for $C_{30}H_{33}N_3O_5S \cdot 2.5H_2O$: Calcd.: C, 60.79; H, 6.46; N, 7.09; S, 5.41 Found: C, 60.66; H, 5.97; N, 7.14; S, 5.72

$^1$H NMR δ ppm (DMSO-$d_6$) 1.44 (4H, m), 2.34 (1H, dd, J=5.0, 11.7 Hz), 2.47 (1H, dd, J=9.2, 11.7 Hz), 2.72 (2H, m), 2.99 (2H, m), 3.05 (1H, d, J=1.3 Hz), 3.36 (1H, d, J=1.2 Hz), 4.18 (1H, dt, J=5.3, 8.6 Hz), 7.30 (15H, m), 8.11 (2H, br s), 8.52 (1H, br s), 9.60 (1H, d, J=8.3 Hz)

EXAMPLE 53

N-Z-N'-{N-[(2S,3S)-3-trans-ethoxycarbonyloxirane-2-carbonyl]-L-glutaminyl}-1,4-diaminobutane In substantially the same manner as in Example 5, N-Z-1,4-diaminobutane (1.57 g) was condensed with Boc-L-Gln-OH (1.92 g, Peptide Institute, Inc.) to give N-(Boc-L-glutaminyl)-N'-Z-1,4-diaminobutane (3.06 g) as a white powder (yield 96%). After Boc group elimination with TFA, the product was condensed with (2S,3S)-ethyl hydrogen trans-epoxysuccinate (602 mg) as obtained in Reference Example 8 to yield the title compound (compound 51:734 mg) as a white powder (yield 44%).

$[\alpha]_D$+44° (c 0.52, DMF, 24° C.)

Elemental analysis for $C_{23}H_{32}N_4O_8$: Calcd.: C, 56.09; H, 6.55; N, 11.38 Found: C, 55.80; H, 6.15; N, 11.63

$^1$H NMR δ ppm (DMSO-$d_6$) 1.24 (3H, t, J=7.0 Hz), 1.31–1.48 (4H, m), 1.63–1.95 (2H, m), 2.05 (2H, t, J=7.5 Hz), 2.91–3.13 (4H, m), 3.60 (1H, d, J=1.5 Hz), 3.71 (1H, d, J=1.5 Hz), 4.11–4.27 (3H, m), 4.99 (2H, s), 6.74 (1H, br s), 7.21 (1H, t, J=5.5 Hz), 7.21–7.41 (6H, m), 8.01 (1H, t, J=5.0 Hz), 8.53 (1H, d, J=8.0 Hz)

EXAMPLE 54

N-Z-N'-{N-[(2S,3S)-3-trans-carboxyoxirane-2-carbonyl]-L-glutaminyl}-1,4-diaminobutane In substantially the same manner as in Example 6, the compound 51 (665 mg) was subjected to alkali hydrolysis. After the reaction mixture was concentrated, water was added. After adjustment to pit 2.5, the mixture was extracted with ethyl acetate/isobutanol (1:1). The organic layer was washed with a saturated saline, followed by concentration to yield the title compound (compound 52; 284 mg) as a white powder (yield 45%).

$[\alpha]_D$+35° (c 0.53, DMF, 24° C.)

Elemental analysis for $C_{21}H_{28}N_4O_8 \cdot 2H_2O$: Calcd.: C, 50.40; H, 6.44; N, 11.19 Found: C, 50.42; H, 5.74; N, 11.25

$^1$H NMR δ ppm (DMSO-$d_6$) 1.30–1.46 (4H, m), 1.64–1.96 (2H, m), 2.05 (2H, t, J=7.5 Hz), 2.90–3.11 (4H, m), 3.34 (1H, d, J=1.5 Hz), 3.54 (1H, d, J=1.5 Hz), 4.21 (1H, dt, J-8.0, 5.0 Hz), 5.00 (2H, s), 6.76 (1H, br s), 7.22–7.41 (7H, m), 8.07 (1H, t, J=5.5 Hz), 8.47 (1H, d, J=8.0 Hz)

EXAMPLE 55

N-{N-[(2S,3S)-3-trans-carboxyoxirane-2-carbonyl]-L-glutaminyl}-1,4-diaminobutane In substantially the same manner as in Example 7, the compound 52 (400 mg) was subjected to catalytic reduction to deprotect Z group, followed by lyophilization to yield the title compound (compound 53; 284 mg) as a white powder (yield quantitative).

$[\alpha]_D$+18° (c 0.55, $H_2O$, 20° C.)

Elemental analysis for $C_{13}H_{22}N_4O_6 \cdot 4.5H_2O$: Calcd.: C, 37.95; H, 7.59; N, 13.62 Found: C, 38.30; H, 6.40; N, 13.14

$^1$H NMR δ ppm ($D_2O$) 1.50–1.70 (4H, m), 1.89–2.20 (2H, m), 2.38 (2H, t, J=7.5 Hz), 2.98 (2H, t, J=7.0 Hz), 3.25 (2H, t, J=6.0 Hz), 3.46 (1H, d, J=2.0 Hz), 3.58 (1H, d, J=2.0 Hz), 4.28 (1H, dd, J=5.0, 9.0 Hz)

EXAMPLE 56

N-Z-N'-{γ-benzyl-N-[(2S,3S)-3-trans-ethoxycarbonyloxirane-2-carbonyl]-L-glutamyl}-1,4-diaminobutane In substantially the same manner as in Example 5, N-Z-1,4-diaminobutane (1.00 g) was condensed with Boc-L-Glu(Bzl)-OH (1.67 g, manufactured by Peptide Institute, Inc.) to give N-(Boc-γ-benzyl-L-glutamyl)-N'-Z-1,4-diaminobutane (2.43 g) as a white powder (yield quantitative). After Boc group elimination with TFA, the product was condensed with (2S,3S)ethyl hydrogen trans-epoxysuccinate (400 mg) as obtained in Reference Example 8 to yield the title compound (compound 54; 840 mg) as a white powder (yield 58%).

$[\alpha]_D$+13° (c 0.60, $CHCl_3$, 24° C.)

Elemental analysis for $C_{30}H_{37}N_3O_9$: Calcd.: C, 61.74; H, 6.39; N, 7.20 Found: C, 61.29; H, 6.49; N, 7.10

$^1$H NMR δ ppm ($CDCl_3$) 1.30 (3H, t, J=7.0 Hz), 1.43–1.58 (4H, m), 1.85–2.02 (1H, m), 2.03–2.20 (1H, m), 2.38 (1H, dt, J=17.0, 6.5 Hz), 2.52 (1H, dt, J=17.0, 7.0 Hz), 3.10–3.32 (4H, m), 3.51 (1H, d, J=2.0 Hz), 3.67 (1H, d, J=2.0 Hz), 4.18–4.32 (2H, m), 4.42 (1H, dt, J=5.5, 7.5 Hz), 4.98 (1H, t, J=5.5 Hz), 5.09 (2H, s), 5.10 (1H, d, J=12.0 Hz), 5.15 (1H, d, J=12.0 Hz), 6.63 (1H, t, J=5.0 Hz), 7.11 (1H, d, J=7.5 Hz), 7.26–7.41 (10H, m)

EXAMPLE 57

N-Z-N'-{γ-Methyl-N-[(2S,3S)-3-trans-methoxycarbonyloxirane-2-carbonyl]-L-glutamyl}-1,4-diaminobutane The compound 54 (585 mg) was dissolved in methanol (60 ml), to which was added, under ice-cooling conditions, a 1N aqueous solution of sodium hydroxide (500 μl), and the mixture was stirred for one hour under ice-cooling conditions. After the reaction mixture was concentrated, water was added. After adjustment to pH 2.5, the mixture was extracted with ethyl acetate. The organic layer was washed with a saturated saline, dried over anhydrous sodium sulfate, followed by subjecting to a silica-gel column chromatography (50 ml) for elution with hexane eluent supplemented with sequentially added ethyl acetate. From the fraction eluted with 80%–100% (v/v) ethyl acetate, the title compound (compound 55; 338 mg) was obtained as a white powder (yield 69%).

$^1$H NMR δ ppm (DMSO-$d_6$) 1.30–1.46 (4H, m), 1.70–2.01 (2H, m), 2.30 (2H, t, J=7.5 Hz), 2.90–3.12 (4H, m), 3.58 (3H, s), 3.65 (1H, d, J=2.0 Hz), 3.72 (4H, m), 4.26 (1H, ddd, J=6.0, 8.0, 8.0 Hz), 5.00 (2H, s), 7.24 (1H, t, J=5.5 Hz), 7.26–7.42 (5H, m), 8.07 (1H, t, J=5.5 Hz), 8.61 (1H, d, J=8.0 Hz)

EXAMPLE 58

N-{N-[(2S,3S)-3-trans-ethoxycarbonyloxirane-2-carbonyl]-L-phenylalanyl}-1,4-diaminobutane ½ sulfate After compound 1 (500 mg) was dissolved in ethanol (20 ml), conc. sulfuric acid (115μl) was added. The mixture was refluxed for 70 minutes and then ice-cooled water was added. After adjustment to pH 5.7, the mixture was subjected to a column chromatography with CM-sephadex C-25 (Na type, 50 ml), then elution was carried out with a 0.03M aqueous solution of sodium sulfate. The eluate was desalinized by using Diaion HP-20 (30 ml) to yield the title compound (compound 56; 503 mg) as a white powder (yield 82%).

$[α]_D$+54° (c 0.53, $H_2O$, 20° C.)

Elemental analysis for $C_{19}H_{27}N_3O_5 \cdot ½H_2SO_4 \cdot H_2O$: Calcd.: C, 51.34; H, 6.80; N, 9.45; S, 3.61 Found: C, 51.60; H, 6.80; N, 9.34; S, 3.66

$^1$H NMR δ ppm ($D_2O$) 1.29 (3H, t, J=7.0 Hz), 1.36–1.57 (4H, m), 2.86–3.23 (6H, m), 3.47 (1H, d, J=2.0 Hz), 3.72 (1H, d, J=2.0 Hz), 4.27 (2H, q, J=7.0 Hz), 4.57 (1H, t, J=8.0 Hz), 7.23–7.44 (5H, m)

EXAMPLE 59

N-{N-[(2S,3S)-3-trans-ethoxycarbonyloxirane-2-carbonyl]-L-phenylalanyl}-1,4-diaminobutane octanesulfonate In substantially the same manner as in Example 58, the compound 1 (309 mg) was esterified, which was subjected to a column chromatography with CM-sephadex C-25 (Na type, 20 ml). Elution was carried out with a 0.2M saline. The eluate was desalinized by using Diaion HP-20 (15 ml) to give N-{N-[(2S,3S)-3-trans-ethoxycarbonyloxirane-2-carbonyl]-L-phenylalanyl}-1,4-diaminobutane monohydrochloride (315 mg) (yield 88%). The compound thus obtained (105 mg) was allowed to pass through a column packed with Amberlite IRA-402 (octanesulfonic acid type, 5 ml), then the column was washed with water (10 ml). The effluents and washings were combined, and the mixture was concentrated and then lyophilized to yield the title compound (compound 57; 127 mg) as a white powder.

$[α]_D$+40° (c 0.67, MeOH, 24° C.)

Elemental analysis for $C_{19}H_{27}N_3O_5 \cdot C_8H_{17}SO_3H \cdot 0.5H_2O$: Calcd.: C, 55.84; H, 7.98; N, 7.24; S, 5.52 Found: C, 55.66; H, 7.98; N, 7.19; S, 5.51

$^1$H NMR δ ppm ($D_2O$) 0.87 (3H, t, J=7.0 Hz), 1.30 (3H, t, J=7.0 Hz), 1.22–1.60 (14H, m), 1.66–1.80 (2H, m), 2.85–3.25 (8H, m), 3.49 (1H, d, J=2.0 Hz), 3.74 (1H, d, J=2.0 Hz), 4.29 (2H, q, J=7.0 Hz), 4.58 (1H, t, J=8.0 Hz), 7.24–7.46 (5H, m)

EXAMPLE 60

N-{O-benzyl-N-[(2S,3S)-3-trans-ethoxycarbonyloxirane-2-carbonyl]-L-tyrosyl} morpholine In substantially the same manner as in Example 5, morpholine (1.41 ml) and Boc-L-Tyr(Bzl)-OH (6.00 g, manufactured by Peptide Institute, Inc.) were condensed to give N-(O-benzyl-Boc-L-tyrosyl)morpholine (8.10 g) as a white powder (yield quantitative). After Boc group elimination with TFA, the product was condensed with (2S,3S)-ethyl hydrogen trans-epoxysuccinate (2.76 g) as obtained in Reference Example 8 to yield the title compound (compound 58; 6.14 g) as a white powder (yield 81%).

$[α]_D$+39° (c 0.58, $CHCl_3$, 24° C.)

Elemental analysis for $C_{26}H_{30}N_2O_7 \cdot 0.7H_2O$: Calcd.: C, 63.07; H, 6.39; N, 5.66, Found: C, 63.04; H, 6.00; N, 5.78

$^1$H NMR δ ppm ($CDCl_3$) 1.31 (3H, t, J=7.1 Hz), 2.91 (2H, d, J=7.3 Hz), 2.98 (1H, ddd, J=3.0, 6.5, 13.3 Hz), 3.05 (1H, ddd, J=2.9, 6.6, 11.6 Hz), 3.31 (1H, ddd, J=3.1, 6.7, 13.4 Hz), 3.37 (1H, d, J=1.8 Hz), 3.45 (1H, ddd, J=2.9, 6.4, 11.4 Hz), 3.50 (1H, m), 3.55 (2H, t, J=4.3 Hz), 3.60 (1H, m), 3.64 (1H, d, J=1.8 Hz), 4.25 (2H, m), 5.05 (1H, m), 5.06 (2H, s), 6.91 (2H, d, J=8.6 Hz), 6.95 (1H, d, J=8.8 Hz), 7.07 (2H, d, J=8.6 Hz), 7.40 (5H, m)

EXAMPLE 61

N-{(N-[(2S,3S)-3-trans-ethoxycarbonyloxirane-2-carbonyl]-L-tyrosyl}morpholine

After the compound 58 (5.98 g) was dissolved in ethanol (200 ml), palladium/activated carbon [10%(w/w), 600 mg] was added. The mixture was stirred for 5 hours at room temperature under hydrogen atmosphere. The catalyst was filtered off, then the filtrate was concentrated, which was subjected to silica-gel column chromatography (500 ml) for elution with a chloroform eluent supplemented with sequentially added methanol. From the fraction eluted with 2% (v/v) methanol, the title compound (compound 59; 4.04 g) was obtained as a white powder (yield 83%).

$[α]_D$+44° (c 0.55, $CHCl_3$, 25° C.)

Elemental analysis for $C_{19}H_{24}N_2O_7 \cdot 0.27CHCl_3$: Calcd.: C, 54.50; H, 5.76; N, 6.60 Found: C, 54.44; H, 5.63; N, 6.64

$^1$H NMR δ ppm ($CDCl_3$) 1.31 (3H, t, J=7.2 Hz), 2.87 (1H, dd, J=6.4, 13.5), 2.93 (1H, dd, J=8.0, 13.5), 3.08 (1H, ddd, J=2.9, 6.4, 13.0 Hz), 3.17 (1H, ddd, J=2.9, 6.4, 11.3 Hz), 3.38 (1H, ddd, J=2.9, 6.4, 12.9 Hz), 3.39 (1H, d, J=1.8 Hz), 3.51 (1H, ddd, J=2.9, 6.5, 11.4 Hz), 3.57 (2H, m), 3.60 (2H, m), 3.66 (1H, d, J=1.8 Hz), 4.25 (2H, m), 5.08 (1H, dt, J=8.1, 6.7 Hz), 6.49 (1H, s), 6.75 (2H, d, J=8.5 Hz), 7.00 (2H, d, J=8.5 Hz), 7.08 (1H, d, J=8.3 Hz)

EXAMPLE 62

N-{N-[(2S,3S)-3-trans-carboxyoxirane-2-carbonyl]-L-tyrosyl}morpholine mosodium salt In substantially the same manner as in Example 27, the compound 59 (300 mg) was subjected to alkali hydrolysis. The hydrolyzate was desalinized with resin, which was then concentrated and lyophilized to yield the title compound (compound 60; 233 mg) as a white powder (yield 79%).

$[\alpha]_D$+72° (c 0.60, $H_2O$, 25° C.)

Elemental analysis for $C_{17}H_{19}N_2O_7Na \cdot H_2O$: Calcd.: C, 50.50; H, 5.23; N, 6.93; Na, 5.69 Found: C, 50.68; H, 5.41; N, 7.04; Na, 5.70

$^1H$ NMR δ ppm ($D_2O$) 2.93 (1H, dd, J=9.2, 13.3 Hz), 2.96 (1H, m), 3.03 (1H, dd, J=6.6, 13.4 Hz), 3.25 (1H, ddd, J=2.8, 5.3, 13.4 Hz), 3.37 (1H, d, J=2.1 Hz), 3.41 (1H, m), 3.44 (2H, m), 3.53 (1H, d, J=2.1 Hz), 3.58 (2H, m), 3.67 (1H, m), 5.01 (1H, dd, J=6.6, 9.2 Hz), 6.88 (2H, d, J=8.6 Hz), 7.15 (2H, d, J=8.6 Hz)

EXAMPLE 63

N-{N-[(2S,3S)-3-trans-ethoxycarbonyloxirane-2-carbonyl]-3-(3,4-dihydroxyphenyl)-L-alanyl} morpholine In a mixture solvent of dioxane (40 ml) and water (20 ml) was dissolved 3-(3,4-dihydroxyphenyl)-L-alanine (3.94 g, manufactured by Tokyo Kasei Co., Ltd.). To the solution were added, while stirring under ice-cooling conditions, a 1N aqueous solution of sodium hydroxide (20 ml) and di-tert-butyl dicarbonate (5.05 ml), then the mixture was stirred for 16 hours at room temperature. The reaction mixture was concentrated, then the pH was adjusted to 3.0, followed by extraction with ethyl acetate (100 ml×2). The ethyl acetate layer was washed with water and a saturated saline, dried over anhydrous sodium sulfate, and then concentrated. The concentrate was subjected to a silica-gel column chromatography for elution with a chloroform eluent supplemented with sequentially added methanol and acetic acid. The fraction eluted with 5% methanol (containing 1% acetic acid) was concentrated. Acetic acid was azeotropically distilled with toluene to give N-Boc-3-(3,4-dihydroxyphenyl)-L-alanine (5.41 g) as a white powder (yield 91%). A portion (3.00 g) of this product was, in substantially the same manner as in Example 5, condensed with morpholine (883μl) to give N-[Boc-3-(3,4-dihydroxyphenyl)-L-alanyl]morpholine (3.10 g) as a white powder (yield 84%). After Boc group elimination with 4N HCl/ethyl acetate (manufactured by Kokusan Kagaku Co., Ltd.), the product was condensed with (2S,3S)-ethyl hydrogen trans-epoxysuccinate (423 mg) as obtained in Reference Example 8 to yield the title compound (compound 61; 626 mg) as a white powder (yield 58%).

$[\alpha]_D$ +46° (c 0.55, $CHCl_3$, 26° C.)

Elemental analysis for $C_{19}H_{24}N_2O_8$: Calcd.: C, 55.88; H, 5.92; N, 6.86 Found: C, 55.62; H, 6.06; N, 6.59

$^1H$ NMR δ ppm ($CDCl_3$) 1.30 (3H, t, J=7.2 Hz), 2.85 (2H, d, J=7.2 Hz), 3.11 (2H, m), 3.36 (1H, m), 3.48 (1H, d, J=1.8 Hz), 3.52 (3H, m), 3.61 (2H, m), 3.71 (1H, d, J=1.8 Hz), 4.25 (2H, m), 5.07 (1H, dt, J=8.0, 7.4 Hz), 6.55 (1H, dd, J=2.0, 8.1 Hz), 6.70 (1H, d, J=1.9 Hz), 6.79 (1H, d, J=8.0 Hz), 7.33 (1H, d, J=8.2 Hz)

EXAMPLE 64

N-{N-[(2S,3S)-3-trans-carboxyoxirane-2-carbonyl]-3-(3,4-dihydroxypheny-L-alanyl}morpholine monosodium salt In substantially the same manner as in Example 27, compound 61 (100 mg) was subjected to alkali hydrolysis of ethyl ester. The pH of the solution was adjusted to 7, then the solution was concentrated, and then lyophilized. The lyophilizate was subjected to a preparative HPLC (column, YMC Pack D-ODS-5; mobile phase, 7%(v/v) acetonitrile/0.01M phosphate buffer solution pH 6.3; flow rate, 10 ml/min.; detection, 214 nm). Fractions showing major peak were collected and concentrated. The concentrate was subjected to a column chromatography with HP-20 (10 ml), and the column was washed with water (20 ml). Elution was then carried out with water (20 ml). The eluate was concentrated, and then lyophilized to yield the title compound (compound 62; 26.0 mg) as a white powder (yield 26%).

$^1H$ NMR δ ppm ($D_2O$) 2.83 (1H, m), 2.84 (1H, dd, J=9.7, 13.2 Hz), 2.99 (1H, dd, J=6.2, 13.1 Hz), 3.26 (1H, m), 3.37 (1H, d, J=2.0 Hz), 3.40 (3H, m), 3.53 (1H, d, J=2.1 Hz), 3.63 (4H, m), 4.98 (1H, dd, J=6.2, 9.7 Hz), 6.68 (1H, dd, J=2.1, 8.1 Hz), 6.76 (1H, d, J=2.0 Hz), 6.87 (1H, d, J=8.1 Hz)

EXAMPLE 65

N-{N-[(2S,3S)-3-trans-ethoxycarbonyloxirane-2-carbonyl]-L-phenylglycyl}morpholine In substantially the same manner as in Example 5, morpholine (1.04 ml) was condensed with Boc-L-phenylglycine (3.00 g, manufactured by Kokusan Kagaku Co., Ltd.) to give N-(Boc-L-phenylglycyl)morpholine (3.36 g) as a white powder (yield 88%). After Boc group elimination with TFA, the product was condensed with (2S,3S)-ethyl hydrogen trans-epoxysuccinate as obtained in Reference Example 8 (486 g) to yield the title compound (compound 63; 940 mg) as a white powder (yield 85%).

$[\alpha]_D$+171° (c 0.62, $CHCl_3$, 25° C.)

Elemental analysis for $C_{18}H_{22}N_2O_6 \cdot 0.2H_2O$: Calcd.: C, 59.07; H, 6.17; N, 7.65 Found: C, 59.11; H, 6.02; N, 7.21

$^1H$ NMR δ ppm ($CDCl_3$) 1.28 (3H, t, J=7.1 Hz), 3.10 (1H, ddd, J=3.0, 7.1, 11.4 Hz), 3.23 (1H, ddd, J=2.9, 5.9, 13.3 Hz), 3.35 (1H, d, J=1.8 Hz), 3.41 (1H, ddd, J=3.0, 7.1, 13.3 Hz), 3.52 (1H, ddd, J=3.0, 6.0, 11.4 Hz), 3.57 (2H, m), 3.66 (1H, d, J=1.8 Hz), 3.72 (2H, m), 4.22 (2H, m), 5.78 (1H, d, J=7.3 Hz), 7.36 (5H, m), 7.63 (1H, d, J=7.2 Hz)

EXAMPLE 66

N-{N-[(2S,3S)-3-trans-carboxyoxirane-2-carbonyl]-L-phenylglycyl}morpholine monosodium salt In substantially the same manner as in Example 27, compound 63 (250 mg) was subjected to alkali hydrolysis of ethyl ester, which was desalinized with resin, followed by concentration. The concentrate was lyophilized to yield the title compound (compound 64; 222 mg) as a white powder (yield 90%).

$[\alpha]_D$+144° (c 0.59, $H_2O$, 25° C.)

Elemental analysis for $C_{16}H_{17}N_2O_6Na \cdot 0.5H_2O$: Calcd.: C, 52.61; H, 4.97; N, 7.67; Na, 6.29 Found: C, 52.68; H, 5.21; N, 7.93; Na, 6.31

$^1H$ NMR δ ppm ($D_2O$) 3.19 (1H, m), 3.39 (1H, m), 3.43 (1H, d, J=2.1 Hz), 3.58 (1H, d, J=2.0 Hz), 3.60 (4H, m), 3.74 (2H, m), 5.90 (1H, s), 7.44 (5H, m)

EXAMPLE 67

N-{N-[(2S,3S)-3-trans-ethoxycarbonyloxirane-2-carbonyl}-L-homophenylalanyl}morpholine In substantially the same manner as in Example 5, morpholine (280 μl) was condensed with Boc-L-homophenylalanine (900 mg, manufactured by Bachem Fein Chemikalien AG, Switzerland) to give N-(BOC-L-homophenylalanyl-)morpholine (1.06 g) as a white powder (yield 95%). After Boc group elimination with 4N HCl/ethyl acetate, the product was condensed with (2S,3S)-ethyl hydrogen trans-epoxysuccinate (338 mg) as obtained in Reference Example 8 to yield the title compound (compound 65; 630 mg) as a white powder (yield 77%).

$[\alpha]_D$+53° (c 0.75, CHCl$_3$, 26° C.)

Elemental analysis for $C_{20}H_{26}N_2O_6$: Calcd.: C, 61.53; H, 6.71; N, 7.17 Found: C, 61.28; H, 6.84; N, 7.02

$^1$H NMR δ ppm (CDCl$_3$) 1.33 (3H, t, J=7.2 Hz), 1.92 (1H, dt, J=14.2, 7.4 Hz), 2.04 (1H, ddd, J=4.3, 7.8, 14.2 Hz), 2.62 (2H, dt, J=1.5, 7.6 Hz), 3.22 (1H, ddd, J=3.8, 6.0, 13.5 Hz), 3.34 (1H, ddd, J=3.9, 5.7, 12.6 Hz), 3.59 (6H, m), 3.66 (1H, d, J=1.9 Hz), 4.27 (2H, m), 4.91 (1H, dt, J=4.3, 8.0 Hz), 7.01 (1H, d, J=8.1 Hz), 7.25 (5H, m)

EXAMPLE 68

N-{N-[(2S,3S)-3-trans-carboxyoxirane-2-carbonyl]-L-homophenylalanyl}morpholine monosodium salt In substantially the same manner as in Example 27, compound 65 (100 mg) was subjected to alkali hydrolysis of ethyl ester, which was desalinized with resin, followed by concentration and lyophilization to yield the title compound (compound 66; 94.9 mg) as a white powder (yield 96%).

$[\alpha]_D$+35° (c 0.56, H$_2$O, 26° C.)

Elemental analysis for $C_{18}H_{21}N_2O_6Na·1.2H_2O$: Calcd.: C, 53.25; H, 5.81; N, 6.90; Na, 5.66 Found: C, 53.25; H, 5.82; N, 7.08; Na, 5.86

$^1$H NMR δ ppm (D$_2$O) 2.04 (2H, m), 2.65 (1H, dt, J=14.4, 7.3 Hz), 2.80 (1H, dt, J=14.2, 6.7 Hz), 3.27 (1H, dt, J=13.9, 5.0 Hz), 3.37 (1H, dt, J=13.5, 4.7 Hz), 3.40 (1H, d, J=2.0 Hz), 3.52 (2H, m), 3.55 (1H, d, J=2.0 Hz), 3.63 (2H, t, J=4.8 Hz), 3.68 (2H, t, J=4.9 Hz), 4.65 (1H, dd, J=5.0, 8.7 Hz), 7.33 (5H, m)

EXAMPLE 69

N-{N-[(2S,3S)-3-trans-ethoxycarbonyloxirane-2-carbonyl]-p-chloro-L-phenylalanyl}morpholine In substantially the same manner as in Example 5, morpholine (257 µl) was condensed with Boc-p-chloro-L-phenylalanine (800 mg, manufactured by Bachem Fein Chemikalien AG, Switzerland) to give N-(Boc-p-chloro-L-phenylalanyl)morpholine (913 mg) as a colorless oily product (yield 93%). After Boc group elimination with 4N HCl/ethyl acetate, the product was condensed with (2S,3S)-ethyl hydrogen trans-epoxysuccinate (238 mg) as obtained in Reference Example 8 to yield the title compound (compound 67; mg) as a white powder (yield 58%).

$[\alpha]_D$+43° (c 0.51, CHCl$_3$, 24° C.)

Elemental analysis for $C_{19}H_{23}N_2O_6Cl·0.5H_2O$: Calcd.: C, 54.35; H, 5.76; N, 6.67; Cl, 8.44 Found: C, 54.51; H, 5.59; N, 6.78; Cl, 8.59

$^1$H NMR δ ppm (CDCl$_3$) 1.32 (3H, t, J=7.1 Hz), 2.92 (1H, dd, J=6.1, 13.3 Hz), 2.99 (1H, dd, J=6.1, 13.3 Hz), 3.08 (1H, ddd, J=3.0, 6.7, 13.1 Hz), 3.20 (1H, ddd, J=3.0, 6.4, 11.5 Hz), 3.31 (1H, d, J=1.9 Hz), 3.39 (1H, ddd, J=3.0, 6.4, 13.1 Hz), 3.57 (5H, m), 3.63 (1H, d, J=1.9 Hz), 4.26 (2H, m), 5.09 (1H, dt, J=6.2, 8.2 Hz), 6.96 (1H, br d, J=8.2 Hz), 7.10 (2H, d, J=8.4 Hz), 7.29 (2H, d, J=8.4 Hz)

EXAMPLE 70

N-{N-[(2S,3S)-trans-carboxyoxirane-2-carbonyl]-p-chloro-L-phenylalanyl}morpholine monosodium salt In substantially the same manner as in Example 27, compound 67 (100 mg) was subjected to alkali hydrolysis of ethyl ester, which was desalinized with resin. The resultant was concentrated and lyophilized to yield the title compound (compound 68; 92 mg) as a white powder (yield 93%).

$[\alpha]_D$+66° (c 0.47, H$_2$O, 24° C.)

Elemental analysis for $C_{17}H_{18}N_2O_6ClNa·1.5H_2O$: Calcd.: C, 47.29; H, 4.90; N, 6.49; Cl, 8.21; Na, 5.32 Found: C, 47.51; H, 5.07; N, 6.24; Cl, 7.86; Na, 5.41

$^1$H NMR δ ppm (D$_2$O) 3.06 (3H, m), 3.24 (1H, ddd, J=2.8, 6.0, 13.6 Hz), 3.36 (1H, d, J=2.0 Hz), 3.52 (4H, m), 3.54 (1H, d, J=2.0 Hz), 3.65 (2H, m), 5.07 (1H, dd, J=7.2, 8.4 Hz), 7.25 (2H, d, J=8.4 Hz), 7.42 (2H, d, J=8.4 Hz)

EXAMPLE 71

N-{N-[(2S,3S)-3-trans-ethoxycarbonyloxirane-2-carbonyl]-p-fluoro-L-phenylalanyl}morpholine In substantially the same manner as in Example 5, morpholine (278 µl) was condensed with Boc-p-fluoro-L-phenylalanine (900 mg, manufactured by Bachera Fein Chemikalien AG, Switzerland) to give N-(Boc-p-fluoro-L-phenylalanyl)morpholine (1.02 g) as a white powder (yield 91%). After Boc group elimination with 4N HCl/ethyl acetate, the product was condensed with (2S,3S)-ethyl hydrogen trans-epoxysuccinate as obtained in Reference Example 8 (333 mg) to yield the title compound (compound 69; 520 mg) as a white powder (yield 63%).

$[\alpha]_D$+43° (c 0.62, CHCl$_3$, 25° C.)

Elemental analysis for $C_{19}H_{23}N_2O_6F·0.25H_2O$: Calcd.: C, 57.21; H, 5.94; N, 7.02 Found: C, 57.23; H, 5.92; N, 6.82

$^1$H NMR δ ppm (CDCl$_3$) 1.32 (3H, t, J=7.2 Hz), 2.92 (1H, dd, J=6.1, 13.3 Hz), 2.99 (1H, dd, J=8.2, 13.4 Hz), 3.05 (1H, ddd, J=3.0, 6.7, 13.3 Hz), 3.17 (1H, ddd, J=3.0, 6.5, 11.5 Hz), 3.32 (1H, d, J=1.9 Hz), 3.37 (1H, ddd, J=2.9, 6.5, 13.3 Hz), 3.51 (1H, m), 3.57 (4H, m), 3.63 (1H, d, J=1.9 Hz), 4.27 (2H, m), 5.08 (1H, dt, J=6.3, 8.2 Hz), 6.90 (1H, d, J=7.6 Hz), 7.01 (2H, m), 7.13 (2H, m)

EXAMPLE 72

N-{N-[(2S,3S)-3-trans-carboxyoxirane-2-carbonyl]-p-fluoro-L-phenylalanyl}morpholine monosodium salt In substantially the same manner as in Example 27, the compound 69 (100 mg) was subjected to alkali hydrolysis of ethyl ester, which was desalinized with resin, followed by concentration and lyophilization to yield the title compound (compound 70; 95.6 mg) as a white powder (yield 97%).

$[\alpha]_D$+67° (c 0.56, H$_2$O, 26° C.)

Elemental analysis for $C_{17}H_{18}N_2O_6FNa·0.5H_2O$: Calcd.: C, 51.39; H, 4.82; N, 7.05; F, 4.78; Na, 5.79 Found: C, 51.31; H, 4.99; N, 7.20; F, 4.82; Na, 5.82

$^1$H NMR δ ppm (D$_2$O) 3.00 (1H, dd, J=8.5, 13.3 Hz), 3.06 (1H, dd, J=7.0, 13.6 Hz), 3.10 (1H, ddd, J=2.9, 7.1, 11.8 Hz), 3.26 (1H, ddd, J=3.0, 6.3, 13.8 Hz), 3.34 (1H, d, J=2.1 Hz), 3.50 (4H, m), 3.52 (1H, d, J=2.1 Hz), 3.60 (1H, ddd, J=3.2,

EXAMPLE 73

N-{N-[(2S,3S)-3-trans-ethoxycarbonyloxirane-2-carbonyl]-p-nitro-L-phenylalanyl}morpholine In substantially the same manner as in Example 5, morpholine (290 μl) was condensed with Boc-p-nitro-L-phenylalanine (996 mg, Bachem Fein Chemikalien AG, Switzerland) to give N-(Boc-p-nitro-L-phenylalanyl)morpholine (1.22 g) as a white powder (yield 96%). After Boc group elimination with 4N HCl/ethyl acetate, the product was condensed with (2S,3S)-ethyl hydrogen trans-epoxysuccinate as obtained in Reference Example 8 (465 mg) to yield the title compound (compound 71; 878 mg) as a white powder (yield 81%).

$[\alpha]_D$+33° (c 0.59, CHCl$_3$, 26° C.)

Elemental analysis for C$_{19}$H$_{23}$N$_3$O$_8$: Calcd.: C, 54.15; H, 5.50; N, 9.97 Found: C, 54.22; H, 5.51; N, 9.96

$^1$H NMR δ ppm (CDCl$_3$) 1.32 (3H, t, J=7.0 Hz), 3.03 (1H, dd, J=6.5, 13.5 Hz), 3.12–3.27 (1H, m), 3.18 (1H, dd, J=8.5, 13.5 Hz), 3.26 (1H, d, J=2.0 Hz), 3.35 (1H, ddd, J=2.5, 6.0, 11.0 Hz), 3.42–3.75 (6H, m), 3.63 (1H, d, J=2.0 Hz), 4.17–4.35 (2H, m), 5.17 (1H, ddd, J=6.5, 8.0, 8.0 Hz), 6.97 (1H, d, J=8.0 Hz), 7.35 (2H, d, J=9.0 Hz), 8.20 (2H, d, J=9.0 Hz)

EXAMPLE 74

N-{N-[(2S,3S)-3-trans-carboxyoxirane-2-carbonyl]-p-nitro-L-phenylalanyl}morpholine mosodium salt In substantially the same manner as in Example 27, compound 71 (260 mg) was subjected to alkali hydrolysis of ethyl ester, which was desalinized with resin, followed by condensation and lyophilization to yield the title compound (compound 72; 250 mg) (yield 98%).

$[\alpha]_D$+54° (c 0.51, H$_2$O, 26° C.)

Elemental analysis for C$_{17}$H$_{18}$N$_3$O$_8$Na·1.5H$_2$O: Calcd.: C, 46.16; H, 4.78; N, 9.50 Found: C, 46.15; H, 4.57; N, 9.78

$^1$H NMR δ ppm (D$_2$O) 3.20 (2H, d, J=7.5 Hz), 3.21–3.41 (2H, m), 3.33 (1H, d, J=2.0 Hz), 3.43–3.76 (6H, m), 3.53 (1H, d, J=2.0 Hz), 5.17 (1H, t, J=7.5 Hz), 7.50 (2H, d, J=9.0 Hz), 8.24 (2H, d, J=9.0 Hz)

EXAMPLE 75

N-{N-[(2S,3S)-3-trans-ethoxycarbonyloxirane-2-carbonyl]-3-(2-thienyl)morpholine

In substantially the same manner as in Example 5, morpholine (319 μl) was condensed with Boc-3-(2-thienyl)-L-alanine (900 mg, manufactured by Bachem Fein Chemikalien AG, Switzerland) to give N-[Boc-3-(2-thienyl)-L-alanyl]morpholine (1.13 g) as a colorless oily product (yield quantitative). After Boc group elimination with 4N HCl/ethyl acetate, the product was condensed with (2S,3S)-ethyl hydrogen trans-epoxysuccinate as obtained in Reference Example 8 (315 mg) to yield the title compound (compound 73; 563 mg) as a white powder (yield 75%).

$[\alpha]_D$+47° (c 0.53, CHCl$_3$, 24° C.)

Elemental analysis for C$_{17}$H$_{22}$N$_2$O$_6$S: Calcd.: C, 53.39; H, 5.80; N, 7.32; S, 8.38 Found: C, 53.04; H, 5.69; N, 7.41; S, 8.41

$^1$H NMR δ ppm (CDCl$_3$) 1.32 (3H, t, J=7.1 Hz), 3.17 (1H, dd, J=5.9, 14.6 Hz), 3.26 (1H, dd, J=7.5, 14.6 Hz), 3.30 (2H, m), 3.44 (1H, d, J=1.8 Hz), 3.47 (1H, m), 3.54–3.70 (5H, m), 3.66 (1H, d, J=1.8 Hz), 4.26 (2H, m), 5.11 (1H, ddd, J=5.9, 7.5, 8.0 Hz), 6.83 (1H, dd, J=1.2, 3.4 Hz), 6.96 (1H, dd, J=3.4, 5.2 Hz), 7.04 (1H, br d, J=8.0 Hz), 7.20 (1H, dd, J=1.2, 5.1 Hz)

EXAMPLE 76

N-{N-[(2S,3S)-3-trans-carboxyoxirane-2-carbonyl]-3-(2-thienyl)-L-alanyl}morpholine monosodium salt In substantially the same manner as in Example 27, compound 73 (114 mg) was subjected to alkali hydrolysis of ethyl ester, which was desalinized with resin, followed by concentration and lyophilization to yield the title compound (compound 74; 98 mg) as a white powder (yield 85%).

$[\alpha]_D$+57° (c 0.50, H$_2$O, 25° C.)

Elemental analysis for C$_{15}$H$_{17}$N$_2$O$_6$SNa·0.5H$_2$O: Calcd.: C, 46.75; H, 4.71; N, 7.27; S, 8.32; Na, 5.97 Found: C, 46.60; H, 4.89; N, 7.32; S, 8.48; Na, 5.83

$^1$H NMR δ ppm (D$_2$O) 3.31 (2H, d, J=7.4 Hz), 3.33 (1H, m), 3.40 (1H, d, J=2.0 Hz), 3.44–3.78 (7H, m), 3.55 (1H, d, J=2.0 Hz), 5.10 (1H, t, J=7.4 Hz), 6.98 (1H, dd, J=1.2, 3.4 Hz), 7.05 (1H, dd, J=3.4, 5.2 Hz), 7.36 (1H, dd, J=1.2, 5.2 Hz)

EXAMPLE 77

N-{N-[(2S,3S)-3-trans-ethoxycarbonyloxirane-2-carbonyl}-3-cyclohexyl-L-alanyl}morpholine In substantially the same manner as in Example 5, morpholine (210 μl) was condensed with Boc-3-cyclohexyl-L-alanine (590 mg, manufactured by Bachera Fein Chemikalien AG, Switzerland) to give N-(Boc-3-cyclohexyl-L-alanyl)morpholine (702 mg) as a colorless oily product (yield 95%). After Boc group elimination with 4N HCl/ethyl acetate, the product was condensed with (2S,3S)-ethyl hydrogen trans-epoxysuccinate as obtained in Reference Example 8 (210 mg) to yield the title compound (compound 75; 379 mg) as a colorless oily product (yield 76%).

$[\alpha]_D$+42° (c 0.57, CHCl$_3$, 25° C.)

Elemental analysis for C$_{19}$H$_{30}$N$_2$O$_6$·0.5H$_2$O: Calcd.: C, 58.30; H, 7.98; N, 7.16 Found: C, 58.70; H, 7.90; N, 6.52

$^1$H NMR δ ppm (CDCl$_3$) 0.96 (2H, m), 1.27 (4H, m), 1.40 (3H, t, J=7.1 Hz), 1.55 (2H, m), 1.72 (4H, m), 1.99 (1H, br d, J=12.1 Hz), 3.56 (1H, d, J=1.9 Hz), 3.61 (2H, m), 3.75 (1H, d, J=1.9 Hz), 3.76 (6H, m), 4.35 (2H, m), 5.05 (1H, dt, J=8.6, 7.1 Hz), 7.00 (1H, br d, J=8.6 Hz)

EXAMPLE 78

N-{N-[(2S,3S)-3-trans-carboxyoxirane-2-carbonyl]-3-cyclohexyl-L-alanyl}morpholine monosodium salt In substantially the same manner as in Example 27, compound 75 (100 mg) was subjected to alkali hydrolysis of ethyl ester, which was desalinized with resin, followed by concentration and lyophilization to yield the title compound (compound 76; 90 mg) as a white powder (yield 91%).

$[\alpha]_D$+48° (c 0.49, H$_2$O, 25° C.)

Elemental analysis for C$_{17}$H$_{25}$N$_2$O$_6$Na·H$_2$O: Calcd.: C, 51.77; H, 6.90; N, 7.10; Na, 5.83 Found: C, 51.76; H, 7.16; N, 7.18; Na, 5.97

$^1$H NMR δ ppm (D$_2$O) 0.96 (2H, m), 1.20 (4H, m), 1.66 (7H, m), 3.44 (1H, d, J=2.0 Hz), 3.58 (1H, d, J=2.0 Hz), 3.67 (8H, m), 4.90 (1H, dd, J=4.7, 10.0 Hz)

EXAMPLE 79

N-{N-[(2S,3S)-3-trans-ethoxycarbonyloxirane-2-carbonyl]-p-methoxy-L-phenylalanyl}morpholine The compound 59 (392 mg) was dissolved in DMF (10 ml), to which were added potassium carbonate (76 mg) and methyl iodide (69 μl), followed by stirring for 14 hours. To the reaction mixture was added methyl iodide (280 μl), followed by stirring for 20 hours. The reaction mixture was concentrated, to which was added a 10% aqueous solution of ammonium chloride, followed by extraction with ethyl acetate. The ethyl acetate layer was washed with water and a saturated saline, dried over anhydrous sodium sulfate, which was subjected to a silica-gel column chromatography (50 ml) for elution with 1%(v/v) methanol/chloroform. The eluate was concentrated to yield the title compound (compound 77; 107 mg) as a colorless oily product (yield 26%).

$^1$H NMR δ ppm (CDCl$_3$) 1.32 (3H, t, J=7.2 Hz), 2.92 (2H, d, J=7.3 Hz), 3.03 (1H, ddd, J=3.0, 6.5, 13.2 Hz), 3.12 (1H, ddd, J=3.0, 6.5, 11.4 Hz), 3.34 (1H, d, J=1.9 Hz), 3.35 (1H, ddd, J=3.1, 6.5, 13.2 Hz), 3.44 (1H, ddd, J=3.0, 6.5, 11.4 Hz), 3.58 (4H, m), 3.63 (1H, d, J=1.9 Hz), 3.80 (3H, s), 4.26 (2H, m), 5.06 (1H, dt, J=8.0, 7.4 Hz), 6.84 (2H, d, J=8.7 Hz), 6.92 (1H, d, J=8.1 Hz), 7.07 (2H, d, J=8.7 Hz)

EXAMPLE 80

N-{N-[(2S,3S)-3-trans-carboxyoxirane-2-carbonyl]-p-methoxy-L-phenylalanyl}morpholine monosodium salt In substantially the same manner as in Example 27, compound 77 (105 mg) was subjected to alkali hydrolysis of ethyl ester, which was desalinized with resin, followed by concentration and lyophilization to yield the title compound (compound 78; 93 mg) as a white powder (yield 90%).

[α]$_D$+70° (c 0.51, H$_2$O, 25° C.)

Elemental analysis for C$_{18}$H$_{21}$N$_2$O$_7$Na·0.5H$_2$O: Calcd.: C, 52.81; H, 5.42; N, 6.84 Found: C, 52.72; H, 5.66; N, 7.01

$^1$H NMR δ ppm (D$_2$O) 2.96 (2H, m), 3.04 (1H, dd, J=6.5, 13.3 Hz), 3.23 (1H, m), 3.35 (1H, d, J=2.0 Hz), 3.44 (3H, m), 3.52 (1H, d, J=2.0 Hz), 3.56 (2H, m), 3.65 (1H, m), 3.82 (3H, s), 5.01 (1H, dd, J=6.9, 9.0 Hz), 6.98 (2H, d, J=8.6 Hz), 7.21 (2H, d, J=8.6 Hz)

EXAMPLE 81

N-{N-[(2S,3S)-3-trans-ethoxycarbonyloxirane-2-carbonyl]-3-(1-naphthyl)-L-alanyl}morpholine In substantially the same manner as in Example 5, morpholine (275 μl) was condensed with Boc-3-(1-naphthyl)-L-alanine (970 mg, manufactured by Bachem Fein Chemikalien AG, Switzerland) to give N-[Boc-3-(1-naphthyl)-L-alanyl]morpholine (1.18 g) as a white powder (yield quantitative). After Boc group elimination with TFA, the product was condensed with (2S,3S)-ethyl hydrogen trans-epoxysuccinate (620 mg) as obtained in Reference Example 8 to yield the title compound (compound 79; 1.09 g) as a white powder (yield 75%).

[α]$_D$+48° (c 0.60, CHCl$_3$, 26° C.)

Elemental analysis for C$_{23}$H$_{26}$N$_2$O$_6$: Calcd.: C, 64.78; H, 6.14; N, 6.57 Found: C, 64.88; H, 6.25; N, 6.64

$^1$H NMR δ ppm (CDCl$_3$) 1.33 (3H, t, J=7.0 Hz), 2.09 (1H, ddd, J=3.0, 8.0, 11.5 Hz), 2.28 (1H, ddd, J=3.0, 5.5, 13.0 Hz), 2.84 (1H, ddd, J=3.0, 8.0, 13.0 Hz), 2.99 (1H, ddd, J=3.0, 5.5, 11.5 Hz), 3.02–3.13 (1H, m), 3.21–3.35 (1H, m), 3.27 (1H, dd, J=10.5, 13.0 Hz), 3.41–3.54 (2H, m), 3.47 (1H, d, J=2.0 Hz), 3.65 (1H, dd, J=5.0, 13.0 Hz), 3.69 (1H, d, J=2.0 Hz), 4.19–4.37 (2H, m), 5.31 (1H, ddd, J=5.0, 7.5, 10.5 Hz), 7.18 (1H, d, J=7.5 Hz), 7.33 (1H, dd, J=1.0, 7.5 Hz), 7.41 (1H, t, J=7.5 Hz), 7.52 (1H, ddd, J=1.0, 7.0, 8.0 Hz), 7.61 (1H, ddd, J=1.5, 7.0, 8.5 Hz), 7.81 (1H, d, J=8.0 Hz), 7.87 (1H, dd, J=1.0, 8.0 Hz), 8.24 (1H, d, J=8.5 Hz)

EXAMPLE 82

N-{N-[(2S,3S)-3-trans-carboxyoxirane-2-carbonyl]-3-(1-naphthyl)-L-alanyl}morpholine monosodium salt In substantially the same manner as in Example 27, compound 79 (332 mg) was subjected to alkali hydrolysis of ethyl ester, which was desalinized with resin, followed by concentration and lyophilization to yield the title compound (compound 80, 309 mg) (yield 94%).

[α]$_D$+94° (c 0.59, H$_2$O, 26° C.)

Elemental analysis for C$_{21}$H$_{21}$N$_2$O$_6$Na·1.5H$_2$O: Calcd.: C, 56.37; H, 5.41; N, 6.26 Found: C, 56.40; H, 5.28; N, 6.51

$^1$H NMR δ ppm (D$_2$O) 1.99 (1H, ddd, J=3.0, 8.5, 11.5 Hz), 2.56–2.71 (1H, m), 2.85 (1H, ddd, J=3.0, 8.5, 11.5 Hz), 2.94–3.23 (3H, m), 3.31–3.66 (4H, m), 3.41 (1H, d, J=2.0 Hz), 3.59 (1H, d, J=2.0 Hz), 5.18 (1H, dd, J=5.5, 10.5 Hz), 7.38 (1H, d, J=7.0 Hz), 7.50 (1H, t, J=7.5 Hz), 7.54–7.69 (2H, m), 7.90 (1H, d, J=8.0 Hz), 7.98 (1H, dd, J=2.0, 7.5 Hz), 8.08 (1H, d, J=8.0 Hz)

EXAMPLE 83

N-{N-[(2S,3S)-3-trans-ethoxycarbonyloxirane-2-carbonyl]-3-(2-naphthyl)-L-alanyl}morpholine In substantially the same manner as in Example 5, morpholine (275 μl) was condensed with Boc-3-(2-naphthyl)-L-alanine (900 mg, manufactured by Bachem Fein Chemikalien AG, Switzerland) to give N-[Boc-3-(2-naphthyl)-L-alanyl]morpholine (1.10 g) as a white powder (yield quantitative). After Boc group elimination with trifluoroacetic acid, the product was condensed with (2S,3S)-ethyl hydrogen trans-epoxysuccinate as obtained in Reference Example 8 (312 mg) to yield the title compound (compound 81; 695 mg) as a white powder (yield 84%).

[α]$_D$+47° (c 0.53, CHCl$_3$, 24° C.)

Elemental analysis for C$_{23}$H$_{26}$N$_2$O$_6$·0.5H$_2$O: Calcd.: C, 63.44; H, 6.25; N, 6.43 Found: C, 63.90; H, 6.16; N, 6.27

$^1$H NMR δ ppm (CDCl$_3$) 1.29 (3H, t, J=7.1 Hz), 2.83 (1H, ddd, J=3.0, 6.7, 11.3 Hz), 2.95 (1H, ddd, J=3.0, 6.9, 13.9 Hz), 3.14 (2H, br d, J=7.6 Hz), 3.32 (1H, d, J=1.9 Hz), 3.35 (3H, m), 3.56 (3H, m), 3.64 (1H, d, J=1.9 Hz), 4.23 (2H, m), 5.19 (1H, dt, J=6.9, 8.2 Hz), 7.04 (1H, br d, J=8.2 Hz), 7.29 (1H, dd, J=1.7, 8.4 Hz), 7.48 (2H, m), 7.61 (1H, br s), 7.80 (3H, m)

EXAMPLE 84

N-{N-[(2S,3S)-3-trans-carboxyoxirane-2-carbonyl]-3-(2-naphthyl)-L-alanyl}morpholine monosodium salt In substantially the same manner as in Example 27, compound 81 (100 mg) was subjected to alkali hydrolysis of ethyl ester, which was desalinized with resin, followed by concentration and lyophilization to yield the title compound (compound 82; 96 mg) as a white powder (yield 97%).

$[\alpha]_D$+78° (c 0.47, H2O, 24° C.)

Elemental analysis for $C_{21}H_{21}N_2O_6Na·1.5H_2O$: Calcd.: C, 56.37; H, 5.41; N, 6.26; Na, 5.14 Found: C, 56.22; H, 5.59; N, 6.07; Na, 5.17

$^1$H NMR δ ppm (D$_2$O) 2.55 (1H, m), 3.15 (4H, m), 3.35 (3H, m), 3.38 (1H, d, J=2.0 Hz), 3.52 (2H, m), 3.55 (1H, d, J=2.0 Hz), 5.08 (1H, dd, J=6.7, 9.2 Hz), 7.39 (1H, dd, J=1.5, 8.5 Hz), 7.57 (2H, m), 7.72 (1H, br s), 7.92 (3H, m)

EXAMPLE 85

N-{N-[(2S,3S)-3-trans-ethoxycarbonyloxirane-2-carbonyl]-L-phenylalanyl}thiomorpholine In substantially the same manner as in Example 20, N-[(2S,3S)-3-trans-ethoxycarbonyloxirane-2-carbonyl]-L-phenylalanine (1.00 g) was condensed with thiomorpholine (350μl, manufactured by Tokyo Kasei Co., Ltd.) to yield the title compound (compound 83; 1.00 g) as a white powder (yield 78%).

$[\alpha]_D$+53° (c 0.57, CHCl$_3$, 24° C.)

Elemental analysis for $C_{19}H_{24}N_2O_5S·0.5H_2O$: Calcd.: C, 56.84; H, 6.28; N, 6.98; S, 7.99 Found: C, 57.03; H, 5.99; N, 7.04; S, 8.44

$^1$H NMR δ ppm (CDCl$_3$) 1.31 (3H, t, J=7.0 Hz), 1.96 (1H, ddd, J=2.5, 7.5, 13.5 Hz), 2.36–2.65 (3H, m), 2.94 (1H, dd, J=6.0, 13.0 Hz), 3.02 (1H, dd, J=8.5, 13.0 Hz), 3.33 (1H, d, J=2.0 Hz), 3.43 (1H, ddd, J=2.5, 7.5, 14.0 Hz), 3.57 (1H, ddd, J=2.5, 7.5, 14.0 Hz), 3.63 (1H, d, J=2.0 Hz), 3.82 (2H, t, J=5.0 Hz), 4.16–4.34 (2H, m), 5.12 (1H, ddd, J=6.0, 8.5, 8.5 Hz), 7.01 (1H, d, J=8.5 Hz), 7.10–7.37 (5H, m)

EXAMPLE 86

N-{N-[(2S,3S)-3-trans-carboxyoxirane-2-carbonyl]-L-phenylalanyl}thiomorpholine monosodium salt In substantially the same manner as in Example 27, compound 83 (220 mg) was subjected to alkali hydrolysis of ethyl ester, which was desalinized with resin, followed by concentration and lyophilization to yield the title compound (compound 84; 133 mg) (yield 62%).

$[\alpha]_D$+580 (c 0.57, H2O, 24° C.)

Elemental analysis for $C_{17}H_{19}N_2O_5SNa·H_2O$: Calcd.: C, 50.49; H, 5.23; N, 6.93 Found: C, 50.70; H, 5.35; N, 7.00

$^1$H NMR δ ppm (D$_2$O) 1.90–2.03 (1H, m), 2.42–2.68 (3H, m), 3.07 (2H, d, J=7.5 Hz), 3.35 (1H, d, J=2.0 Hz), 3.53 (1H, d, J=2.0 Hz), 3.56–3.88 (4H, m), 5.09 (1H, t, J=7.5 Hz), 7.23–7.48 (5H, m)

EXAMPLE 87

N-Z-N'-{N-[(2S,3S)-3-trans-n-propylcarbamoyloxirane-2-carbonyl]-L-phenylalanyl}-1,4-diaminobutane The compound 6 (300 mg) was suspended in DMF (10 ml), to which were added, under ice-cooling conditions, n-propylamine (56 μl, manufacture by Wako Pure Chemical Industries, Ltd.), HOBT (92 mg) and WSC (131 mg), followed by stirring for 15 hours at room temperature. The reaction mixture was concentrated to dryness, to which was added ethyl acetate (150 ml). The mixture was washed with a 10% aqueous solution of citric acid, a 3% aqueous solution of sodium hydrogen carbonate and a saturated saline. The mixture was dried over anhydrous sodium sulfate, which was concentrated to dryness. To the concentrate was added ether, then resulting precipitate was recovered by filtration to yield the title compound (compound 85; 303 mg) (yield 93%).

$[\alpha]_D$+37° (c 0.63, DMF, 24° C.)

Elemental analysis for $C_{28}H_{36}N_4O_6·0.5H_2O$: Calcd.: C, 63.02; H, 6.99; N, 10.50 Found: C, 63.01; H, 6.99; N, 10.50

$^1$H NMR δ ppm (DMSO-d$_6$) 0.83 (3H, t, J=7.5 Hz), 1.34 (4H, m), 1.42 (2H, m), 2.79 (1H, dd, J=9.5, 13.5 Hz), 2.90–3.12 (7H, m), 3.37 (1H, d, J=1.5 Hz), 3.55 (1H, d, J=1.5 Hz), 4.49 (1H, m), 5.00 (2H, s), 7.14–7.40 (11H, m), 8.11 (1H, t, J=5.5 Hz), 8.31 (1H, t, J=5.5 Hz), 8.72 (1H, d, J=8.5 Hz)

EXAMPLE 88

N-{N-[(2S,3S)-3-trans-ethoxycarbonyloxirane-2-carbonyl]-L-phenylalanyl}-3-amino-1-propene In substantially the same manner as in Example 20, N-[(2S,3S)-3-trans-ethoxycarbonyloxirane-2-carbonyl]-L-phenylalanine (600 mg) was condensed with 3-amino-1-propene hydrochloride (201 mg, manufactured by Wako Pure Chemical Industries, Ltd.) to yield the title compound (compound 86; 481 mg) as a white powder (yield 71%).

$[\alpha]_D$+23° (c 0.51, CHCl$_3$, 25° C.)

Elemental analysis for $C_{18}H_{22}N_2O_5·0.1H_2O$: Calcd.: C, 62.09; H, 6.43; N, 8.05 Found: C, 62.01; H, 6.38; N, 8.07

$^1$H NMR δ ppm (CDCl$_3$) 1.30 (3H, t, J=7.2 Hz), 3.02 (1H, dd, J=7.7, 13.7 Hz), 3.09 (1H, dd, J=8.0, 13.8 Hz), 3.10 (1H, d, J=1.9 Hz), 3.62 (1H, d, J=1.9 Hz), 3.81 (2H, m), 4.24 (2H, m), 4.57 (1H, dt, J=8.0, 7.6 Hz), 5.08 (2H, m), 5.69 (1H, ddt, J=10.4, 17.0, 5.7 Hz), 5.78 (1H, t, J=4.7 Hz), 6.67 (1H, d, J=8.0 Hz), 7.18 (2H, m), 7.30 (3H, m)

EXAMPLE 89

N-(N-[(2S,3S)-3-trans-carboxyoxirane-2-carbonyl]-L-phenylalanyl}-3-amino-1-propene monosodium salt In substantially the same manner as in Example 27, the compound 86 (100 mg) was subjected to alkali hydrolysis of ethyl ester, which was desalinized with resin, followed by concentration and lyophization to yield the title compound (compound 87; 96 mg) (yield 98%).

$[\alpha]_D$+43° (c 0.52, H$_2$O, 25° C.)

Elemental analysis for $C_{16}H_{17}N_2O_5Na·1.5H_2O$: Calcd.: C, 52.32; H, 5.49; N, 7.63 Found: C, 52.38; H, 5.44; N, 7.81

$^1$H NMR δ ppm (D$_2$O) 3.01 (1H, dd, J=8.6, 13.8 Hz), 3.16 (1H, d, J=2.1 Hz), 3.18 (1H, dd, J=6.9, 13.8 Hz), 3.48 (1H, d, J=2.2 Hz), 3.73 (2H, dt, J=4.9, 1.6 Hz), 4.61 (1H, dd, J=7.0, 8.5 Hz), 5.02 (1H, dd, J=1.5, 17.2 Hz), 5.07 (1H, dd, J=1.5, 10.5 Hz), 5.73 (1H, ddt, J=10.3, 17.2, 5.1 Hz), 7.33 (5H, m)

EXAMPLE 90

N-{N-[(2S,3S)-3-trans-ethoxycarbonyloxirane-2-carbonyl]-L-tryptophanyl}-1-amino-3-methylbutane In substantially the same manner as in Example 5, 1-amino-3-methylbutane (405 μl) was condensed with Fmoc-Trp-OH (1.35 g, Peptide Institute, Inc.) to give N-(Fmoc-L-tryptophanyl)-1-amino-3-methylbutane (1.54 g) as a white powder (yield 98%). A portion (1.44 g) of this product was, in substantially the same manner as in Example 17, subjected to deprotection of Fmoc group, which was then condensed with (2S,3S)-ethyl hydrogen transepoxysuccinate as obtained in Reference Example 8 (432 mg) to yield the title compound (compound 88; 734 mg) as a white powder (yield 72%).

$[\alpha]_D$+31° (c 0.53, CHCl$_3$, 25° C.)

Elemental analysis for $C_{22}H_{29}N_3O_5 \cdot 0.15CHCl_3$: Calcd.: C, 61.38; H, 6.78; N, 9.70 Found: C, 61.55; H, 6.88; N, 9.78

$^1$H NMR δ ppm (CDCl$_3$) 0.81 (3H, d, J=6.6 Hz), 0.81 (3H, d, J=6.6 Hz), 1.13 (2H, q, J=7.3 Hz), 1.30 (3H, t, J=7.2 Hz), 1.37 (1H, m), 3.12 (3H, m), 3.16 (1H, d, J=1.9 Hz), 3.25 (1H, ddd, J=0.6, 6.0, 14.4 Hz), 3.62 (1H, d, J=1.9 Hz), 4.23 (2H, m), 4.63 (1H, dt, J=6.0, 8.1 Hz), 5.50 (1H, t, J=5.6 Hz), 6.86 (1H, d, J=7.7 Hz), 7.04 (1H, d, J=2.4 Hz), 7.16 (1H, ddd, J=1.1, 7.1, 7.8 Hz), 7.23 (1H, ddd, J=1.3, 7.1, 8.1 Hz), 7.38 (1H, dd, J=1.1, 7.8 Hz), 7.67 (1H, dd, J=0.9, 7.8 Hz), 8.18 (1H, br s)

EXAMPLE 91

N-{N-[(2S,3S)-3-trans-carboxyoxirane-2-carbonyl]-L-tryptophanyl}-1-amino-3-methylbutane monosodium salt In substantially the same manner as in Example 27, the compound 88 (200 mg) was subjected to alkali hydrolysis of ethyl ester, which was desalinized with resin, followed by concentration and lyophilization to yield the title compound (compound 89; 181 mg) (yield 92%).

$[\alpha]_D$+59° (c 0.56, H20, 25° C.)

Elemental analysis for $C_{20}H_{24}N_3O_5Na \cdot 1.5H_2O$: Calcd.: C, 55.04; H, 6.24; N, 9.63; Na; 5.27 Found: C, 55.15; H, 6.34; N, 9.71; Na; 5.37

$^1$H NMR δ ppm (D$_2$O) 0.71 (6H, d, J=6.2 Hz), 1.01 (2H, m), 1.10 (1H, m), 2.91 (1H, dt, J=13.5, 6.8 Hz), 3.09 (1H, dt, J=13.7, 6.9 Hz), 3.23 (2H, d, J=7.6 Hz), 3.25 (1H, d, J=2.2 Hz), 3.51 (1H, d, J=2.0 Hz), 4.57 (1H, t, J=7.6 Hz), 7.16 (1H, ddd, J=1.1, 7.0, 7.9 Hz), 7.22 (1H, s), 7.24 (1H, ddd, J=1.1, 7.1, 8.1 Hz), 7.50 (1H, d, J=8.1 Hz), 7.64 (1H, d, J=7.8 Hz)

EXAMPLE 92

N-{N-[(2S,3S)-3-trans-ethoxycarbonyloxirane-2-carbonyl]-3-(2-naphthyl)-L-alanyl}-1-amino-3-methylbutane In substantially the same manner as in Example 5, 1-amino-3-methylbutane (128 µl) was condensed with Boc-3-(2,naphthyl)-L-alanine (315 mg, manufactured by Bachem Fein Chemikalien AG, Switzerland) to give N-[Boc-3-(2-naphthyl)-L-alanyl]-1-amino-3-methylbutane (374 mg) as a white powder (yield 97%). After Boc group elimination with trifluoroacetic acid, the product was condensed with (2S,3S)-ethyl hydrogen trans-epoxysuccinate (153 mg) as obtained in Reference Example 8 to yield the title compound (compound 90; 276 mg) as a white powder (yield 75%).

$[\alpha]_D$+41° (c 0.58, CHCl$_3$, 25° C.)

Elemental analysis for $C_{24}H_{30}N_2O_5$: Calcd.: C, 67.58; H, 7.09; N, 6.57 Found: C, 67.34; H, 7.07; N, 6.64

$^1$H NMR δ ppm (CDCl$_3$) 0.74 (3H, d, J=6.6 Hz), 0.76 (3H, d, J=6.6 Hz), 1.13 (2H, m), 1.27 (3H, t, J=7.2 Hz), 1.29 (1H, m), 3.10 (2H, m), 3.16 (1H, d, J=1.8 Hz), 3.19 (2H, d, J=7.5 Hz), 3.63 (1H, d, J=1.9 Hz), 4.21 (2H, m), 4.63 (1H, dt, J=7.8, 7.6 Hz), 5.57 (1H, t, J=5.5 Hz), 6.86 (1H, d, J=7.9 Hz), 7.32 (1H, dd, J=1.7, 8.4 Hz), 7.47 (2H, m), 7.62 (1H, br s), 7.80 (3H, m)

EXAMPLE 93

N-{N-[(2S,3S)-3-trans-carboxyoxirane-2-carbonyl]-3-(2-naphthyl)-L-alanyl}-1-amino-3-methylbutane In substantially the same manner as in Example 27, the compound 90 (100 mg) was subjected to alkali hydrolysis of ethyl ester. The reaction mixture was adjusted to pH 3, which was then concentrated. Resulting powdery precipitate was recovered by filtration, which was dried to yield the title compound (compound 91; 81 mg) (yield 87%).

$[\alpha]_D$+65° (c 0.61, MeOH, 25° C.)

Elemental analysis for $C_{22}H_{26}N_2O_5 \cdot 0.8H_2O$: Calcd.: C, 64.00; H, 6.74; N, 6.79 Found: C, 64.00; H, 6.75; N, 6.90

$^1$H NMR δ ppm (CDCl$_3$) 0.64 (3H, d, J=6.5 Hz), 0.68 (3H, d, J=6.6 Hz), 0.99 (2H, m), 1.16 (1H, m), 2.94 (1H, m), 3.18 (3 H, m), 3.52 (1H, d, J=1.5 Hz), 3.61 (1H, d, J=1.5 Hz), 4.80 (1H, dt, J=7.9, 8.0 Hz), 5.73 (1H, br s), 6.33 (1H, t, J=5.5 Hz), 7.29 (1H, dd, J=1.5, 8.5 Hz), 7.45 (2H, m), 7.61 (1H, br s), 7.76 (3H, m), 8.26 (1H, d, J=8.5 Hz)

EXAMPLE 94

Preparation of main culture broth

*Trichoderma aureoviride* FL-42547 strain grown on potato-dextrose agar slant medium was inoculated to 500 ml of a seed medium (pH 7.0) containing 2% glucose, 3% soluble starch, 1% soybean flour, 0.3% corn steep liquor, 0.5% peptone, 0.3% sodium chloride and 0.5% calcium carbonate in a 2 L Sakaguchi flask, and cultured at 28° C. for 48 hours on a reciprocal shaker. 500 ml of this culture broth was transferred to 120 liters of a main medium containing 5% dextrin, 3% corn steep liquor, 0.5% polypepton, 1% calcium chloride and 0.5% calcium carbonate (pH 7.0) in a 200 liter stainless steel tank. The fermentation was carried out at 24° C. with aeration of 120 liters/min, agitation of 180 rpm/min and an inner pressure of 1 kg/cm$^2$ for 5 days to yield the main culture broth.

EXAMPLE 95

TAN-1803 monohydrochloride

The culture broth (225L) obtained in Example 94 was filtered using a filter aid (Radiolite 600, produced by Showa Chemical Industry). After adjustment to pH 7.0, the filtrate (180L) was subjected to column chromatography with Diaion HP-20 (30L), washed with water (90L) and then eluted with 50% (v/v) aqueous methanol (150L). The eluate was concentrated to 50L under reduced pressure, and passed through a column packed with Amberlite IRC-50 (H type, 14L), washed with water (42L) and then eluted with 1M saline (70 L). After adjustment to pH 7.0, the eluate was subjected to column chromatography with Diaion HP-20 (30L), washed with water (90L) and then eluted with 50% (v/v) aqueous methanol/0.01M hydrochloric acid (90L). After adjustment to pH 7.0, the eluate was concentrated under reduced pressure, subjected to column chromatography with Diaion HP-20 (100–200 mesh, 500 ml), washed with water (1.5L) and then eluted with 50% (v/v) aqueous methanol (1.0L). The eluate was concentrated and passed through a column packed with CM-Sephadex C-25 (Na type, 200 ml), washed with water (600 ml), and then eluted and fractionated with 0.05M saline. The fraction showing a single peak in analytical HPLC was collected and desalinized with Diaion HP-20 (100–200 mesh, 150 ml). After concentration, the eluate was lyophilized to yield N-{N-[(2S,3S)-3-trans-carboxyoxirane-2-carbonyl]-L-leucyl}-N-(3-aminopropyl)-1,4-diaminobutane (TAN-1803 monohydrochloride) (compound 92; 880 mg).

Figure 13:
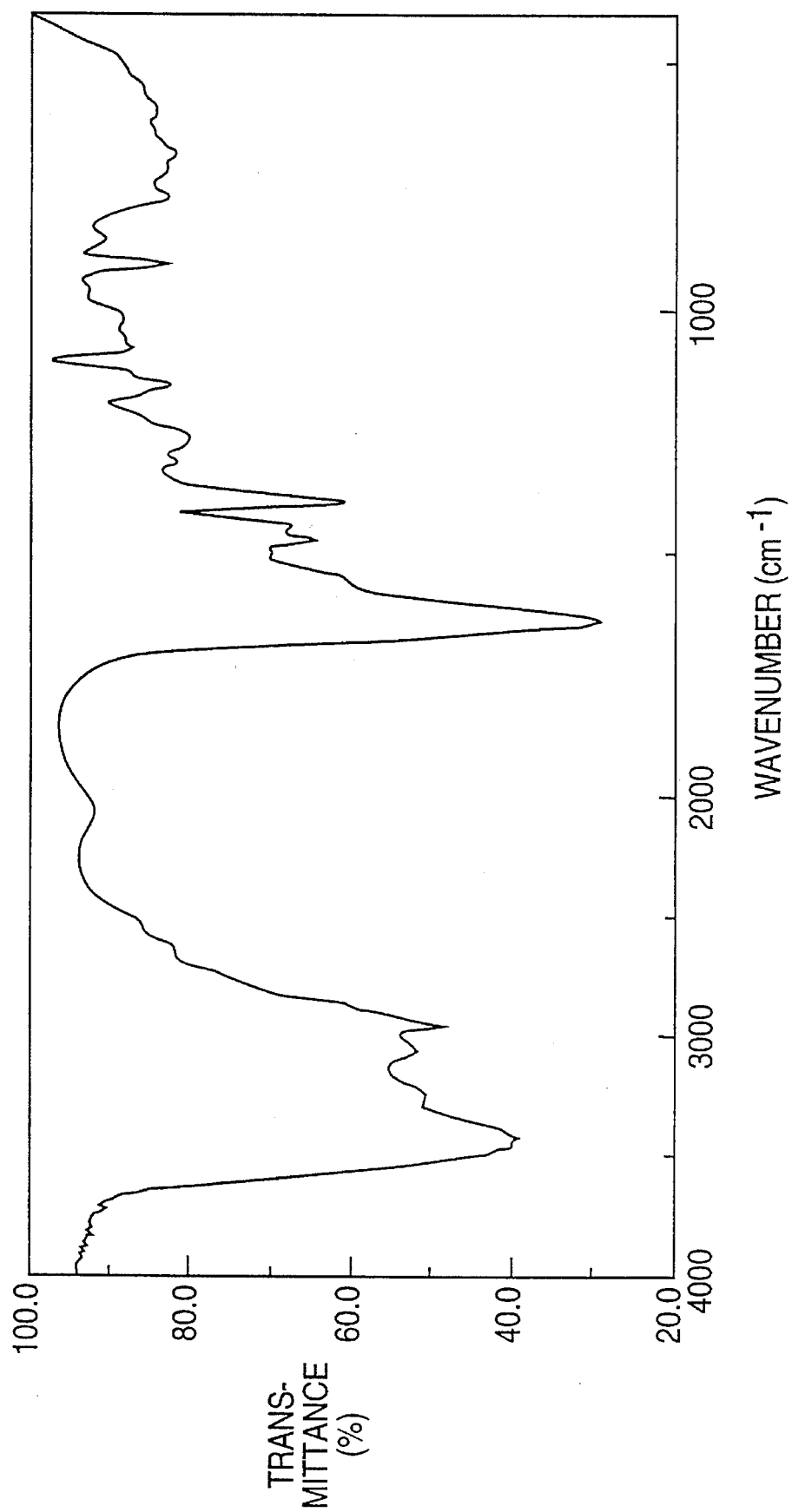
Figure 14:
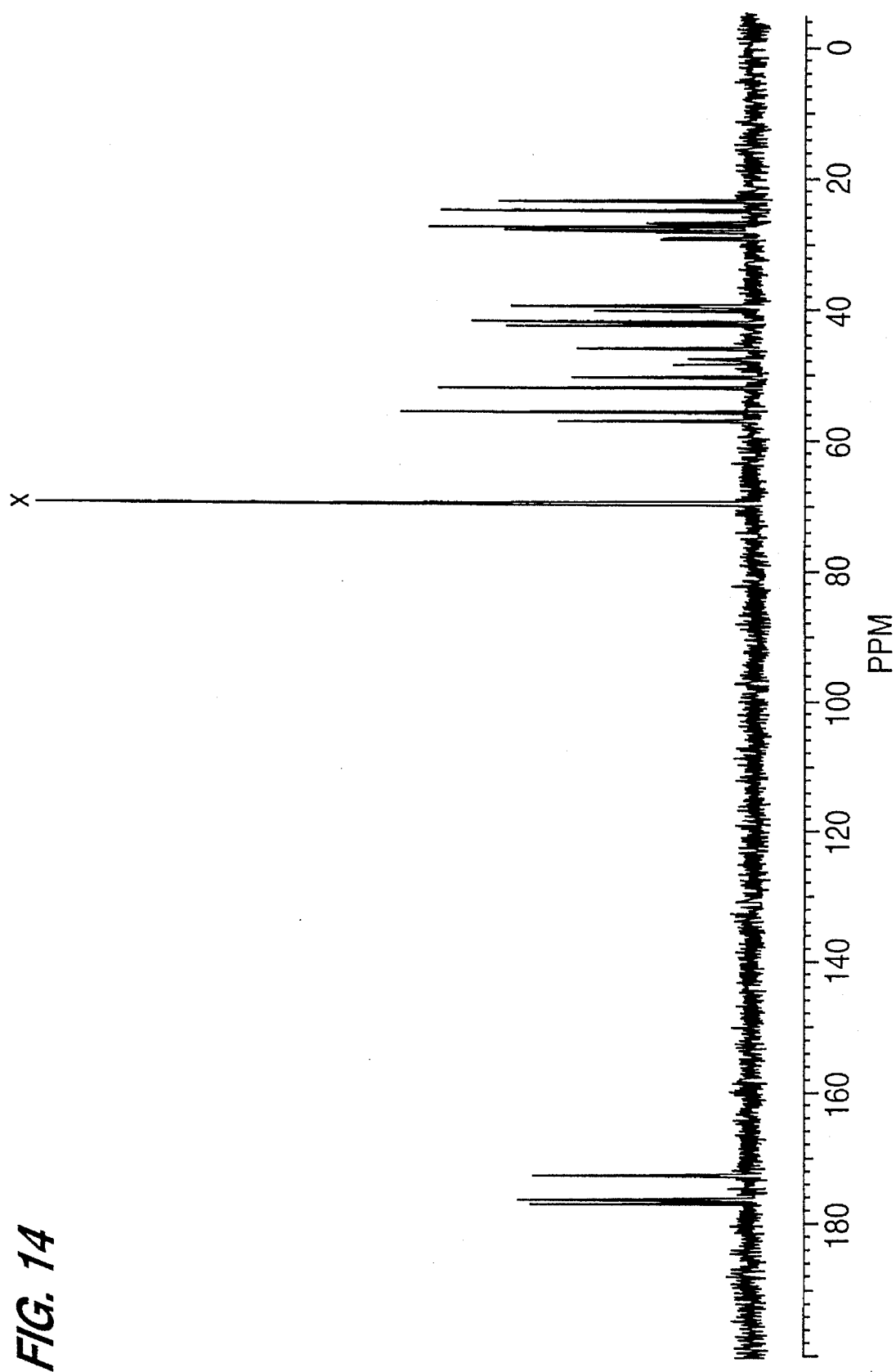

1) Appearance: White powder
2) Optical rotation: +20° (c 0.53, 0.1N hydrochloric acid, 24° C.)
3) Molecular weight: m/z 373 (M+H)$^+$, (SI-mass spectrum)
4) Elemental analysis (%, 1 mol water assumed) Found: C, 47.33; H, 8.23; N, 13.53; Cl, 9.16 Calculated: C, 47.83; H, 8.26; N, 13.12; Cl, 8.30
5) Molecular formula: $C_{17}H_{32}N_4O_5 \cdot HCl$
6) UV spectrum in water: End absorption
7) IR spectrum (in KBr tablet, major absorptions shown, wavenumber cm$^{-1}$, FIG. 13): 3430, 3260, 3060, 2960, 1630, 1470, 1390, 900, 760
8) $^{13}$C NMR spectrum (75 Mz, in heavy water, δ ppm. TAN-1803 occurs as a mixture of two conformers in heavy water; the signal of the major conformer is shown. FIG. 14): 177.1 (Q), 176.6 (Q), 172.4 (Q), 57.2 (CH), 55.6 (CH), 51.8 (CH), 50.3 (CH$_2$), 45.9 (CH$_2$), 42.5 (CH$_2$), 42.1 (CH$_2$), 39.8 (CH$_2$), 28.1 (CH$_2$), 27.9 (CH$_2$), 27.4 (CH), 27.0 (CH$_2$), 25.3 (CH$_3$), 23.3 (CH$_3$)
9) Coloring reactions:
   Positive; ninhydrin reaction, peptide reaction, phosphomolybdic acid reaction
   Negative; Sakaguchi reaction, Ehrlich reaction
10) High performance liquid chromatography (HPLC):
   Column; YMC-Pack A-312, ODS
   Mobile phase; 5% (v/v) acetonitrile/0.01 M phosphate buffer (pH 3.0)
   Flow rate; 2.0 ml/min
   Detection; 214 nm
   Retention time; 3.9 minutes
11) Thin-layer chromatography (TLC):
   Carrier; Silica gel 60F254 (produced by Merck, Germany)
   Developing solvent (by volume); n-butanol:acetic acid:water (2:1:1)
   Rf value; 0.19

EXAMPLE 96

N-Z-N'-{N-[(2S,3S)-3-trans-ethoxycarbonyloxirane-2-carbonyl]-L-leucyl}-N'-(Z-3-aminopropyl)-1,4-diaminobutane After N-Z-N'-(Z-3-aminopropyl)-1,4-diaminobutane (1.15 g) as produced from 3-amino-1-propanol and 1,4-diaminobutane in accordance with the method described in Japanese Patent Unexamined Publication No. 192347/1982 was suspended in DMF (30 ml), triethylamine (427 μl), Boc-L-Leu-OH·H$_2$O (763 mg, produced by Peptide Institute, Inc.), HOBT (413 mg) and WSC (587 mg) were added under ice cooling conditions, followed by stirring at room temperature for 12 hours. After the reaction mixture was concentrated to dryness, ethyl acetate (200 ml) was added; the mixture was sequentially washed with 10% aqueous citric acid, 2% aqueous sodium hydrogen carbonate and saturated saline, and then dried over anhydrous sodium sulfate. The dry product was subjected to silica gel column chromatography (Kieselgel 60, produced by E. Merck, Germany, 120 ml) for elution with a hexane eluent supplemented with sequentially added ethyl acetate, to yield N-(Boc-L-leucyl)-N-(Z-3-aminopropyl)-N'-Z-1,4-diaminobutane (1.40 g) (yield 81%) from the fraction eluted with 50–60% (v/v) ethyl acetate. To this compound (1.38 g), TFA (14 ml) was added; the mixture was kept standing for i hour. After addition of ethyl acetate (200 ml), the reaction mixture was sequentially washed with 2% aqueous sodium hydrogen carbonate and saturated saline. After drying over anhydrous sodium sulfate, the mixture was concentrated to dryness to yield N-(L-leucyl)-N-(Z-3-aminopropyl)-N'-Z-1,4-diaminobutane (1.09 g) (yield 94%).

After this compound (1.06 g) was dissolved in dichloromethane (30 ml), (2S,3S)-ethyl hydrogen trans-epoxysuccinate as described in Reference Example 8 (356 mg), HOBT (300 mg) and WSC (426 mg) were added, followed by stirring at room temperature for 14 hours. After the reaction mixture was concentrated to dryness, ethyl acetate was added; the mixture was sequentially washed with 10% aqueous citric acid, 2% aqueous sodium hydrogen carbonate and saturated saline, and then dried over anhydrous sodium sulfate. The dry product was subjected to silica gel column chromatography (60 ml) for elution with a hexane eluent supplemented with sequentially added ethyl acetate to yield the title compound (compound 93; 601 mg) from the fraction eluted with 65% (v/v) ethyl acetate (yield 45%).

$[\alpha]_D$+18° (c 0.50, CHCl$_3$, 24° C.)

Elemental analysis for $C_{35}H_{43}N_4O_9 \cdot H_2O$: Calcd.: C; 61.21, H; 7.34, N; 8.16 Found: C; 61.42, H; 7.20, N; 7.99

$^1$H NMR δ ppm (DMSO-d$_6$) (compound 93 occurs as a mixture of two conformers in DMSO-d$_6$) 0.87 (6H, m), 1.23 (3H, t×2, J=7.0 Hz), 1.23–1.85 (9H, m), 2.90–3.40 (8H, m), 3.59 (1H, d, J=2.0 Hz), 3.71 (1H, d×2, J=2.0 Hz), 4.17 (2H, m), 4.69 (1H, m), 5.00 (4H, s), 7.15–7.40 (12H, m), 8.75 (1H, d×2, J=7.0 Hz)

EXAMPLE 97

N-Z-N'-{N-[(2S,3S)-3-trans-carboxyoxirane-2-carbonyl]-L-leucyl}-N'-(Z-3-aminopropyl)-1,4-diaminobutane After compound 93 (476 mg) was dissolved in methanol (30 ml), 1N aqueous sodium hydroxide (784 μl) was added under ice cooling conditions, followed by stirring at room temperature for 1.5 hours. After the reaction mixture was concentrated in the presence of 1N hydrochloric acid (140 μl) water (50 ml) was added. After adjustment to pit 2.5, the aqueous solution was extracted with ethyl acetate (50 ml) 3 times. The organic solvent layer was washed with saturated saline, dried over anhydrous sodium sulfate, and then concentrated to dryness, to yield the title compound (compound 94; 450 mg) (yield 99%).

$[\alpha]_D$+25° (c 0.51, MeOH, 24° C.)

Elemental analysis for $C_{33}H_{44}N_4O_9 \cdot 0.5H_2O$: Calculated: C; 61.00, H; 6.98, N; 8.62 Found: C; 61.15, H; 6.96, N; 8.67

$^1$H NMR δ ppm (DMSO-d$_6$) (compound 94 occurs as a mixture of two conformers in DMSO-d$_6$) 0.87 (6H, m), 1.20–1.85 (9H, m), 2.87–3.60 (8H, m), 3.44 (1H, d, J=2.0 Hz), 3.64 (1H, d×2, J=2.0 Hz), 4.70 (1H, m), 5.00 (4H, s), 7.15–7.40 (12H, m), 8.69 (1H, d×2, J=6.0 Hz)

EXAMPLE 98

TAN-1803 monohydrochloride

After compound 94 (343 mg) was dissolved in methanol (8 ml), water (4 ml), acetic acid (31 μl) and 10% (w/w) palladium/activated carbon (34 mg) were added, followed by stirring at room temperature for 1.5 hours in hydrogen atmosphere. After the catalyst was filtered off, the filtrate was concentrated and then subjected to preparative HPLC [column YMC-Pack, D-ODS-5 (S-5 120A); mobile phase 2% (v/v) acetonitrile/0.01 M phosphate buffer (pH 6.3); flow rate 10 ml/min]. The fraction showing a single peak of TAN-1803 in analytical HPLC was collected, passed through a column packed with Amberlite IRA-402 (Cl type, 100 ml), and washed with water (100 ml). The effluent was combined with washings, concentrated, and then desalinized with Diaion HP-20 (100–200 mesh, 80 ml). The eluate was concentrated and lyophilized to yield TAN-1803 monohydrochloride (compound 92; 107 mg) (yield 49%).

The physico-chemical data on this compound agreed with those on the compound obtained from the culture broth.

Preparation Example 1

All the following components, including TAN-1756A as obtained in Example 7, were mixed together and packed in gelatin capsules to yield a capsular preparation containing 80 mg of TAN-1756A per capsule.

| | |
|---|---|
| TAN-1756A | 30 mg |
| Lactose | 100 mg |
| Corn starch | 40 mg |
| Magnesium stearate | 10 mg |
| Total | 180 mg |

Preparation Example 2

All the following components, including TAN-1803 monohydrochloride as obtained in Example 95, were mixed together and packed in gelatin capsules to yield a capsular preparation containing 30 mg of TAN-1803 monohydrochloride per capsule.

| | |
|---|---|
| TAN-1803 monohydrochloride | 30 mg |
| Lactose | 100 mg |
| Corn starch | 40 mg |
| Magnesium stearate | 10 mg |
| Total | 180 mg |

What is claimed is:

1. A compound of the formula:

$$R^1-CH\underset{O}{\underset{\diagdown\diagup}{-}}CH-CONH-CH-CON-R^3$$
$$\qquad\qquad\qquad\quad | \qquad\quad |$$
$$\qquad\qquad\qquad (CH_2)_n \quad R^4$$
$$\qquad\qquad\qquad\quad |$$
$$\qquad\qquad\qquad\quad R^2$$

wherein $R^1$ represents a carboxyl group which may optionally be esterified or amidated; $R^2$ represents a cyclic group which may optionally be substituted or a polar group; n is an integer of 0 to 6; and $R^3$ and $R^4$ are combined with the adjacent nitrogen atom to form a heterocyclic group containing at least two hetero atoms, or a salt thereof.

2. The compound according to claim 1, wherein $R^1$ is a carboxyl group which may optionally be esterified.

3. The compound according to claim 1, wherein $R^1$ is a carboxyl group.

4. The compound according to claim 1, wherein $R^2$ is a cyclic group which may optionally be substituted.

5. The compound according to claim 4, wherein the cyclic group is an aryl group.

6. The compound according to claim 5, wherein the aryl group is $C_{6-14}$ aryl group.

7. The compound according to claim 2, wherein $R^1$ is an esterified carboxyl group represented by the formula $-COOR^5$, wherein $R^5$ is selected from the group consisting of (a) $C_{1-6}$ alkyl groups, which optionally may be substituted with 1 to 3 substituents selected from nitro group, halogen and $C_{2-4}$ alkanoyloxy groups, (b) $C_{6-14}$ aryl groups, which optionally may be substituted with 1 to 3 substituents selected from nitro group, halogen, and $C_{1-4}$ alkoxy groups, and (c) $C_{7-12}$ aralkyl groups, which optionally may be substituted with 1 to 3 substituents selected from nitro group, halogen and $C_{1-4}$ alkoxy groups.

8. The compound according to claim 1, wherein $R^1$ is an amidated carboxyl group represented by the formula $-CONHR^6$, wherein $R^6$ is selected from the group consisting of (a) hydrogen, (b) $C_{1-6}$alkyl groups, which optionally may be substituted with 1 to 3 substituents selected from nitro group and halogen, (c) $C_{6-14}$, aryl groups, which optionally may be substituted with 1 to 3 substituents selected from nitro group, halogen, and $C_{1-4}$ alkoxy groups, and (d) $C_{7-12}$ aralkyl groups, which optionally may be substituted with 1 to 3 substituents selected from nitro group, halogen and $C_{1-4}$ alkoxy groups.

9. The compound according to claim 4, wherein $R^2$ is a cyclic group selected from the group consisting of (a) $C_{3-8}$ cycloalkyl groups, (b) $C_{3-8}$ cycloalkenyl groups, (c) $C_{6-14}$ aryl groups, (d) 5-membered heterocyclic groups containing 1 to 4 hetero atoms selected from oxygen, sulfur, and nitrogen, or a condensed heterocyclic group thereof, and (e) 6-membered heterocyclic groups containing 1 to 4 hetero atoms selected from oxygen, sulfur and nitrogen, or a condensed heterocyclic group thereof.

10. The compound according to claim 1, wherein the polar group is selected from the group consisting of nitro group, hydroxyl group, oxo group, thioxo group, cyano group, carbamoyl group, carboxyl group, $C_{2-5}$ koxycarbonyl groups, $C_{8-13}$ aralkyloxycarbonyl groups, $C_{7-11}$ aryloxycarbonyl groups, sulfo group, mercapto group, $C_{1-4}$ alkoxy groups, $C_{6-10}$ aryloxy groups, $C_{7-12}$ aralkyloxy groups, $C_{1-4}$ alkanoyloxy groups, $C_{7-11}$ arylcarbonyloxy groups, $C_{1-4}$ alkylthio groups, $C_{6-10}$ arylthio groups, $C_{7-19}$ aralkylthio groups, $C_{1-5}$ alkylsulfinyl groups, $C_{6-10}$ alkylsulfinyl groups, $C_{1-6}$ alkylsulfonyl groups, $C_{6-10}$ arylsulfonyl groups, amino group, $C_{1-8}$ alkanoylamino groups, mono- or di-$C_{1-4}$ alkylamino groups, $C_{7-11}$ arylcarbonylamino groups, $C_{2-5}$ alkoxycarbonylamino groups, $C_{8-13}$ aralkyloxycarbonylamino groups, $C_{1-5}$ alkylsulfonylamino groups, $C_{6-10}$ arylsulfonylamino groups, $C_{1-6}$ alkanoyl groups, $C_{8-13}$ aralkylcarbonyl groups, $C_{7-11}$ arylcarbonyl groups, mono- or di-$C_{1-4}$ alkylcarbamoyl groups, phosphono group, mono- or di-$C_{1-4}$ alkylphosphono groups, guanidyl groups which optionally may be substituted with nitro group, amidino group, and mono- or di-$C_{1-4}$ alkylsulfamoyl groups.

11. The compound according to claim 10, which is selected from thiomorpholino, morpholino, piperazinyl, 4H-1,4-oxazinyl and 4H-1,4-thiazinyl.

12. The compound according to claim 1, wherein the heterocyclic group formed by $R^3$ and $R^4$ is a 6-membered heterocyclic group.

13. The compound according to claim 1, wherein the compound is N-[N-[(2S,3S)-3-trans-ethoxycarbonyloxirane-2-carbonyl]-L-phenylalanyl]morpholine.

14. The compound according to claim 1, wherein the compound is N-[N-[(2S,3S)-3-trans-carboxyoxirane-2-carbonyl]-L-phenylalanyl]morpholine or a salt thereof.

15. The compound according to claim 1, wherein the compound is N-[N-[(2S,3S)-3-trans-ethoxycarbonyloxirane-2-carbonyl]-L-tyrosyl]morpholine of a salt thereof.

16. The compound according to claim 1, wherein the compound is N-[N-[(2S,3S)-3-trans-carboxyoxirane-2-carbonyl]-L-tyrosyl]morpholine or a salt thereof.

17. The compound according to claim 1, wherein the compound is N-[N-[(2S,3S)-3-trans-ethoxycarbonyloxirane-2-carbonyl]-3-(2-naphthyl)-L-alanyl]morpholine.

18. The compound according to claim 1, wherein the compound is N-[N-[(2S,3S)-3-trans-carboxyoxirane-2-carbonyl]-3-(2-naphthyl)-L-alanyl]morpholine or a salt thereof.

19. A composition which comprises a compound or salt thereof according to claim 1 and a pharmaceutically acceptable carrier, excipient or diluent.

20. A method for preventing or treating osteoporosis in a mammal, which comprises administering an effective amount of the compound as defined in claim 1 or a pharmaceutically acceptable salt thereof to the mammal.

21. A method for inhibiting a thiol protease in a mammal, which comprises administering an effective amount of the compound as defined in claim 1, or a pharmacologically acceptable salts thereof to the mammal.

22. A method for preventing or treating a bone disease in a mammal, which comprises administering an effective amount of the compound as defined in claim 1, or a pharmacologically acceptable salts thereof to the mammal.

* * * * *